(12) United States Patent
Owens et al.

(10) Patent No.: US 6,914,136 B2
(45) Date of Patent: Jul. 5, 2005

(54) METHODS AND COMPOSITIONS FOR EXPRESSING POLYNUCLEOTIDES SPECIFICALLY IN SMOOTH MUSCLE CELLS IN VIVO

(75) Inventors: Gary K. Owens, Earlysville, VA (US); Ichiro Manabe, Taito (JP)

(73) Assignee: Setagon, Inc., Charlottesville, VA (US)

( * ) Notice: Subject to any disclaimer, the term of this patent is extended or adjusted under 35 U.S.C. 154(b) by 0 days.

(21) Appl. No.: 10/057,726

(22) Filed: Jan. 24, 2002

(65) Prior Publication Data

US 2003/0017549 A1 Jan. 23, 2003

Related U.S. Application Data

(63) Continuation-in-part of application No. 09/600,319, filed as application No. PCT/US99/01038 on Jan. 15, 1999, now Pat. No. 6,780,610.
(60) Provisional application No. 60/263,811, filed on Jan. 24, 2001, and provisional application No. 60/071,300, filed on Jan. 16, 1998.

(51) Int. Cl.$^7$ .......................... C07H 21/04; C12N 5/16; C12N 15/63; A01K 67/027

(52) U.S. Cl. ................... 536/24.1; 435/325; 435/320.1; 435/69.1; 800/13

(58) Field of Search ...................... 536/24.1; 435/320.1; 435/325, 69.1; 800/13

(56) References Cited

FOREIGN PATENT DOCUMENTS

| EP | 0807688 A2 | 5/1997 |
|----|------------|--------|
| WO | WO 94/20629 A1 | 9/1994 |
| WO | WO 99/36101 A1 | 7/1999 |

OTHER PUBLICATIONS

Arnone et al. The hardwiring of development: organization and function of genomic regulatory systems. Development. May 1997;124(10):1851064.*
NCBI Database Online, Accession No. U91323 [gi:3582311].*
Forsythe et al. CArG–containing enhancers in the first intron of the human smooth muscle myosin heavy chain (h–sm–MHD) gene. FASEB J. 1999; 13(4): A169.*
Aikawa et al., "Human smooth Muscle Myosin Heavy Chain Isoforms as Molecular Markers for Vascular Development and Atherosclerosis," *Circulation Research*, 73(6):1000–1012, (1993).
Aikawa et al., "Redifferentiation of Smooth Muscle Cells After Coronary Angioplasty Determined via Myosin Heavy chain Expression," *Circulation*, 96(1):82–90 (1997).
Babij et al., "Tissue–specific and developmentally regulated alternative splicing of a visceral isoform of smooth muscle myosin heavy chain," *Nuc. Acids Res.*, 21(6):1467–1471 (1993).

Babji et al., "Differential expression of SM1 and SM2 myosin isoforms in cultured vascular smooth muscle," *Am J. Physiol.*, 262:C607–C613 (1991).
Babji et al., "Characterization of a mammalian smooth muscle myosin heavy–chain gene: Complete nucleotide and protein coding sequence and analysis of the 5' end of the gene," *PNAS*, 88:10676–10680 (1991).
Babji et al., "Myosin Heavy Chain Isoform diversity in Smooth Muscle is Produced by Differential RNA Processing," *J. Mol. Biol.*, 210:673–679 (1989).
Borrione et al., "Myosin heavy–chain isoforms in adult and developing rabbit vascular smooth muscle," *Eur. J. Biochem.*, 183:413–417 (1989).
Bouvagnet et al., "Multiple Positive and Negative 5' Regulatory elements control the Cell–Type–Specific expression of the Embryonic Skeletal Myosin Heavy–Chain Gene," *Molecular and Cellular Biol.*, 7(12):4377–4389 (1987).
Chamley–Campbell et al., "What Controls Smooth Muscle Phenotype," *Atherosclerosis*, 40:347–347 (1981).
Firulli et al., "Modular regulation of muscle gene transcription: a mechanism for muscle cell diversity," *Trends in Genetics*, 13(9):364–369 (1997).
Fisher et al., "Developmental and Tissue Distribution of Expression of non Muscle and Smooth Muscle Isoforms of Myosin Light Chain Kinase," *Biochem. and Biophys. Res. Comm.*, 217(2):696–703 (1995).
Frid et al., "Myosin Heavy–Chain Isoform Composition and distribution in Developing and Adult Human Aortic Smooth Muscle," *J. Vas. Res.*, 30:279–292 (1993).
Kallmeier et al., "A Novel Smooth Muscle–specific Enhancer Regulates Transcription of the Smooth Muscle Myosin Heavy Chain Gene in Vascular Smooth Muscle Cells," *J. Biol. Chem.*, 270(52):30949–30957 (1995).
Katoh et al., "Identification of Functional Promoter Elements in the Rabbit Smooth Muscle Myosin Heavy Chain Gene," *J. Biol. Chem.*, 269(48):30538–30545 (1994).
Kawamoto et al., "Characterization of Myosin Heavy Chain in Cultured Aorta Smooth Muscle Cells," *J. Biol. Chem.*, 262(15):7282–7288 (1987).

(Continued)

*Primary Examiner*—David Guzo
*Assistant Examiner*—Daniel M. Sullivan
(74) *Attorney, Agent, or Firm*—Townsend and Townsend and Crew LLP

(57) ABSTRACT

The present invention generally relates to promoters, enhancers and other regulatory elements of smooth muscle cells ("SMC"). The invention more particularly relates to methods for the targeted knockout, or over-expression, of genes of interest within smooth muscle cells or within a subtype of smooth muscle cells. The invention further relates to methods of conferring polynucleotide expression in vivo specifically in smooth muscle cells or in subtypes of smooth muscle cells.

28 Claims, 25 Drawing Sheets

OTHER PUBLICATIONS

Kelley et al., "An Insert of Seven Amino Acids Confers Functional Differences between Smooth Muscle Myosins from the Intestines and Vasculature," *J. Biol. Chem.*, 268(17):12848–12854 (1993).

Kocher et al., "Cytoskeletal Features of Normal and Atheromatous Human Arterial Smooth Muscle Cells," *Human Pathology*, 17(9):875–880 (1986).

Kocher et al., "Phenotypic Features of Smooth Muscle Cells during the Evolution of Experimental Carotid Artery Intimal Thickening biochemical and Morphologic Studies," *Laboratory Invest.*, 65(4):459–470 (1991).

Hamada et al., "Distinct vascular and intestinal smooth myosin heavy chain mRNAs are encoded by a single–copy gene in the chicken," *Biochem. Biophys. Res. Comm.* 170(1):53–58 (1990).

Madsen et al., "Smooth muscle–Specific Expression of the Smooth Muscle Myosin Heavy Chain Gene in Transgenic Mice Requires 5'–Flanking and First Intronic DNA Sequence," *Circulation Research*, 82:908–917 (1998).

Madsen et al., "Identification of a Positive CIS Element in the Rat Smooth Muscle Myosin Heavy Chain Promoter," *Federation of American Societies of Experimental Biology Journal*, 10(3):A343, abst. 1977 (1996).

Madsen et al., "Interaction of CArG Elements and a GC–rich Repressor Element in Transcriptional Regulation of the Smooth Muscle Myosin Heavy Chain Gene in Vascular Smooth Muscle Cells," *J. Biol. Chem.*, 272(47):29842–29851 (1997).

Madsen et al., "Expression of the Smooth Muscle Myosin heavy Chain Gene Is Regulated by a Negative–acting GC–rich Element Located between Two Positive–acting Serum Response Factor–binding Elements," *J. Biol. Chem.*, 272(10):6332–6340 (1997).

Manabe et al., "CArG elements control smooth muscle subtype–specific expression of smooth muscle myosin in vivo," *J. Clin. Invest.*, 107(7):823–834 (2001).

Manabe et al., "The Smooth Muscle Myosin Heavy Chain Gene Exhibits Smooth Muscle Subtype–selective Modular Regulation in Vivo", *J. Biol. Chem.*, 276(42):39076–39087 (2001).

Miano et al., "Smooth Muscle Myosin Heavy Chain Exclusively Marks the Smooth Muscle Lineage During Mouse Embryogenesis," *Circulation Research*, 75:803–812 (1994).

Nagai et al., "Identification of Two Types of Smooth Muscle Myosin Heavy Chain Isoforms by cDNA Cloning and Immunoblot Analysis*," *J. Biol. Chem.*, 264(17):9734–9737 (1989).

Owens, G.K., "Regulation of Differentiation of Vascular Smooth Muscle Cells," *Physiological Reviews*, 75(3):487–517 (1995).

Regan et al., "Development of a Smooth Muscle–Targeted Cre Recombinase Mouse Reveals Novel Insights Regarding Smooth Muscle Myosin Heavy Chain Promoter Regulation," *Circ. Res.*, 87:363–369 (2000).

Reusch et al., "Mechanical Stain Increases Smooth Muscle and Decreases Nonmuscle Myosin Expression in Rat Vascular Smooth Muscle Cells," *Circulation Research*, 79:1046–1053 (1996).

Ross et al., "The pathogenesis of atherosclerosis: a perspective for the 1990s," *Nature*, 362:801–809 (1993).

Rovner et al., "Two different heavy chains are found in smooth muscle myosin," *Am. J. Physiol.*, 250:C861–C870 (1986).

Rovner et al., "Expression of Smooth Muscle and Non-muscle Myosin Heavy Chains in Cultured Vascular Smooth Muscle Cells*," *J. Biol. Chem.*, 261(31):14740–14745 (1986).

Sartore et al., "Myosin Isoform Expression in Smooth Muscle Cells during Physiological and Pathological Vascular Remodeling," *J. Vasc. Res.*, 31:61–81 (1994).

Sartore et al., "Myosin heavy–chain isoforms in human smooth muscle," *Eur. J. Biochem.*, 179:79–85 (1989).

Sartorelli et al., "Muscle–Specific Gene Expression, A Comparison of Cardiac and Skeletal Muscle Transcription Strategies," *Circulation Research*, 72:925–931 (1993).

Schwartz et al., "Developmental Mechanisms Underlying Pathology of Arteries," *Physiological Reviews*, 70(4):1177–1209 (1990).

Wang et al., "Expression of Smooth Muscle Myosin Isoforms in Urinary Bladder Smooth Muscle during Hypertrophy and Regression," *Laboratory Investigation*, 73(2):244–251 (1995).

Watanabe et al., "Structure and Characterization of the 5'–Flanking Region of the Mouse Smooth Muscle Myosin Heavy Chain (SM 1/2) Gene," *Circulation Research*, 78:978–989 (1996).

White et al., "Identification of Promoter Elements involved in Cell–Specific Regulation of Rat Smooth Muscle Myosin Heavy Chain Gene Transcription*," *J. Biol. Chem.*, 271(25):15008–15017 (1996).

White et al., "Identification of a novel smooth muscle myosin heavy chain cDNA: isoform diversity in the Sl head region," *Am. J. Physiol.*, 264:C1252–C1258 (1993).

Wills et al., "Tissue–specific expression of an anti–proliferative hybrid transgene from the human smooth muscle α–actin promoter supresses smooth muscle cell proliferation and neointima formation," *Gene Therapy*, 8:1847–1854 (2001).

Loftus, B. et al. "Genome duplications and other features in 12 Mb of DNA sequence from human chromosome 16p and 16q," *Genomics* 1999, pp. 295–308, vol. 60.

Franz, Wolfgang M. et al.; "The 2.3 kb smooth muscle myosin heavy chain promoter directs gene expression into the vascular system of transgenic mice and rabbits"; 1999, *Cardiovascular Research*, vol. 43, pp. 1040–1048.

Ll, Li et al.; "Evidence for Serum Response Factor–Mediated Regulatory Networks Governing SM22α Transcription in Smooth, Skeletal, and Cardiac Muscle Cells"; 1997, *Developmental Biology*, Vo. 187, pp. 311–321.

Manabe, I. et al.; "Full transcriptional activity of the smooth muscle myosin heavy chain gene requires multiple CArG elements in the 5'–flanking and first intronic sequence,"; 1999, *FASEB Journal*, vol. 13, No. 4, Part 1, 1 page abstract.

Mericskay, Mathias et al.; "An Overlapping CArG/Octamer Element is Required for Regulation of desmin Gene Transcription in Arterial Smooth Muscle Cells"; 2000, *Developmental Biology*, vol. 226, pp. 192–208.

* cited by examiner

FIG. 4

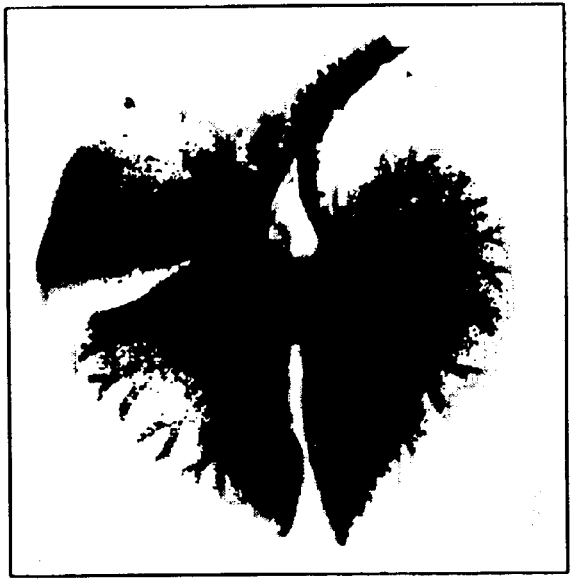
Conducting airways and lungs.
Stomach, small intestine, and esophagous.
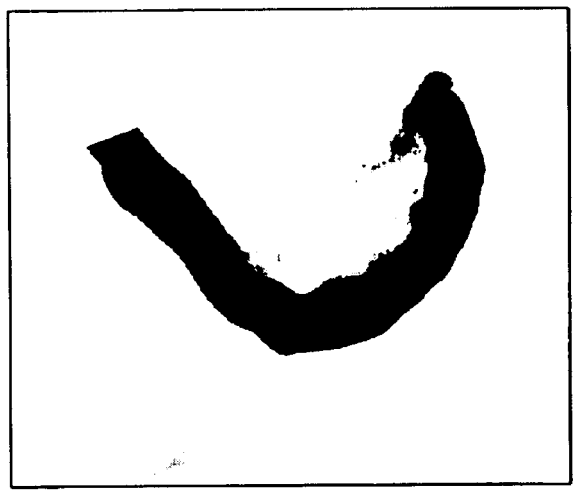
Colon.
Iliac Artery.
Fig. 9

Ileum
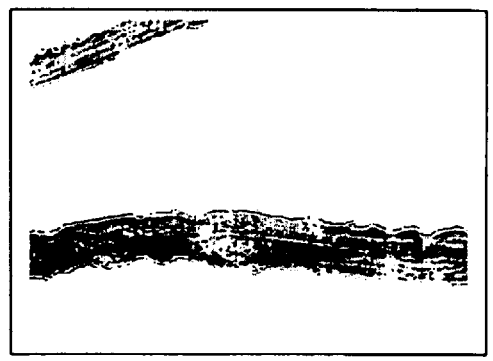
Abdominal aorta
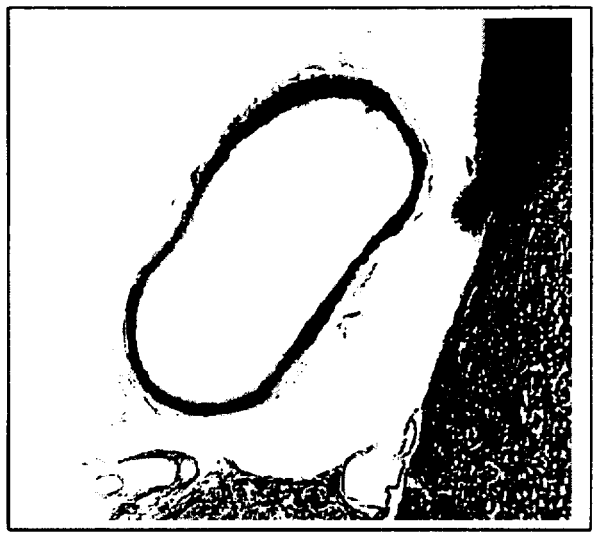
Small artery (circle of Willis)
Colon
FIG. 10

SM MHC 5'-Flanking sequence

```
                    CArG3
Rat    : GGGAGG---CTGCAGGGACCATATTTAGTCAGGGGGAGCCAG-AGCCC--CGCTGGTATG
         ||  ||   ||  ||   ||||||||||||||||||||||||| |||||  ||||||||||
Human  : GGAAGGCCACT-C-GGCACCATATTTAGTCAGGGGGAGCCGGCAGCCCAGAGCTGGTATG
                                                          CArG2
Rat    : C--CAAGCTGGGAATTCTTGTTTC--G-A-GAAT-TGCGCCTGGCCTTTTTGGGTTGTTT
          |   ||||||||||||||||| ||   |   | || ||||||||| |||||||||| ||||| |
Human  : CGGC--GCTGGGAATTCCTG---CAGGAAGGAGTCCGCGCCTGCCCTTTTTGGGTTGTCT
         GC repressor
Rat    : CCCGCCCAGGCCC------------AGGAGGGGGACCAGCTCAGG-ACCTC-GAGG-G-
         ||||||| |               ||||||||||  ||  |    ||   ||
Human  : CCCGCCCGCCGCTCCCGCCGCTCCCGGGGAGGGGGACCGGCCCGGCCCCGGCCCGGCCCGG Rat    : TCCGTG--CGCGGGGAGCGA-----------------------------GGCTCCCC
                 ||||                                      |||||||
Human  : GAACCTCGGAGGAGCTGGTGCCCGCGGGGAGCGGAGCGCCCGGGCTGCCCGCGGGTCCCC
                                                    CArG1
Rat    : GGCCTGGCATGAGGCCA---CTCTGCCTCGACTTCCTTTTATGGCCTGAGTGTGAGTGCA
         ||||||||  ||||||     |  |||||||||| ||||||||||| |||| ||||| |||
Human  : GGCCTGGCGCGGGGCCAGCCCACCGCCTCGACTTCCTTTTATGGCCTGTGTGTGCGTGCG Rat    : TGGAGAGTG-G-GAGGGAGGGAGGGA
         ||||||| | |  ||||||||||||
Human  : TGGACAG-GAGCG-GGAGGGAGGGA
```

FIG. 11

Anterior    Posterior

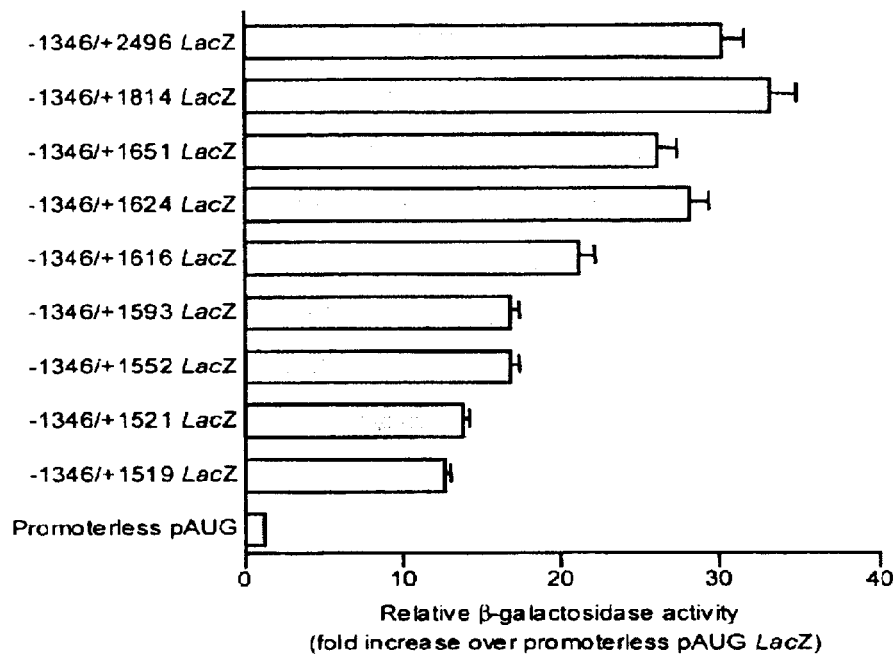

FIG. 18A

```
Rat +1422   GT GGATG    TGGTAGGGTTCCAG   GAG GCTGGCGTGATCTCAAACATGCCTGG
Human +1776 AG--G--C--CCA--CCGA-AG-----AAC-T-AA--A--TG-G---TTTC-GA-AAGCC Rat +1472   GCCAAGC CACCCTGGAGAAACC TGGACTTTTATTATCAGATCTGAAATAGA GCCTC
Human +1836 ----G--TTG--T--T-A-A---A--TTT-----------TG--C--------TGTGT-A Rat +1528   TTCCGTACAAGGTAGTCACTATGGAT    TTATCATTACTTTTCTGTGGGA-GGCTGGGC
Human +1896 --------------TCTGT------TTG----------------C------G---A-A-A Rat +1584   TGGAGGCAGACATGCCCTTGTATGGTAGTGTTTTCTATGAGGCCATTCCCAGTCCCCCTT
Human +1956 -T------A------ -A-T-----A--C------C---------- ---G-C----- -

Rat +1644   GGCCAATCACCCAGCCTTTCGA TGCAG CC   T G ACTGGCTTGAGTTCTGGGTACT
Human +2014 C-T--G-T----------G- -CC----C--GGT-G-TC-----CCT-GGGATTT--CTA
```

FIG. 18B

METHODS AND COMPOSITIONS FOR EXPRESSING POLYNUCLEOTIDES SPECIFICALLY IN SMOOTH MUSCLE CELLS IN VIVO

CROSS-REFERENCES TO RELATED APPLICATIONS

The present application claims priority to U.S. Provisional Application No. 60/263,811, filed Jan. 24, 2001. The present application is also a continuation-in-part application of U.S. patent application Ser. No. 09/600,319, filed Jul. 13, 2000, now U.S. Pat. No. 6,780,610, which is a U.S. national phase application of international application number PCT/US99/01038, filed Jan. 15, 1999, which claims priority to U.S. Provisional Application No. 60/071,300, filed Jan. 16, 1998. The invention is also related to international application PCT/US99/24972. Each of the aforementioned applications is explicitly incorporated herein by reference in its entirety and for all purposes.

STATEMENT AS TO FEDERAL FUNDING

Work described herein has been supported in part by National Institutes of Health grants R01 HL38854 and P01 HL19242. The U.S. Government may therefore have certain rights in the invention.

FIELD OF THE INVENTION

This invention relates generally to the field of regulation of gene expression, and specifically to smooth muscle specific promoters and enhancers. The invention also relates to methods of modulating gene expression by utilizing smooth muscle specific promoters and enhancers.

BACKGROUND OF THE INVENTION

Smooth muscle cells (SMCs), often termed the most primitive type of muscle cell because they most resemble non-muscle cells, are called "smooth" because they contain no striations, unlike skeletal and cardiac muscle cells. Smooth muscle cells aggregate to form smooth muscle which constitutes the contractile portion of the stomach, intestine and uterus, the walls of arteries, the ducts of secretory glands and many other regions in which slow and sustained contractions are needed.

Abnormal gene expression in SMC plays a major role in numerous diseases including, but not limited to, atherosclerosis, hypertension, stroke, asthma and multiple gastrointestinal, urogenital and reproductive disorders. These diseases are the leading causes of morbidity and mortality in Western Societies, and account for billions of dollars in health care costs in the United States alone each year.

In recent years, the understanding of muscle differentiation has been enhanced greatly with the identification of several key cis-elements and trans-factors that regulate expression of muscle-specific genes. Firulli A. B., et al., 1997, Trends in Genetics, 13:364–369; Sartorelli V. et al., 1993, Circ. Res., 72:925–931. However, the elucidation of transcriptional pathways that govern muscle differentiation has been restricted primarily to skeletal and cardiac muscle. Currently, no transcription factors have yet been identified that direct smooth muscle-specific gene expression, or SMC myogenesis. Owens G. K., 1995, Physiol. Rev., 75:487–517. Unlike skeletal and cardiac myocytes, SMC do not undergo terminal differentiation. Furthermore, they exhibit a high degree of phenotype plasticity, both in culture and in vivo. Owens G. K., 1995, Physiol. Rev., 75:487–517; Schwartz, S. M. et al., 1990, Physiol. Rev., 70:1177–1209. Phenotype plasticity is particularly striking when SMC located in the media of normal vessels are compared to SMC located in intimal lesions resulting from vascular injury or atherosclerotic disease. Schwartz, S. M. et al., 1990, Physiol. Rev., 70:1177–1209; Ross R., 1993, Nature, 362:801–809; Kocher O. et al., 1991, Lab. Invest., 65:459–470; Kocher O. et al., 1986, Hum. Pathol., 17:875–880. Major modifications include decreased expression of smooth muscle isoforms of contractile proteins, altered growth regulatory properties, increased matrix production, abnormal lipid metabolism and decreased contractility. Owens G. K., 1995, Physiol. Rev., 75:487–517. The process by which SMC undergo such changes is referred to as "phenotypic modulation". Chamley-Campbell J. H. et al., 1981, Atherosclerosis, 40:347–357. Importantly, these alterations in expression patterns of SMC protein cannot simply be viewed as a consequence of vascular disease, but rather are likely to contribute to the progression of the disease.

Expression of smooth muscle myosin heavy chain (SM-MHC) appears to be completely restricted to SMC lineages throughout development (Miano J. et al., 1994, Circ. Res., 75:803–812). To date, four SM-MHC isoforms (SMC-1A, SMC-1B, SMC-2A, and SMC-2B) have been identified (Nagai R. et al., 1989, J. Biol. Chem., 264:9734–9737; White S. et al., 1993, Am. J. Physiol., 264:C1252–C1258; Kelley C. A. et al., 1993, J. Biol. Chem., 268:12848–12854), all of which are derived from alternative splicing of a single gene (Miano J. et al., 1994. Circ. Res., 75:803–812; Babij P. et al., 1989, J. Mol. Biol., 210:673–679). Alterations in expression of SM-MHC isoforms have been extensively documented in SMC that have undergone phenotypic modulation either when placed in culture (Rovner A. S., 1986, J. Biol. Chem., 261:14740–14745; Kawamoto S. et al., 1987, J. Biol. Chem., 262:7282–7288), or in vascular lesions of both humans and several animal models of vascular disease (Aikawa M. et al., 1997, Circulation, 96:82–90; Sartore S, et al., 1994, J. Vasc. Res., 31:61–81).

Transcriptional regulation of the SM-MHC gene has been analyzed in cultured SMC and several functional cis-elements have been identified. White S. L. et al., 1996, J. Biol. Chem., 271:15008–15017; Katoh Y. et al., 1994, J. Biol. Chem., 269:30538–30545; Watanabe M. et al., 1996, Circ. Res., 78:978–989; Kallmeier R. C. et al., 1995, J. Biol. Chem., 270:30949–30957; Madsen C. S. et al., 1997, J. Biol. Chem., 272:6332–6340; Madsen C. S. et al., 1997, J. Biol Chem., 272:29842–29851. However, because differentiation of SMC is known to be dependent on many local environmental cues that cannot be completely reproduced in vitro, cultured SMC are known to be phenotypically modified as compared to their in vivo counterparts (Owens G. K., 1995, Physiol. Rev., 75:487–517; Chamley-Campbell J. H. et al., 1981, Atherosclerosis, 40:347–357). As such, certain limitations may apply regarding the usefulness of cultured SMC in defining transcriptional programs that occur during normal SMC differentiation and maturation within the animal.

A few promoters relating to smooth muscles have been described in the art, e.g., promoters for SM-actin and SM22 genes. However, a major disadvantage with these promoters is that they are clearly not SMC specific. SM22 and SM-actin are highly expressed in myofibroblasts during wound repair, within granulomatous tissues, tumors, etc. The promoters for these genes are also transiently activated in skeletal and cardiac muscle during development, and in association with a number of pathological circumstances (e.g. myocardial hypertrophy). In addition, the SM22 promoter fragments tested to date also have very little activity in SMC tissues of adult mice. Thus, such promoters have major limitations in terms of their utility in smooth muscle tissue specific targeting and expression in vivo.

Thus, there is a need in the art for transcription regulatory sequences (e.g., promoters and enhancers) that can direct gene expression specifically in smooth muscle tissues in vivo (e.g., in human or non-human animals). There is also a need for relatively small smooth muscle specific promoter/enhancers that retain high level SMC specific expression in vivo and yet are selectively active in subsets of SMC (e.g. vascular versus gastrointestinal SMC, large versus small arteries, pulmonary versus gastrointestinal SMC, etc.). Methods for utilizing such SMC specific promoters and enhancers to target delivery and expression of polynucleotide to SMCs are also needed. The present invention fulfills these and other needs.

SUMMARY OF THE INVENTION

In one aspect, the present invention provides isolated or recombinant polynucleotides which comprise a smooth muscle myosin heavy chain (SM-MHC) promoter/enhancer sequence capable of conferring smooth muscle specific expression in vivo. In some of the polynucleotides, the promoter sequence consists essentially of a sequence selected from (i) the region of nucleotides 5663 to 5889 of SEQ ID NO:16; (ii) SEQ ID NO:16 except that CArG2 has been mutated; (iii) SEQ ID NO:16 except that the intronic CArG has been mutated; (iv) the regions of nucleotides 1 to 6,700 and nucleotides 9,500 to 15,800 of SEQ ID NO:16; (v) the regions of nucleotides 1 to 9,500 and nucleotides 11,700 to 13,700 of SEQ ID NO:16; (vi) SEQ ID NO:16; and (vii) SEQ ID NO:17.

Some of the polynucleotides hybridize under stringent conditions to the SM-MHC promoter/enhancer. Some of the polynucleotides further comprise a heterologous polynucleotide operably linked to the SM-MHC promoter sequence. Some of the heterologous polynucleotides encode a polypeptide. The polypeptide can be a toxin, a prodrug-converting enzyme, a tumor suppressor, a sensitizing agent, an apoptotic factor, an angiogenesis inhibitor, a cytokine, or an immunogenic antigen. Some of the heterologous polynucleotides consist of an antisense polynucleotide or a catalytic polynucleotide.

In another aspect, the invention provides expression vectors which comprise a smooth muscle myosin heavy chain (SM-MHC) promoter/enhancer sequence that confers smooth muscle specific expression in vivo. Some of the expression vectors are retroviral vectors, adeno-associated viral vectors, or adenoviral vectors. Some of the expression vectors have the promoter sequence operably linked to a heterologous polynucleotide. Some of the expression vectors comprise a promoter which consists essentially of the sequence of SEQ ID NO:16 except that CArG2 or the intronic CArG has been mutated.

In another aspect, the invention provides genetically engineered host cells comprising an expression vector of the invention. Transgenic non-human animals containing the polynucleotides of the invention are also provided. The invention also provides pharmaceutical compositions which comprise the polynucleotides of the invention in a pharmaceutically acceptable carrier.

In still another aspect, the present invention provides methods of expression a polynucleotide in a smooth muscle cell in vivo. The methods entail introducing into the smooth muscle cell the polynucleotide that is operably linked to an SM-MHC promoter/enhancer sequence capable of conferring smooth muscle specific expression in vivo. In some of the methods, the promoter/enhancer consists essentially of (i) the region of nucleotides 5663 to 5889 of SEQ ID NO:16; (ii) SEQ ID NO:16 except that CArG2 has been mutated; (iii) SEQ ID NO:16 except that the intronic CArG has been mutated; (iv) the regions of nucleotides 1 to 6,700 and nucleotides 9,500 to 15,800 of SEQ ID NO:16; (v) the regions of nucleotides 1 to 9,500 and nucleotides 11,700 to 13,700 of SEQ ID NO:16; (vi) SEQ ID NO:16; or (vii) SEQ ID NO:17.

In some methods, the polynucleotide to be expressed is a reporter gene. In some other methods, the polynucleotide to be expressed encodes a therapeutic protein. In some methods, the SM-MHC promoter/enhancer enables expression of the polynucleotide specifically in coronary artery, aorta, airway smooth muscle, or pulmonary vascular smooth muscle. In some methods, the SM-MHC promoter/enhancer enables expression of the polynucleotide specifically in bladder smooth muscle, gastrointestinal tract smooth muscle, or urinary tract smooth muscle. In some other methods, the SM-MHC promoter/enhancer enables expression of the polynucleotide specifically in aorta, pulmonary airway, or pulmonary vascular smooth muscle. In still some other methods, the SM-MHC promoter/enhancer enables expression of the polynucleotide specifically in gastrointestinal tract smooth muscle, urinary tract smooth muscle, airway smooth muscle, vein smooth muscle, or small branching artery smooth muscle. In some methods, the SM-MHC promoter/enhancer enables expression of the polynucleotide specifically in aorta artery smooth muscle, carotid artery smooth muscle, pulmonary artery smooth muscle, vena cava vein smooth muscle, or vascular smooth muscle.

In yet another respect, the invention provides methods for screening compounds that modulate the activity of an SM-MHC promoter/enhancer. The methods entail contacting a test compound with a cell that contains the SM-MHC promoter/enhancer operably linked to a reporter gene; detecting expression of the reporter gene; and comparing the expression thus detected with the amount of expression obtained in the absence of the test compound. If the level obtained in the presence of the test compound is higher or lower than that obtained in the absence of the test compound, a compound that modulates the activity of the SM-MHC promoter/enhancer has been identified.

A further understanding of the nature and advantages of the present invention may be realized by reference to the remaining portions of the specification, the figures and claims.

All publications, GenBank deposited sequences, ATCC deposits, patents and patent applications cited herein are hereby expressly incorporated by reference in their entirety and for all purposes.

BRIEF DESCRIPTION OF THE DRAWINGS

FIG. 4 shows expression of the rat SM-MHC −4.2 to +5.3/+7.5 to +9 promoter LacZ gene in various tissues from adult transgenic mice. As seen, high reporter expression was seen in multiple SMC tissues including the coronary arteries, aorta, airway SMC, and pulmonary vascular SMC (PA-pulmonary artery). The results indicate that this derivative of the SM MHC promoter retains high activity in aortic SMC, pulmonary arterial SMC, and airway SMC.

FIG. 9 shows activity of human SM-MHC promoter of −5.1 to +13.5 region in transgenic mice. Expression of the human MHC−5.1/13.5-LacZ transgene in adult (5–6 weeks old) mouse tissues. Whole tissues were processed and stained for lacZ expression as previously described (Madsen et al. *Circ. Res.* 82:908–917, 1998). Results show that the human promoter has activity virtually identical to that of the rat SM-MHC promoter.

FIG. 10 shows histological evaluation of human MHC−5.1/13 in transgenic mice. Histological examination of specificity of expression of the human MHC−5.1/13.5-LacZ transgene in adult (5–6 weeks old) mouse tissues. Tissues were processed and stained for lacZ expression as previously described (Madsen et al. *Circ. Res.* 82:908–917, 1998).

FIG. 11 shows nucleotide sequence comparison of the rat and human SM-MHC promoter/enhancer sequence within the 5' promoter region. As indicated, there is complete sequence homology between the rat and human genes in the key regulatory regions identified thus far (e.g. 5' CArG 1, 2 and 3; the G/C repressor, etc., as indicated). The identity of these elements in the rabbit and mouse genes have been shown previously. See, Iadsen et al., 1997, *J. Biol. Chem.,* 272:6332.

FIGS. 18A and 18B show mutants with deletions in the intronic CArG element and their promoter activity. (A) A series of 3'-end deletion mutants of the SM-MHC LacZ sequence was generated and assayed for reporter activity in cultured rat SMCs. The β-galactosidase activity of each construct is expressed relative to the activity of the promoterless pAUG LacZ. Error bars show standard error. (B) The nucleotide sequence (+1535 to +1703 from the transcription start site) of a portion of the rat SM-MHC first intron (SEQ ID NO:16) was compared with the corresponding human genomic sequence (GenBank U91323)(SEQ ID NO:17). The intronic CArG element is boxed. Note that the human intronic CArG lacks a G-substitution within the central A/T-rich sequence and perfectly match the CArG consensus (CC(A/T)$_6$GG). Bold letters indicate the region used in 3xICR TK LacZ construct. Nucleotides conserved with the rat sequence are indicated by dashes. Nucleotide additions are indicated by lower-case letters.

DETAILED DESCRIPTION OF THE INVENTION

I. Overview

Figure 1:
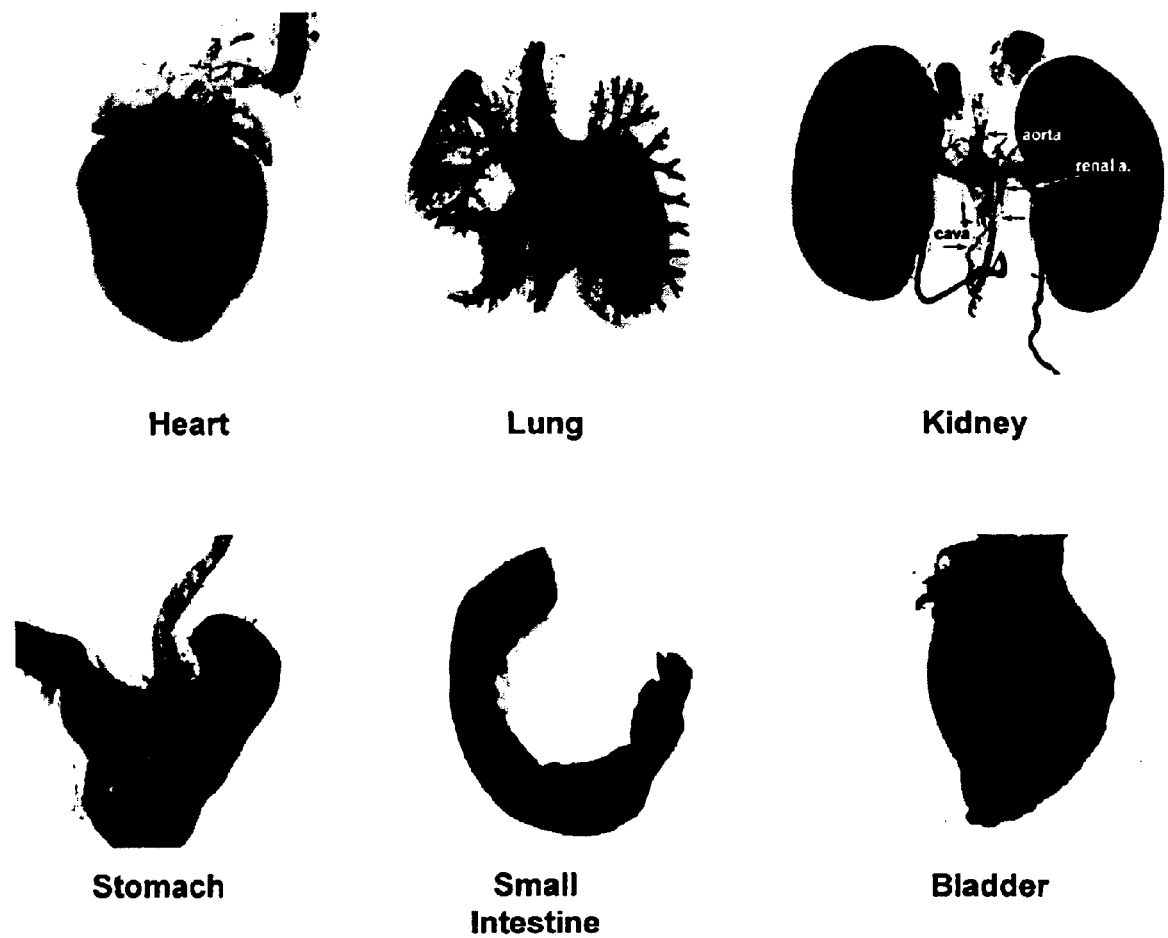
FIG. 1 shows expression of the rat SM-MHC −4.2 to +11.6 promoter-lacZ gene in vivo in adult transgenic mice showing the SMC specificity of the promoter. Extremely high expression was observed in virtually all SMC tissues with no expression in non-SMC (FIG. 3).

The invention provides novel isolated or recombinant polynucleotides comprising cis-acting transcriptional control sequences of smooth muscle (SM) myosin heavy chain (SM-MHC) genes that confer smooth muscle cell (SMC) specific gene expression both in vitro (e.g., in cultured cells) and in vivo (e.g., in human or transgenic animals). The invention also provides polynucleotides and expression vectors comprising SMC specific transcription regulatory elements that are active in only certain subtypes of SM cells. The polynucleotides of the invention include those based on or derived from genomic sequences of untranscribed, transcribed and intronic regions of SM-MHC genes, including the human SM-MHC (hSM-MHC) and rat SM-MHC (rSM-MHC) genes. Prior to the instant invention, no genetic elements that are completely specific for SMC and which have been proven to confer smooth muscle specific gene expression in vivo have been defined, isolated or identified. For example, the previously characterized SMC gene promoters, e.g., SM 22α and SM α-actin promoters, all show activity in both SMC and non-SMC.

The invention also provides methods for using the SM-MHC promoters and other regulatory elements to control the expression of protein and RNA products in SMC. SM-MHC promoters and other regulatory elements have a variety of uses including, but not limited to, expressing heterologous genes in SMC tissues, such as the contractile portion of the stomach, intestine and uterus, the walls of arteries, the ducts of secretory glands and many other regions in which slow and sustained contractions are needed. In addition, the targeted delivery is useful for development of animal models of human disease to assist in development of new therapeutic targets or development of animal models for purpose of screening new drugs/therapies.

Another aspect of the invention relates to the use of SM-MHC promoters and other regulatory elements for genetic engineering as a means to investigate SMC physiology and pathophysiology. For example, a specific gene that is believed to be important for a specific disease within SMC could be knocked out without the confounding influences of knocking out that gene in other cell types and tissues. For example, an antisense polynucleotide could be expressed under the control of an SM-MHC promoter that would inhibit a target gene of interest, or an inhibitor could be expressed that would specifically inhibit a particular protein.

The conventional (non-targeted) methods for gene knockout results in embryonic lethality, thus precluding the utility of studying involvement of these genes in control of SMC differentiation in diseases such as atherosclerosis, hypertension, and asthma. With the methods of the present invention, one could examine how selective (SMC-specific) knockout of an SMC gene of interest affects development of coronary artery disease without the confounding limitations of conventional knockouts with respect to deducing the primary site of action, activation of compensatory pathways, etc. Utilizing the SMC specific expression vectors of the present invention, SMC specific gene knockout can be carried out using methods known in the art. The feasibility of these sorts of approaches has been shown in other non-SMC tissue types (see, e.g., Mayford et al., *Science* 274:1678, 1996). For example, the SM-MHC promoter/enhancers of the instant invention can be used in combination with the tetracycline-cre-recombinase based mouse systems to effectuate targeted knockouts of various genes which are implicated in the control of SMC differentiation within SMC tissues (Hautmann et al., *Circ. Res.* 81:600, 1997; Blank et al., *Circ. Res.* 76:742, 1995; Madsen et al, *J. Biol. Chem.* 272:6332,1997). Examples of such genes include genes which encode for serum response factor (SRF) (Kumar et al., J Biochem, 118: 1285–92, 1995), the homeodomain protein MHox and the retinoic acid α-receptor.

Figure 7:
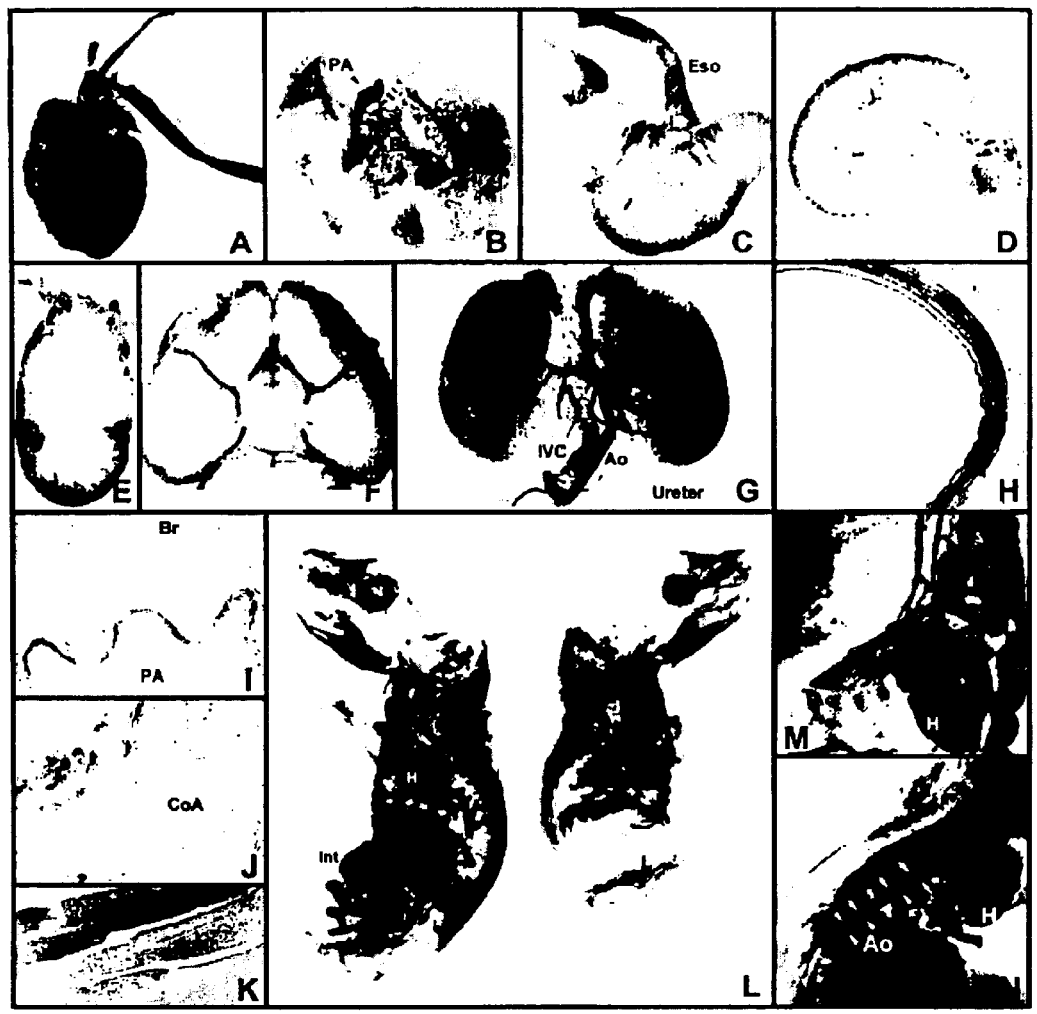
FIG. 7 shows transgene expression of the intronic CArG region-minimal TK-LacZ. Various tissues of 4-week-old transgenic mice and embryos of the 3xICR-TK LacZ line (7240) were stained for β-galactosidase activity. A–B: anterior view of the heart and lung; C: the esophagus, stomach, and duodenum; D: a part of small intestine; E: the bladder; F: bottom view of the brain; G: anterior view of abdominal organs and great blood vessels; H–K: histological examination of the thoracic aorta (H), pulmonary artery and bronchus (I), cardiac muscle and coronary artery (J), and intercostal muscle (K) of the 3xICR-TK LacZ transgenic mice; L–M: transgene expression in a 19.5-dpc embryo of the 3xICR-TK LacZ line. The embryo was skinned, sectioned sagittally along the midline, stained, and cleared; N: transgene expression in the heart and aorta of a 16.5-dpc embryo. Ao indicates aorta; PA, pulmonary artery; SMA, superior mesenteric artery; IVC, inferior vena cava; H, heart; Br, bronchus; Eso, esophagus; Int, intestine; S, stomach; Bl, bladder. The results indicate that a very small derivative of the promoter is capable of driving high level expression in SMC in vivo.
Figure 8:
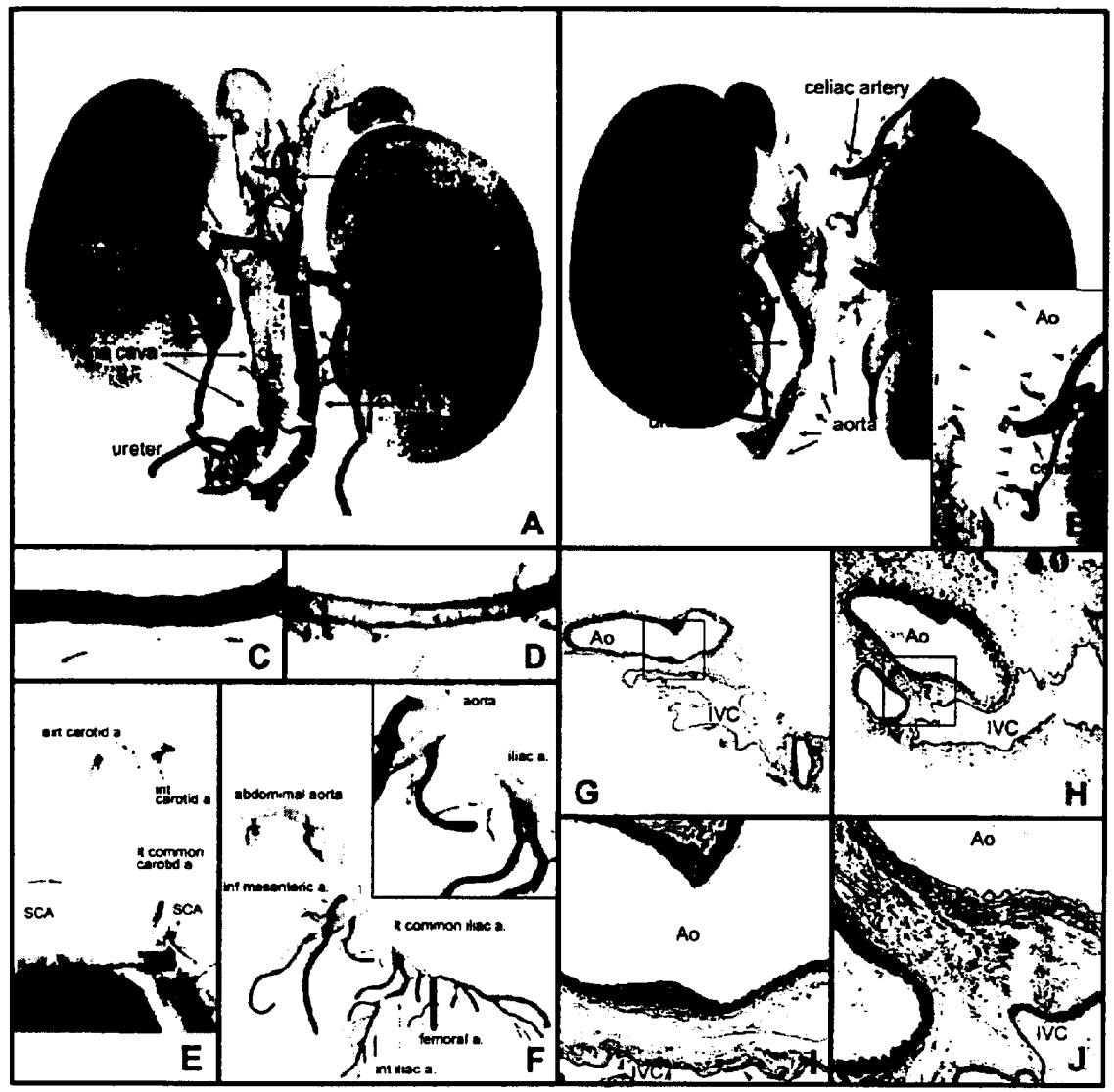
FIG. 8 shows the effects of mutation of the intronic CArG on expression of the rat −4.2 to +11.6 SM-MHC transgene in vivo. Abdominal organs were removed en block showing reporter expression in the blood vessels and urinary tract in the wild-type (A) and intronic CArG mutant (B) transgenic mice. To better illustrate transgene expression in large arteries, several smaller arteries and connective tissues were removed and the tissues cleared. The supramesenteric artery, which was stained positive, was removed from the intronic CArG mutant mouse tissues. A portion of the tissues is expanded in the insert in panel B. Arrowheads indicate the position of aorta that is not visible because of the lack of staining. Note that the blood vessels within the kidneys were not stained in either wild-type nor intronic CArG mutants. C, D, the thoracic aorta and branching arteries of the wild-type (C) and the intronic CArG (D) mutant transgenic mice. E, view of the large arteries in the cervicothoracic region of the intronic CArG mutant transgenic mouse. F, the large arteries and their branches in the abdomen of the intronic CArG mutant. A portion of the arteries is expanded in the insert in F. G, H, I, J, histological examination of the abdominal aorta and inferior vena cava of the wild-type (G, I) and the intronic CArG mutant (H, J) mice showing abrogation of reporter expression in SMCs of the aorta in the intronic CArG mutants. Note that expression in the vena cava was not changed by the mutation. The boxed areas (G, H) are shown by a higher magnification (I, J). Ao indicates aorta; DA, ductus arteriosus; IVC, inferior vena cava; SCA, subclavian artery. The results indicate that this mutation selectively abolished activity in large blood vessels such as the aorta, carotid, and coronary outflow tracts without altering expression in smaller arteries and arterioles.

A major biomedical application of the methods for SMC targeted gene delivery is to use the SM-MHC regulatory region to over-express a gene of interest within SMC. For example, an inhibitor of a pathologic process within an SMC tissue may be over-expressed in order to generate a high, local concentration of the factor that might be needed for a therapeutic effect. Since expression of the gene would be SMC-specific, undesired side effects on other tissues that often result when conventional systemic administration of therapeutic agents are utilized would be avoided. For example, a gene for an SMC relaxant could be over-expressed within bronchiolar SMC as a therapy for asthma, or an inhibitor of SMC growth could be over-expressed to prevent development of atherosclerosis or post-angioplasty restinosis. Such applications of the present invention is exemplified in various embodiments disclosed herein. For example, FIG. 7 shows that a transgene under the control of an SM-MHC promoter was specifically expressed at high levels within all coronary arteries and arterioles within the heart of an adult mouse, demonstrating efficacy of the SM-MHC promoter/enhancer for gene therapy for coronary artery disease.

The present invention also provides SM-MHC promoter/enhancers that retain high level SMC specific expression in vivo and are selectively active in subsets of SMC. Expression vectors containing such promoters have tremendous utility for targeting gene expression to specific subtypes of smooth muscle in vivo. For example, these vectors can be employed in targeting expression of a therapeutic gene to the specific subtype of SMC desired (e.g. bronchiolar SMC for treatment of asthma or chronic bronchitis) thereby increasing the efficacy of the therapy and reducing potential side effects due to over-expression in undesired tissues and cells. Efficacy of such applications of the present invention is demonstrated in, e.g., FIGS. 4–6 and 8, which showed that some SM-MHC promoters exhibit very high activity in subsets of SMC without loss of cell specificity.

Moreover, the SM specific promoter/enhancers sequences and expression vectors of the present invention can also be employed in identification and/or selection of smooth muscle cells derived from multi-potential stem cell populations for purposes of tissue generation/regeneration for surgery (e.g. for blood vessel, bladder, or gastrointestinal smooth muscle tissue augmentation-reconstitution), and/or as a means of delivering a therapeutic gene to SMC tissues in vivo (as described in U.S. Provisional Application No. 60/277,202). The latter involves (i) introduction of a therapeutic gene into stem cells derived from a subject's bone marrow, adipose tissue or cryo-preserved umbilical vessels; (ii) isolation and purification of SMC populations from multi-potential stem cells using the SM-MHC promoter derivatives described herein to drive expression of drug selectable markers such as puromycin; and (iii) surgical introduction of the stem-cell-derived SMC into the desired site of action in vivo.

A number of advantages are provided by the targeting methods of present invention. For example, SMC targeting will permit attainment of higher local concentrations of a therapeutic gene/agent at the desired site of action (i.e., SMC) than possible with systemic delivery methods, thus resulting in a greater therapeutic benefit and fewer possible side effects. In addition, SMC targeted gene therapy systems are much safer than simple "restricted assess" gene delivery based methods that employ constitutively-active viral promoters, because the latter involve potential accidental delivery of a therapeutic gene to an unintended tissue or cell type may result in major undesirable side effects and possible death. By contrast, an SMC specific promoter based targeting system is superior in that even if the therapeutic gene is delivered to an undesired cell type, it will not be expressed.

The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). Although any methods and materials similar or equivalent to those described herein can be used in the practice or testing of the present invention, the preferred methods and materials are described. The following definitions are provided to assist the reader in the practice of the invention.

The terms "allele" or "allelic sequence" refer to an alternative form of a polynucleotide sequence. Alleles result from mutations (i.e., changes in the polynucleotide sequence), and can produce differently regulated mRNAs. Common mutational changes that give rise to alleles are generally ascribed to natural deletions, additions, or substitutions of nucleotides. Each of these types of changes may occur alone, in combination with the others, or one or more times within a given gene, chromosome or other cellular polynucleotide.

The term "amplifying" incorporates its common usage and refers to the use of any suitable amplification methodology for generating or detecting recombinant or naturally expressed polynucleotide, as described in detail, below. For example, the invention provides methods and reagents (e.g., specific oligonucleotide PCR primer pairs) for amplifying (e.g., by PCR) naturally expressed or recombinant polynucleotides of the invention (e.g., SM-MHC promoter/enhancer sequences) in vivo or in vitro. An indication that two polynucleotides are "substantially identical" can be obtained by amplifying one of the polynucleotides with a pair of oligonucleotide primers or pool of degenerate primers (e.g., fragments of an SM-MHC promoter/enhancer sequence) and then using the product as a probe under stringent hybridization conditions to isolate the second sequence (e.g., the SM-MHC promoter/enhancer sequence) from a genomic library or to identify the second sequence in, e.g., a Northern or Southern blot.

A polynucleotide is "expressed" when a DNA copy of the polynucleotide is transcribed into RNA.

An "expression vector" is a polynucleotide construct, generated recombinantly or synthetically, with a series of specified polynucleotide elements that permit transcription of a particular polynucleotide in a host cell. The expression vector can be part of a plasmid, virus, or polynucleotide fragment. Typically, the expression vector includes a polynucleotide to be transcribed operably linked to a promoter.

The term "heterologous" when used with reference to portions of a polynucleotide, indicates that the polynucleotide comprises two or more subsequences which are not found in the same relationship to each other in nature. For instance, the polynucleotide is typically recombinantly produced, having two or more sequences from unrelated genes arranged in a manner not found in nature; e.g., an SM-MHC promoter sequence of the invention operably linked to a polypeptide coding sequence that are not transcribed from the SM-MHC genomic locus. For example, the invention provides recombinant constructs (expression cassettes, vectors, viruses, and the like) comprising various combinations of promoters of the invention, or subsequences thereof, and heterologous coding sequences, many examples of which are described in detail below.

The terms "identical" or percent "identity," in the context of two or more polynucleotides or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement of a sequence. For example, in alternative embodiments, polynucleotides within the scope of the invention include those with a nucleotide sequence identity that is at least about 60%, at least about 75–80%, about 90%, and about 95% of the exemplary SM-MHC promoter/enhancer sequence set forth in SEQ ID NO:16 or SEQ ID NO:17, and the intronic SM-MHC sequences capable of driving a reporter gene in SM cells, as described below. Two sequences with these levels of identity are "substantially identical." Thus, if a sequence has the requisite sequence identity to an SM-MHC promoter/enhancer sequence or subsequence of the invention, it also is an SM-MHC promoter/enhancer sequence within the scope of the invention.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence (e.g., an SM-MHC promoter/enhancer sequence of the invention as set forth by. e.g., SEQ ID NO:16 or SEQ ID NO:17) is compared to another sequence to determine the percent sequence identity relationship (i.e., that the second sequence is substantially identical and within the scope of the invention) using the following parameters: default gap weight (3.00), default gap length weight (0.10), and weighted end gaps. PILEUP can be obtained from the GCG sequence analysis software package, e.g., version 7.0 (Devereaux (1984) Nuc. Acids Res. 12:387–395).

Another example of algorithm that is suitable for determining percent sequence identity (i.e., substantial similarity or identity) is the BLAST algorithm, which is described in Altschul (1990) J. Mol. Biol. 215:403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues, always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a polynucleotide sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff (1989) Proc. Natl. Acad. Sci. USA 89:10915).

The BLAST algorithm also performs a statistical analysis of the similarity between two sequences (see, e.g., Karlin (1993) Proc. Nat'l. Acad. Sci. USA 90:5873–5787). One measure of similarity provided by the BLAST algorithm is the smallest sum probability (P(N)), which provides an indication of the probability by which a match between two nucleotide or amino acid sequences would occur by chance. For example, a polynucleotide is considered similar to a reference sequence if the smallest sum probability in a comparison of the test polynucleotide to the reference polynucleotide is less than about 0.1, more preferably less than about 0.01, and most preferably less than about 0.001.

The term "isolated," when referring to a molecule or composition, such as, e.g., an SM-MHC promoter/enhancer sequence, means that the molecule or composition is separated from at least one other compound, such as a protein, DNA, RNA, or other contaminants with which it is associated in vivo or in its naturally occurring state. Thus, a polynucleotide sequence is considered isolated when it has been isolated from any other component with which it is naturally associated. An isolated composition can, however, also be substantially pure. An isolated composition can be in a homogeneous state. It can be in a dry or an aqueous solution. Purity and homogeneity can be determined, e.g., using analytical chemistry techniques such as, e.g., polyacrylamide gel electrophoresis (PAGE), agarose gel electrophoresis or high pressure liquid chromatography (HPLC).

The term "modulate" refers to the suppression, enhancement or induction of a function. For example, an agent or compound may modulate an SM-MHC promoter/enhancer sequence by binding to a motif within the promoter/enhancer, thereby enhancing or suppressing transcription of a gene operably linked to the promoter/enhancer. Alternatively, modulation may include inhibition of transcription of a gene where the an agent or compound binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a mRNA transcript.

The terms "nucleic acid" and "polynucleotide" are used interchangeably, and include oligonucleotides (i.e., short polynucleotides). They also refer to synthetic and/or non-naturally occurring polynucleotides (i.e., comprising polynucleotide analogues or modified backbone residues or linkages). The terms also refer to deoxyribonucleotide or ribonucleotide oligonucleotides in either single-or double-stranded form. The terms encompass polynucleotides containing known analogues of natural nucleotides. The term also encompasses polynucleotide-like structures with synthetic backbones. DNA backbone analogues provided by the invention include phosphodiester, phosphorothioate, phosphorodithioate, methyl-phosphonate, phosphoramidate, alkyl phosphotriester, sulfamate, 3'-thioacetal, methylene (methylimino), 3'-N-carbamate, morpholino carbamate, and peptide polynucleotides (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl)glycine units. Phosphorothioate linkages are described in WO 97/03211; WO 96/39154; Mata (1997) Toxicol. Appl. Pharmacol. 144:189–197. Other synthetic backbones encompassed by the term include methyl-phosphonate linkages or alternating methylphosphonate and phosphodiester linkages (Strauss-Soukup (1997) Biochemistry 36:8692–8698), and benzyl-phosphonate linkages (Samstag (1996) Antisense Nucleic Acid Drug Dev 6:153–156).

The term "operably linked" refers to a functional relationship between two or more polynucleotide (e.g., DNA) segments. Typically, it refers to the functional relationship of a transcriptional regulatory sequence to a transcribed sequence. For example, an SM-MHC promoter/enhancer sequence of the invention, including any combination of cis-acting transcriptional control elements, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. A polylinker provides a convenient location for inserting coding sequences so the genes are operably linked to the SM-MHC promoter. Polylinkers are polynucleotide sequences that comprise a series of three or more closely spaced restriction endonuclease recognition sequences.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RINA molecule serves as a template for synthesis of a specific protein; sometimes RNA itself is the final product. The promoter region may be a normal cellular promoter or an oncopromoter.

The term "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of polynucleotides having coding or promoter sequences from different sources into an expression cassette or vector for expression of, e.g., a fusion protein; or, inducible, constitutive expression of a protein (i.e., an SM-MHC promoter/enhancer of the invention operably linked to a heterologous nucleotide, such as a polypeptide coding sequence).

The "sequence" of a gene (unless specifically stated otherwise) or polynucleotide refers to the order of nucleotides in the polynucleotide, including either or both strands of a double-stranded DNA molecule, e.g., the sequence of both the coding strand and its complement, or of a single-stranded polynucleotide molecule. For example, the promoter of the invention comprises untranscribed, untranslated, and intronic SM-MHC sequences, e.g., as set forth in the exemplary SEQ ID NO:16 and SEQ ID NO:17.

Unless otherwise specified, the term "SM-MHC" broadly refers to smooth muscle myosin heavy chain, as well as the corresponding polynucleotide and polypeptide sequences. See White et al., J. Biol. Chem. 27115008–15017, 1996.

Unless otherwise specified, the terms "SM-MHC promoter," "SM-MHC promoter/enhancer" and "SM-MHC promoter/enhancer sequence" are used interchangeably and refer to a polynucleotide which comprises SM-MHC genomic sequence and activates transcription of a linked polynucleotide in smooth muscle cells in vitro and in vivo. Unless otherwise noted, the SM-MHC promoter/enhancers of the present invention do not include a polynucleotide which can drive DNA expression in cultured SMCs, but not in an animal having a smooth muscles (e.g., transgenic mice). The SM-MHC promoter/enhancer sequences can include all cis-acting SM-MHC transcriptional control elements and regulatory sequences, including (without limitation) those that regulate and modulate timing and rates of transcription. Thus, the SM-MHC promoter/enhancer sequences of the invention can include cis-acting elements such as, e.g., promoters, enhancers, transcription terminators, origins of replication, chromosomal integration sequences, introns, exons, and 5' and 3' untranslated regions, with which proteins or other biomolecules interact to carry out and regulate transcription of the SM-MHC transcript.

The term "smooth muscle-specific expression" or "smooth muscle-specific transcription" means that a polynucleotide is transcribed at a greater rate in smooth muscle cells than in non-smooth muscle cells. Exemplary SM cells include cells which form the contractile portion of the stomach, intestine and uterus, the walls of arteries, the ducts of secretory glands and many other regions in which slow and sustained contractions are needed. In general, an SM specific promoter and/or enhancer will generally activate transcription of a linked polynucleotide at least 3-fold more efficiently in SM cells than in non-SM cells. In certain embodiments, transcription is at least 3-fold, 5-fold, 10-fold, 25-fold or 100-fold more efficient in SM cells than in non-SM cells. Unless otherwise specified, SM-MHC promoter/enhancers of the present invention do not have detectable activity in non-SM cells when examined using a reporter gene (e.g., lacZ) as described in the Examples. SM-specific transcription may result from an increased frequency of transcriptional initiation, an increased rate of transcriptional elongation, a decreased frequency of transcriptional termination, or a combination thereof.

The phrase "selectively (or specifically) hybridizes to" refers to the binding, duplexing, or hybridizing of a molecule to a particular nucleotide sequence under moderately or highly stringent hybridization conditions when that sequence is present in a complex mixture (e.g., total cellular or library DNA or RNA), wherein the particular nucleotide sequence is detected at least twice background, preferably 10 times background. In one embodiment, a polynucleotide can be determined to be within the scope of the invention (e.g., is substantially identical to an SM-MHC promoter/enhancer of the invention, as exemplified by SEQ ID NO:16 or SEQ ID NO:17, or, by an intronic promoter sequence, as described below) by its ability to hybridize under stringent conditions to another polynucleotide (such as the exemplary sequences described herein).

The phrase "stringent hybridization conditions" refers to conditions under which a probe will primarily hybridize to its target subsequence, typically in a complex mixture of polynucleotide, but to no other sequences. Stringent conditions are sequence-dependent and will be different in different circumstances, e.g., depending on the length of the probe. Longer sequences hybridize specifically at higher temperatures. An extensive guide to the hybridization of polynucleotides is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to about 50 nucleotides) and at least about 60° C. for long probes (e.g., greater than about 50 nucleotides). Stringent conditions may also be achieved with the addition of destabilizing agents such as formamide. For selective or specific hybridization, a positive signal (e.g., identification of a polynucleotide of the invention) is about 5–10 times background hybridization. "Stringent" hybridization conditions that are used to identify substantially identical polynucleotides within the scope of the invention include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C., for long probes. For short probes, stringent hybridization conditions include hybridization in a buffer comprising 50% formamide, 5×SSC and 1% SDS at room temperature or hybridization in a buffer comprising 5×SSC and 1% SDS at 37° C.–42° C., both with a wash of 0.2×SSC and 0.1% SDS at 37° C.–42° C. However, as is apparent to one of ordinary skill in the art, hybridization conditions can be modified depending on sequence composition. Exemplary "moderately stringent hybridization conditions" include a hybridization in a buffer of 40% formamide, 1 M NaCl, and 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Transcription initiation elements" refer to sequences in a promoter that specify the start site of RNA polymerase II. Transcription initiation elements may include TATA boxes, which direct initiation of transcription 25–35 bases downstream, or initiator elements, which are sequences located near the transcription start site itself. Eukaryotic promoters generally comprise transcription initiation elements and either promoter-proximal elements, distant enhancer elements, or both. SM-MHC transcription initiation elements may include the TATA box or transcription initiation sites described herein, or both. Heterologous transcription initiation elements may be obtained from any eukaryotic promoter, although mammalian and viral promoters are preferred sources of heterologous initiation elements.

The term "transcribable sequence" refers to any sequence which, when operably linked to a cis-acting transcriptional control element, e.g., a promoter, such as the SM-MHC promoter/enhancers of the invention, and when placed in the appropriate conditions, is capable of being transcribed to generate RNA, e.g., messenger RNA (mRNA).

III. Polynucleotides Comprising Smooth Muscle Specific Promoter/Enhancers

The present invention provides polynucleotide sequences which confer to an operably linked polynucleotide cell-specific expression within SM cells in vivo. These polynucleotide sequences, termed SM-MHC promoter/enhancers, are derived from the smooth muscle myosin heavy chain (SM-MHC) gene. Some of the SM-MHC promoter/enhancers are obtained from the human SM-MHC sequence (e.g., SEQ ID NO:17). SEQ ID NO:17 contains residues −5086 to +13,518 of the human SM-MHC gene sequence. Nucleotide 1 in SEQ ID NO:17 corresponds to position −5086 relative to the transcription start site (+1 position) which in turn corresponds to position 143,590 in the undefined BAC sequence contained in the public database (GenBank Accession No. U91323). Some of the SM-MHC promoter/enhancers are derived from rat SM-MHC sequence (e.g., SEQ ID NO:16). Nucleotide 1 of SEQ ID NO:16 corresponds to position −4,216 bp relative to the SM-MHC transcription start site.

The present invention also provides SM specific promoter/enhancers which are active only in certain subsets of smooth muscle tissues. Some of these SM-MHC promoter/enhancers comprise a polynucleotide sequence which consists essentially of the region of nucleotides 5663 to 5889 of SEQ ID NO:16 (the +1447 to +1673 intronic region). Other comprise a sequence of SEQ ID NO:16 except that the CArG2 or the intronic CArG motif has been mutated. Some of the promoter/enhancers comprise a polynucleotide sequence which consists essentially of the regions of nucleotides 1 to 6,700 (the −4.2 to +2.5 region) and nucleotides 9,500 to 15,800 (the +5.3 to +11.6 region) of SEQ ID NO:16. Some of the subset-specific SM-MHC promoter/enhancers comprise a polynucleotide sequence which consists essentially of the regions of nucleotides 1 to 9,500 (the −4.2 to +5.3 region) and nucleotides 11,700 to 13,700 (the +7.5 to +9.5 region) of SEQ ID NO:16.

In alternative embodiments, the SM-MHC promoter/enhancer sequences comprise sequences substantially identical to an exemplary SM-MHC promoter/enhancer sequence as discussed above. Thus, SM-MHC promoters/enhancers of the instant invention include homologous SMC promoter/enhancer elements which have similar functional activity. This includes SMC promoters/enhancers which direct SMC-specific expression in vivo and either hybridize to the above-described SM-MHC promoter/enhancers under highly stringent conditions, or that hybridize to the complement of the above-described promoter/enhancers under moderately stringent conditions.

SM-MHC promoter/enhancer sequences can range from 100 to 20,000 nucleotides in length, although in particular embodiments functional SM-MHC promoter/enhancer polynucleotides may be at least or no more than about 300, 500, 1,000, 2,500, 5,000, 10,000, or 15,000 nucleotides in length. SM-MHC promoter/enhancer polynucleotides of the present invention are generally at least 70% homologous to SEQ ID NO:16 or SEQ ID NO:17 over a stretch of 150 nucleotides or more. In some embodiments, SM-MHC promoter/enhancer polynucleotides are at least 75%, 80%, 85%, 90%, 92%, 95%, or 100% homologous to SEQ ID NO:16 or SEQ ID NO:17 over a stretch of 300, 500, 1,000, 2,500, 5,000, 10,000 or 15,000 nucleotides.

As detailed in the Examples, some of the SM-MHC promoter/enhancer sequences comprise non-transcribed SM-MHC genomic sequence as well as either SM-MHC introns or exons, or both. In some embodiments, SM-MHC promoter/enhancer polynucleotides include the SM-MHC TATA box and transcription initiation sites (collectively referred to as SM-MHC transcription initiation elements). In embodiments where the SM-MHC transcription initiation elements are the only functional initiation elements of the promoter, the natural orientation of the SM-MHC TATA box or transcription initiation sites, relative to the direction of transcription, should be preserved. In other embodiments, SM-MHC promoter/enhancer polynucleotides are connected to heterologous TATA boxes and/or transcription initiation sites. When linked to heterologous TATA boxes or transcription initiation sites, SM-MHC promoter/enhancer polynucleotides act as enhancer elements and may be inserted in either orientation relative to the direction of transcription. Thus, the term "SM-MHC promoter/enhancer" encompasses polynucleotides comprising the transcription initiation elements of the SM-MHC gene, as well as cis-linked enhancer sequences that yield smooth muscle-specific expression when linked to the transcription initiation elements of a heterologous gene.

A. Isolation of SM Specific Promoter/Enhancer Sequences

1. Isolation of SM-MHC Promoter Sequences

The SM-MHC promoter/enhancer sequences of the invention and polynucleotides used to practice this invention, whether RNA, cDNA, genomic DNA, or hybrids thereof, may be isolated from a variety of sources, genetically engineered, amplified, and/or expressed recombinantly. Any recombinant expression system can be used, including, e.g., bacterial, yeast, insect or mammalian systems. Alternatively, these polynucleotides can be chemically synthesized in vitro.

In some embodiments, SM-MHC promoter sequences are isolated from libraries of genomic DNA. Some genomic libraries are commercially available. For example, rat genomic phage library can be obtained from Stratagene Corp. Genomic DNA libraries are also available from various other commercial suppliers (e.g., Incyte Genomics, Palo Alto, Calif.; Clontech, Palo Alto, Calif.). Alternatively, genomic libraries can also be constructed, e.g., as described in Ausubel et al., supra. For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

In some embodiments, the SM-MHC promoter/enhancer sequences are obtained from genomic clones containing 5' flanking region and the intronic regions of the SM-MHC gene. Standard methods that may used in such screening include, for example, the method set forth in Benton & Davis, 1977, *Science* 196:180 for bacteriophage libraries; and Grunstein & Hogness, 1975, *Proc. Nat. Acad. Sci. U.S.A.* 72:3961–3965 for plasmid libraries.

SM-MHC promoter polymorphic variants, orthologs, and alleles that are substantially identical to SM-MHC promoter sequences can be isolated using SM-MHC promoter/enhancer polynucleotide probes and oligonucleotides under stringent hybridization conditions, by screening libraries from the appropriate organism.

Techniques for the manipulation of polynucleotides, such as, e.g., subcloning into expression vectors, labeling probes, sequencing, and hybridization are well described in the scientific and patent literature, see e.g., ed., Molecular Cloning: A Laboratory Manual (2nd Ed.), Vols. 1–3, Cold Spring Harbor Laboratory, (1989) ("Sambrook"); Current Protocols In Molecular Biology, Ausubel, ed. John Wiley & Sons, Inc., New York (1997) ("Ausubel"); Laboratory Techniques In Biochemistry And Molecular Biology: Hybridization With Nucleic Acid Probes, Part I. Theory and Nucleic Acid Preparation, Tijssen, ed. Elsevier, N.Y. (1993) ("Tijssen"). Nucleic acids can be analyzed and quantified by any of a number of general means well known to those of skill in the art. These include, e.g., analytical biochemical methods such as NMR, spectrophotometry, radiography, electrophoresis, capillary electrophoresis, high pressure liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other polynucleotide or target or signal amplification methods, radiolabeling, scintillation counting, and affinity chromatography.

Oligonucleotides that are not commercially or publicly available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

Synthetic oligonucleotides can be also used to construct recombinant SM-MHC promoter sequences for use as probes or for generation of smooth muscle-specific promoters. This method is performed using a series of overlapping oligonucleotides usually 40–120 bp in length, representing both the sense and non-sense (antisense) strands of the gene. These DNA fragments are then annealed, ligated and cloned. Alternatively, amplification techniques can be used with precise primers to amplify a specific subsequence of an SM-MHC promoter sequence.

SM-MHC promoter sequences are typically cloned into intermediate vectors before transformation into prokaryotic or eukaryotic cells for replication and/or expression. These intermediate vectors are typically prokaryotic vectors, e.g., plasmids, or shuttle vectors.

2. Modification of SM-MHC Promoter Sequences

Once smooth muscle-specific transcriptional activity has been demonstrated in an SM-MHC promoter/enhancer sequence, deletions, mutations, rearrangements, and other sequence modifications may be constructed and analyzed for smooth muscle-specific transcription. Such derivatives of SM-MHC promoter sequences are useful to generate more compact promoters, to decrease background expression in non-smooth muscle cells, to eliminate repressive sequences, or to identify novel smooth muscle-specific transcriptional regulatory proteins.

SM-MHC promoter subfragments and derivatives may be constructed by conventional recombinant DNA methods known in the art. One such method is to generate a series of deletion derivatives within the promoter sequence (see, e.g., FIG. 18A and Example 2). By comparing the transcriptional activity of a deletion series, the elements that contribute to or detract from smooth muscle-specific transcription may be localized. Based on such analyses, improved derivatives of SM-MHC promoter sequences may be designed. SM-MHC promoter elements may be combined with smooth muscle-specific or ubiquitous regulatory elements from heterologous promoters to increase the specificity or activity of an SM-MHC promoter sequence.

The modified SM-MHC promoter/enhancer sequences can contain deletion in one or more of the cis-acting elements. Cis-acting regulatory elements within a promoter/enhancer may be identified using methods such as DNase or chemical footprinting (e.g. Meier et al., 1991, *Plant Cell* 3:309–315) or gel retardation (e.g., Weissenbom & Larson, 1992, *J. Biol. Chem.* 267-6122–6131; Beato, 1989, *Cell* 56:335–344; Johnson et al., 1989, *Ann. Rev. Biochem.* 58:799–839). Additionally, resectioning experiments also may be employed to define the location of the cis-regulatory elements. For example, a promoter/enhancer containing fragment may be resected from either the 5' or 3' end using restriction enzyme or exonuclease digests.

In addition, specific base pairs can be modified to alter, increase or decrease the binding affinity to trans-acting transcriptional regulatory factors, thus modifying the relative level of transcriptional activation or repression. Modifications can also change secondary structures of specific subsequences, such as those associated with many cis-acting transcriptional elements. Site-specific mutations can be introduced into polynucleotides by a variety of conventional techniques, well described in the scientific and patent literature. Illustrative examples include, e.g., site-directed mutagenesis by overlap extension polymerase chain reaction (OE-PCR), as described in Urban (1997) Nucleic Acids Res. 25:2227–2228; Ke (1997) Nucleic Acids Res 25:3371–3372, and Chattopadhyay (1997) Biotechniques 22:1054–1056. Modified SM-MHC promoter/enhancer sequences of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896.

B. Activity of SM-MHC Promoter/Enhancers

The present invention provides smooth muscle-specific SM-MHC promoters and enhancers. Accordingly, methods for assaying the smooth muscle-specific transcription induced by SM-MHC promoter sequences are provided herein.

Promoter activity of an SM-MHC promoter sequence is generally assayed by operably linking the SM-MHC promoter sequence to a reporter gene (e.g., a lacZ gene) in a test construct (see, e.g., Example 1, infra). When inserted into the appropriate host cell (e.g., cultured rat SM cells), the SM-MHC promoter sequence induces transcription of the reporter gene by host RNA polymerases. Reporter genes typically encode proteins (e.g., β-galactosidase) with an easily assayed enzymatic activity that is naturally absent from the host cell. Alternatively, endogenous activity of the reporter protein can be measured with a control construct which does not express the reporter gene, and substracted from the activity measured for the test construct. In addition to β-galactosidase, other reporter proteins that can be applied in the present invention include chloramphenicol acetyltransferase (CAT), firefly or *Renilla* luciferase, β-galactosidase, beta-glucuronidase, alkaline phosphatase, and green fluorescent protein (GFP). In some embodiments, SM-MHC promoter fragments can be inserted into a polylinker sequence and tested for activity of the reporter protein in the appropriate host cell (see, e.g., U.S. Pat. No. 5,670,356).

Transcription driven by SM-MHC promoter sequences can also be detected by directly measuring the amount of RNA transcribed from the reporter gene. In these embodiments, the reporter gene can be any transcribable polynucleotide of known sequence that is not otherwise expressed by the host cell. RNA expressed from SM-MHC promoter constructs may be analyzed by techniques known in the art, e.g., reverse transcription and amplification of MRNA, isolation of total RNA or poly $A^+$ RNA, northern blotting, dot blotting, in situ hybridization, RNase protection, primer extension, high density polynucleotide array technology and the like.

In addition to reporter genes, vectors for assaying SM-MHC promoter sequence activity also comprise elements necessary for propagation or maintenance in the host cell, and elements such as polyadenylation sequences and transcriptional terminators to increase expression of reporter genes or prevent cryptic transcriptional initiation elsewhere in the vector. Assay vectors may also comprise other transcription regulatory (e.g., transcription initiation) sequences, depending on whether the SM-MHC transcription initiation elements are included in the SM-MHC promoter sequence being assayed.

1. Assaying Activity of SM-MHC Promoter/Enhancers SM Cells

The ability of a promoter sequence to activate transcription can be assessed relative to a control construct which harbors a reference promoter. In some embodiments, the specificity of an SM-MHC promoter sequence to activate transcription is assessed by comparing the expression of a reporter gene operably linked to an SM-MHC promoter sequence with the expression of the identical reporter gene operably linked to a reference promoter. For example, the activity of a reporter gene driven by an SM-MHC promoter sequence can be compared to the activity of a reporter gene driven by a characterized promoter (e.g., the SV40 promoter/enhancer, Promega, Madison, Wis.).

SM-MHC promoter sequences of the present invention are smooth muscle-specific, activating transcription to a greater extent in smooth muscle cells than in non-smooth muscle cells. Accordingly, smooth muscle specificity of an SM-MHC promoter sequence may be assessed by assaying its promoter or enhancer activity in a smooth muscle cell and a non-smooth muscle cell. In some embodiments, the assay for smooth muscle-specific promoter activity generally requires simultaneous comparison of reporter gene expression in four contexts: the test promoter in a smooth muscle cell, a reference promoter (e.g., lacking SM-MHC sequences) in the smooth muscle cell, the test promoter in a non-smooth muscle cell, and the reference promoter in a non-smooth muscle cell. Once the promoter activity of the SM-MHC polynucleotide in each cell type is determined by comparing the test promoter and the reference promoter, the smooth muscle specificity of the SM-MHC polynucleotide is calculated by comparing the activity of the test promoter in the smooth muscle cell with its activity in a non-smooth muscle cell.

One system for assessing SM-MHC promoter activity is transient or stable transfection into cultured cell lines. Assay vectors bearing SM-MHC promoter sequences operably linked to reporter genes can be transfected into any mammalian cell line for assays of promoter activity. Suitable methods of cell culture, transfection, and reporter gene assay are described in, e.g., Ausubel et al., supra; or *Transfection Guide*, Promega Corporation, Madison, Wis. (1998). SM-MHC promoter sequences may be assayed for smooth muscle-specific transcription activity by transfecting the assay vectors in parallel into smooth muscle cell lines and non-smooth muscle cell lines. In some embodiments, a control vector comprising a second reporter gene driven by a known promoter (e.g., *Renilla* luciferase driven by the SV40 early promoter/enhancer; pRL-SV40, Promega, Madison, Wis.) is co-transfected along with the assay vector to control for variations in transfection efficiency or reporter gene translation among the smooth muscle and non-smooth muscle cell lines.

2. Assaying In Vivo Activity of the SM-MHC Promoter/Enhancers

As disclosed above, the activity of specificity of the SM-MHC promoter/enhancers of the present invention can be assayed in eukaryotic in vitro transcription systems (e.g., cultured rat SM cells). Their activity can also be examined in transgenic animals (e.g., transgenic mice). Further, it is known that some promoter or enhancers with specificity in cultured SM cells do not have activity in vivo, e.g., in transgenic mice. Thus, to determine in vivo specificity, the SM-MHC promoter/enhancers are also assayed for their activity in transgenic animals.

Transgenic animals (e.g., transgenic mice) expressing SM-MHC promoter/enhancer can be generated accordingly to methods well known in the art (see, e.g., Example 1). For example, techniques routinely used to create and screen for transgenic animals have been described in, e.g., see Bijvoet (1998) Hum. Mol. Genet. 7:53–62; Moreadith (1997) J. Mol. Med. 75:208–216; Tojo (1995) Cytotechnology 19:161–165; Mudgett (1995) Methods Mol. Biol. 48:167–184; Longo (1997) Transgenic Res. 6:321–328; U.S. Pat. No. 5,616,491 (Mak, et al.); U.S. Pat Nos. 5,464, 764; 5,631,153; 5,487,992; 5,627,059; 5,272,071; and, WO 91/09955, WO 93/09222, WO 96/29411, WO 95/31560, and WO 91/12650.

Transgenic animals with integrated SM-MHC promoter sequences can be used to assay for SM specific transcription. In some embodiments, an SM-MHC promoter sequence, linked either to a reporter gene or to native SM-MHC coding sequence, is injected into the embryo of a developing animal (typically a mouse) to generate a transgenic animal. Once integration of the transgene has been verified, smooth muscle and non-smooth muscle tissues of the animal are then assayed for expression of the transgene with conventional RNA or protein detection methods known in the art and described herein. Typically, a rat or a human SM-MHC promoter sequence is employed, in which case RNA expressed from the transgene may be distinguished from RNA expressed from the endogenous mouse SM-MHC locus by employing appropriate polynucleotide probes that are specific for the rat or human SM-MHC sequence. Alternatively, where the SM-MHC promoter sequence is linked to a reporter gene, tissues of the transgenic animal may be assayed either for reporter gene RNA or for the enzymatic activity of the reporter protein (see, e.g., Examples 1, 2 and 4).

C. Exemplary SM-MHC Promoter/Enhancers

The SM specific promoter disclosed herein can be obtained as described in the Examples, e.g., cloned from genomic DNA libraries or isolated using amplification techniques with oligonucleotide primers. An exemplary SM specific promoter is the rat −4.2 to +11.6 region promoter/enhancer of rat SM-MHC (SEQ ID NO:16) (see also, Madsen et al., Circ. Res. 82:908–917, 1998). The corresponding human SM-MHC promoter/enhancer sequence has also been identified (the −5,086 to +13,518 fragment; SEQ ID NO:17). Other than the 5'-flanking sequence (e.g., residues 1–4216 of SEQ ID NO:16) and the short first exon (e.g., the 88 bp exon in SEQ ID NO:16), these SM-MHC promoter/enhancer sequences also contain portion of the first intron of the SM-MHC gene.

Some of the SM-MHC promoter/enhancers confer specificity in all SM cells. For example, the −4.2 to +11.6 kb fragment of the SM-MHC promoter/enhancer (corresponding to residues 1–16011 of SEQ ID NO:16) exhibits high level activity in virtually all SMC subtypes (FIGS. 1–3 and 12). Transgene expression under control of this promoter was observed in both arterial and venous smooth muscle, airway smooth muscle of the trachea and bronchi and in the smooth muscle layers of all abdominal organs, including the stomach, intestine, ureters and bladder. In addition, the transgene was expressed at high levels throughout the coronary circulation (see, FIG. 7). During development, transgene expression was first detected in airway SMC at embryonic day 12.5 and in vascular and visceral SMC tissues by embryonic day 14.5.

Figure 17:
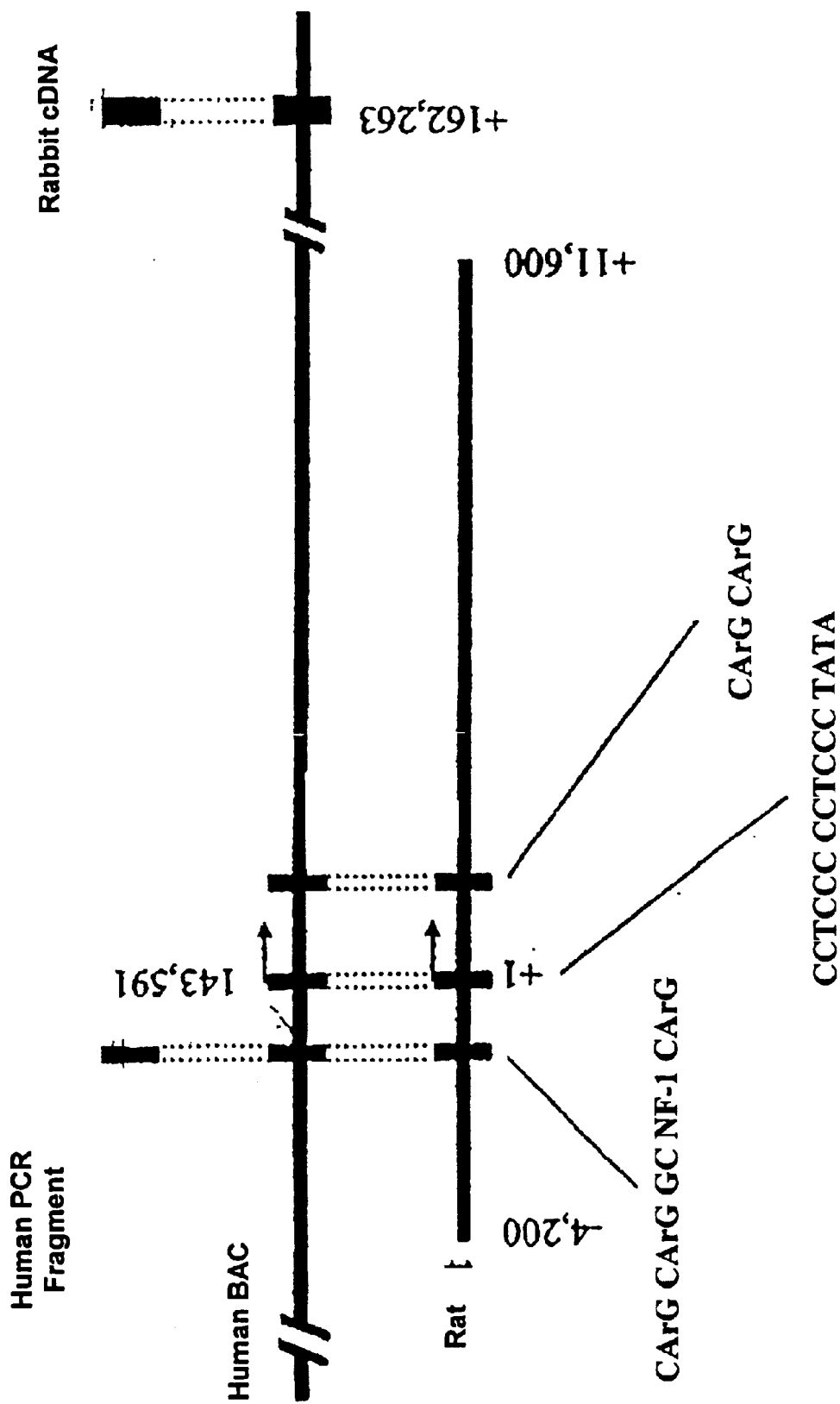
FIG. 17 shows schematic representation of the rat SM-MHC 4.2-Intron-lacZ clone and a comparable region of the human SM-MHC gene. As indicated, there is conservation of key regulatory elements including the CArG boxes, the GC repressor and an NF-1 site.

Human SM-MHC promoter/enhancer with in vivo SM specificity was also identified by the present inventors. As disclosed in Examples 2–4 and FIGS. 9–10), the region from −5086 to +13518 of the human SM-MHC gene (SEQ ID NO:17) was found highly active in multiple SMC tissues, but exhibited absolutely no expression in non-SMC tissues. This included expression in SMC within multiple small and large vessels including the aorta, coronary arteries, illiac, celiac, mesenteries, etc. This promoter was also robustly expressed in SMC within the stomach, intestine, bladder, ureter, and airways. As illustrated in FIGS. 11, 17 and 18, there is complete sequence homology between the rat and human genes in the key regulatory regions identified thus far (e.g. 5' CArG 1, 2 and 3; the G/C repressor, etc., as indicated). The identity of these elements in the rabbit and mouse genes have been shown previously (e.g., Iadsen et al., 1997, *J. Biol. Chem.*, 272:6332).

Other than conferring specificity in all SM tissues, some SM-MHC promoter/enhancers confer SM specificity only in selective subtypes of SM tissues (i.e. vascular versus gastrointestinal SMC, large versus small arteries, pulmonary versus gastrointestinal SMC, etc.) (see, Examples 2–4, FIGS. 4–8). Various derivative SM-MHC promoter/ enhancers obtained from the –4.2 to +11.6 kb rat SM-MHC promoter/enhancer region were found to be active in one or more, but not all subtypes of SM tissues. For example, some of such SM-MHC promoter/enhancers include those that comprise essentially the sequence of nucleotides 5663 to 5889 of SEQ ID NO:16 (corresponding to the intronic region of +1447 to +1673). This fragment contains three repeats of the intronic region of SM-MHC, and when coupled to a minimal thymidine kinase (TK) promoter, confers high level expression in multiple SMC tissues including the aorta, coronary arteries, and pulmonary artery (See FIG. 7).

Some of the subtype-specific SM-MHC promoter/ enhancers have an excision of the region from +5.3 to +11.6 kb. These promoters do not confer SM expression in vascular SMC but retain the activity in gastrointestinal, and bladder SMC. Some of these subtype-specific SM-MHC promoter/enhancers consists essentially the regions –4.2 to +5.3 and +7.5 to +9.5 (corresponding to residues 1 to 9,500 and nucleotides 11,700 to 13,700 of SEQ ID NO:16), or –4.2 to +2.5 and +5.3–11.6 (corresponding to residues 1 to 6,700 and nucleotides 9,500 to 15,800 of SEQ ID NO:16). They exhibit very high activity in both pulmonary vascular and airway SMC (see FIGS. 4–6).

In still some other SM-MHC promoter/enhancers, subtype-specificity is conferred by the deletion of certain conserved motifs (e.g., the intronic CArG motif or the CArG2 motif). For example, some of the promoter/ enhancers have a mutation in the conserved intronic CArG element (i.e., residues 5815–5824 of SEQ ID NO:16). An exemplary mutant has the intronic CArG sequence changed from CCTTGTATGG (SEQ ID NO:5) to AGGCCTATGG (SEQ ID NO:6). The mutation abolishes promoter activity in the aorta, coronary arteries, and the carotid artery, without affecting expression in other SMC tissues including pulmonary vascular or airway SMC (see, e.g., FIG. 8). Some other SM-MHC promoters have a mutation in the CArG2 motif (i.e., residues 3105–3114 of SEQ ID NO:16). An exemplary promoter having such a mutation has the CArG2 sequence changed from TTCCTTTTATGG (SEQ ID NO:1) to GGATCCTATGG (SEQ ID NO:2).

D. Expression Vectors and Transgenic Animals

The invention provides expression vectors for targeted gene delivery and expression in SM cells. The expression vectors comprise an SM-MHC promoter/enhancer sequence operably linked to a heterologous gene (in a preferred embodiment, a structural gene). The heterologous coding sequence operably linked to an SM-MHC promoter/ enhancer of the invention can be a marker or reporter gene (e.g., alkaline phosphatase, SEAP; β-galactosidase), a modified SM-MHC structural gene or an SM-MHC antisense sequence, a therapeutic gene. Other than the promoter and a heterologous gene, the vectors can also comprise other elements, e.g., origins of replication. These constructs are useful for SM-MHC promoter-based assays, for example, to identify biological modulators of SM-MHC promoter/ enhancer activity.

Some of the SMC specific expression vectors of the present invention comprise an SM-MHC promoter sequence described above. Some of the expression vectors contain the polynucleotide sequence of SEQ ID NO:16 or 17. Some expression vector contain an SM-MHC promoter/enhancer which consists essentially of one of the following sequences 1) the intronic region from +1447 to +1673 (residues 5663 to 5889) of SEQ ID NO:16;

2) the region of –4.2 to +11.6 of SEQ ID NO:16, wherein CArG2 or intronic CArG have been mutated;

3) the regions of –4.2 to +2.5 and +5.3 to +11.6 (residues 1 to 6,700 and nucleotides 9,500 to 15,800)of SEQ ID NO:16; and 4) the regions of –4.2 to +5.3 and +7.5 to +9.5 (residues 1 to 9,500 and nucleotides 11,700 to 13,700 of SEQ ID NO:16) of SEQ ID NO:16.

As discussed in more detail below, these expression vectors are useful for targeting gene expression specifically to smooth muscle or subtypes of smooth muscle, development of animal models of human disease for drug screening, or elucidation of pathogenic mechanisms and identification of new therapeutic targets.

Employing aforementioned expression vectors, the present invention provides host cells and transgenic animals which have incorporated a heterologous polynucleotide in SM cells. Such host cells or transgenic animals (e.g., transgenic mice) of the present invention can be produced as described above and in the Examples. The transgenic cells or animals of the present invention can be used in various applications, e.g., development of animal models for purpose of screening new drugs/therapies. For example, if a specific gene is known to be involved in an SMC-based disease, the gene can be operably linked to an SM-MHC promoter/enhancer of the instant invention to produce an animal model of the disease.

In addition, transgenic cells or animals of the present invention can also comprise an SM-MHC promoter/ enhancer operably linked to a gene which expresses a protein which can inhibit (a) other proteins or (b) transcription of other genes that further the diseased state being examined within the animal model. Alternatively, the SM-MHC promoter/enhancer can be operably linked to an antisense gene, which could specifically inhibit expression of a gene which may be involved in the diseased state. Using such animal models, one of skill in the art could test conventional drug therapies, identify key genes involved in the development of these diseases and/or develop a novel way of curing the disease.

IV. Targeted Gene Delivery and Expression

The present invention provides methods for targeted delivery of therapeutic agents to SM cells in a subject (human or non-human animals). The therapeutic agents include polynucleotides that are specifically expressed in vivo under the control of the SM-MHC promoter/enhancers. Virtually any gene can be specifically expressed within SMC in the subject. The expression vectors can be introduced or reintroduced into a subject (e.g., a human patient) at positions which allow for the amelioration of SMC-related disease. The subtype-specific SM-MHC promoter derivatives that are selectively active in subsets of SMC (e.g. vascular versus gastrointestinal SMC, large versus small arteries, pulmonary versus gastrointestinal SMC, etc.) enable targeted gene expression in specific subtypes of smooth muscle in vivo. Thus, advantages of the targeting methods of the present invention include complete SMC specificity, the ability to target specific SMC subsets, a small size compatible with existing gene delivery methods, and high level activity.

For example, the expression vectors of the present invention can be employed in targeting expression of a therapeutic gene to the specific subtype of SMC desired (e.g. bronchiolar SMC for treatment of asthma or chronic bronchitis) thereby increasing the efficacy of the therapy and reducing potential side effects due to over-expression in undesired tissues and cells. In addition, the expression vectors can also be used in development of animal models of human disease to assist in development of new therapeutic targets. Further, the expression vectors and targeting methods of the present invention can also be used in identification and/or selection of smooth muscle cells derived from multi-potential stem cell populations for purposes of tissue generation/regeneration for surgery (e.g. for blood vessel, bladder, or gastrointestinal smooth muscle tissue augmentation-reconstitution).

A. Diseases Amenable to Treatment with Methods of the Present Invention

The present invention provides compositions and methods for targeted gene delivery and expression that can be used to treat a variety of diseases and conditions. A large number of major human diseases including systemic hypertension, pulmonary hypertension, atherosclerosis, asthma, coronary artery disease, gastrointestinal abnormalities, reproductive dysfunction, and chronic bronchitis are associated with abnormal function of the smooth muscle cell (SMC). A specific example is to target over-expression of nitric oxide synthase (the enzyme responsible for production of the SMC relaxant nitric oxide or NO from L-arginine) to bronchiolar SMC using our SM-MHC promoter derivative that is active in bronchiolar SMC but inactive in many other SMC tissues. This targeting would be critical to avoid potential deleterious effects of over-expression of NO in other SMC subtypes including vascular SMC which might be associated with severe hypotension and possible death. Similar approaches could be used to target NO synthase to arteriolar SMC as a means of treating certain forms of hypertension that are resistant to current therapies.

The present invention also find application in development of animal models of disease for purposes of testing potential new drugs/therapies, and/or identifying disease mechanisms. For example, one might over-express protease enzymes in vascular SMC in large blood vessels as a model to study development of aneurysms and ways to prevent or treat them. Additional applications of the present invention include development of gene targeting therapies for promoting formation of collateral vessels following tissue ischemia. Methods of the present invention can be used in developing ways to promote formation of collateral blood vessels in the myocardium following a non-fatal heart attack. For example, the targeting methods of the present invention can be used to over-express angiogenic substances such as VEGF in the coronary microcirculation in an ischemic heart region.

The present inventors have identified a molecular mechanism that appears to be important in mediating repression of SM cell marker genes such as SM-MHC and SM22a that occur when SM cells undergo phenotypic modulation in response to vascular injury. Specifically, a G/C repressor element was identified within the promoters of both the SM-MHC and SM22 genes. This repressor element was found to mediates suppression of the activity of these promoters in phenotypically modulated cultured SMC (see, e.g., Madsen et al., *J. Biol. Chem.* (1997) 272:6332–6340; and Madsen et al., *J. Biol. Chem.* (1997) 272:29842–29851). It was shown that mutation of the SM22a G/C element prevented injury-induced down-regulation of these genes, but did not affect the tissue selectivity of this promoter. Such an repressor element can be the target (or "useful") in SMC gene targeting applications that are associated with phenotypic modulation of SMC, e.g., post-angioplasty restenosis, intimal SMC within atherosclerotic lesions, or vascular remodeling in pulmonary hypertension, etc. For example, the SM-MHC promoter/enhancer of the present invention can be used in the context of vascular injury in which activity of the wild type SM-MHC promoter is repressed.

B. Targeted Delivery of Therapeutic Agents

Therapeutic agents to be delivered with the targeting methods of the present invention include any therapeutic polynucleotide operably linked to an SM-MHC promoter sequence in an expression vector discussed above. Therapeutic polynucleotides (including those that can be identified with the screening methods described below) expressed by SM-MHC promoter sequences are either active themselves (e.g., antisense and catalytic polynucleotides) or encode a therapeutic protein.

1. Antisense and Catalytic Ribonucleotides

One type of therapeutic polynucleotide that can be expressed by SM-MHC promoter sequences is antisense RNA. In such embodiments, the SM-MHC promoter sequence is operably linked to a polynucleotide which, when transcribed by cellular polymerases, is capable of binding to target MRNA. The derivation of an antisense sequence, based upon a cDNA sequence encoding a target protein is described in, for example, Stein and Cohen, *Cancer Res* 48:2659 (1988) and van der Krol et al., *BioTechniques* 6:958 (1988). Antisense oligonucleotides that form triplexes with a target promoter regions inhibit the activity of that promoter, see, e.g., Joseph (1997) Nucleic Acids Res. 25:2182–2188; Alunni-Fabbroni (1996) Biochemistry 35:16361–16369; Olivas (1996) Nucleic Acids Res 24:1758–1764. Alternatively, antisense oligonucleotides that hybridize to the promoter sequence can be used to inhibit promoter activity.

In addition to antisense polynucleotides, ribozymes can be designed to inhibit expression of target molecules. A ribozyme is an RNA molecule that catalytically cleaves other RNA molecules. Accordingly, SM-MHC promoter sequences may be used to express ribozymes specifically in smooth muscle cells by linking a polynucleotide encoding a ribozyme to an SM-MHC promoter sequence. Methods for constructing and using ribozymes to treat smooth muscle cancer in particular are described by Dorai et al., *Smooth muscle* 32:246–58 (1997); Norris et al., *Adv Exp Med Biol* 465:293–301 (2000). Different kinds of ribozymes have been described, including group I ribozymes, hammerhead ribozymes, hairpin ribozymes, RNase P, and axhead ribozymes (see, e.g., Castanotto et al. (1994) *Adv. in Pharmacology* 25: 289–317 for a general review of the properties of different ribozymes). The general features of hairpin ribozymes are described, e.g., in Hampel et al. (1990) *Nucl. Acids Res.* 18: 299–304; Hampel et al. (1990) European Patent Publication No. 0 360 257; U.S. Pat. No. 5,254,678. Methods of preparing are well known to those of skill in the art (see, e.g., Wong-Staal et al., WO 94/26877; Ojwang et al. (1993) *Proc. Natl. Acad. Sci. USA* 90: 6340–6344; Yamada et al. (1994) *Human Gene Therapy* 1: 39–45; Leavitt et al. (1995) *Proc. Natl. Acad. Sci. USA* 92: 699–703; Leavitt et al. (1994) *Human Gene Therapy* 5: 1151–120; and Yamada et al. (1994) *Virology* 205: 121–126).

2. Therapeutic Proteins

A wide variety of therapeutic proteins may be used to treat smooth muscle diseases. Accordingly, the SM-MHC promoter sequences of the present invention may be used to express polynucleotides encoding therapeutic proteins specifically in smooth muscle cells. Therapeutic proteins may be of prokaryotic, eukaryotic, viral, or synthetic origin. Where the therapeutic protein is not of mammalian origin, the coding sequence of the protein may be modified for maximal mammalian expression according to methods known in the art (e.g., mammalian codon usage and consensus translation initiation sites).

Therapeutic proteins that can be employed in the targeted gene delivery methods of the present invention include proteins that kill the cell when expressed, such as microbial toxins (Pang, *Cancer Gene Ther* 7:991–6 (2000)) and proteins involved in apoptosis (Li et al., *Cancer Res* 61:186–91 (2001); Schumacher et al., *Int J Cancer* 91:159–66 (2001); Hyer et al., *Mol Ther* 2:348–58 (2000); Griffith et al., *J Immunol* 165:2886–94 (2000)). Smooth muscle cells can also be targeted with proteins that sensitize smooth muscle cells to therapy. Such proteins may function by converting a prodrug to an active metabolite (e.g., thymidine kinase or cytosine deaminase; for review see Aghi et al., *J Gene Med* 2: 148–64 (2000)), by increasing cell permeability to a therapeutic agent, by restoring hormonal responsiveness, or by rendering the cell more sensitive to radiotherapy or chemotherapeutics. See, e.g., Suzuki et al., *Cancer Res* 61:1276–9 (2001); Cowen et al., *Clin Cancer Res* 6:4402–8 (2000); Spitzweg et al., *Cancer Res* 60:6526–30 (2000); Anello et al., *J Urol* 164:2173–7 (2000); Fan et al., *Cancer Gene Ther* 7:1307–14 (2000); Nielsen, *Oncol Rep* 7:1191–6 (2000); Ayala et al., *Hum Pathol* 31:866–70 (2000); Boland et al., *Cancer Res* 60:3484–92 (2000). Other proteins that can be employed include proteins that inhibit proliferation or act as anti-oncogenes or tumor suppressors (Shirakawa et al., *J Gene Med* 2:426–32 (2000); Tanaka et al., *Oncogene* 19:5406–12 (2000); Okegawa et al., *Cancer Res* 60:5031–6 (2000); Allay et al., *World J Urol* 18:111–20 (2000); Steiner et al., *Cancer Res* 60:4419–25 (2000)), proteins that inhibit angiogenesis (Jin et al., *Cancer Gene Ther* 7:1537–42 (2000)) and proteins that induce an immune response, such as cytokines or foreign antigens (Hull et al., *Clin Cancer Res* 6:4101–9 (2000)). See also U.S. Pat. No. 6,136,792.

C. Delivery System for Targeted Gene Delivery

The expression vectors of the present invention can be transfected into cells for therapeutic purposes in vitro and in vivo. These polynucleotides can be inserted into any of a number of well-known vectors for the transfection of target cells and organisms as described below. The expression vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a polynucleotide (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic polynucleotides can also be administered directly to the organism for transduction of cells in vivo. Alternatively, naked DNA can be administered. Administration is by any of the routes normally used for introducing a molecule into ultimate contact with blood or tissue cells. Suitable methods of administering such polynucleotides are available and well known to those of skill in the art, and, although more than one route can be used to administer a particular composition, a particular route can often provide a more immediate and more effective reaction than another route.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357:455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first step in gene therapy treatment of disease. A large number of delivery methods are well known to those of skill in the art. Preferably, the polynucleotides are administered for in vivo or ex vivo gene therapy uses. Non-viral vector delivery systems include DNA plasmids, naked polynucleotide, and polynucleotide complexed with a delivery vehicle such as a liposome. Viral vector delivery systems include DNA and RNA viruses, which have either episomal or integrated genomes after delivery to the cell.

Methods of non-viral delivery of polynucleotides include lipofection, microinjection, biolistics, virosomes, liposomes, immunoliposomes, polycation or lipid:polynucleotide conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:polynucleotide complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of polynucleotides take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polynucleotides could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the polynucleotide is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target polynucleotides, e.g., in the in vitro production of polynucleotides and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, a number of viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al, *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors (Ellem et al., *Immunol Immunother.* 44(1):10–20 (1997); Dranoff et al., *Hum. Gene Ther.* 1:111–2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998), Kearns et al., *Gene Ther.* 9:748–55 (1996)).

Replication-deficient recombinant adenoviral vectors (Ad) are predominantly used in transient expression gene therapy, because they can be produced at high titer and they readily infect a number of different cell types. Most adenovirus vectors are engineered such that a transgene replaces the Ad E1a, E1b, and E3 genes; subsequently the replication defective vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 241:5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

D. Pharmaceutical Compositions

The invention provides pharmaceutical compositions that comprise SM-MHC promoter-containing therapeutic polynucleotides (e.g., oligo- and poly-nucleotides, expression vectors, gene therapy constructs, etc.) alone or in combination with at least one other agent, such as, e.g., a stabilizing compound, diluent, carrier, cell targeting agent, or another active ingredient or agent. The therapeutic agents of the invention may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipient(s), adjuvants, and/or pharmaceutically acceptable carriers. Pharmaceutically acceptable carriers are determined in part by the particular composition being administered (e.g., polynucleotide, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989).

Pharmaceutical compositions of the invention include SM-MHC promoter-containing polynucleotides in an effective amount to achieve the intended purpose. "Therapeutically effective amount" or "pharmacologically effective amount" are well recognized phrases and refer to that amount of an agent effective to produce the intended pharmacological result. For example, a therapeutically effective amount is an amount sufficient to treat a disease or condition or ameliorate the symptoms of the disease being treated. The therapeutically effective dose can be estimated initially either in cell culture assays or in any appropriate animal model. The animal model is also used to estimate appropriate dosage ranges and routes of administration in humans. In determining the effective amount of the vector to be administered, the physician evaluates circulating plasma levels of the vector, vector toxicities, progression of the disease, and the production of anti-vector antibodies. In general, the dose equivalent of a naked polynucleotide from a vector is from about 1 μg to 100 μg for a typical 70 kilogram patient, and doses of vectors which include a retroviral particle are calculated to yield an equivalent amount of therapeutic polynucleotide.

The pharmaceutical compositions of the invention can be administered by any means, such as, e.g., injection, oral administration, inhalation, transdermal, or parenteral application. Methods of parenteral delivery include e.g., topical, intra-arterial (e.g., directly to the tumor), intramuscular (IM), subcutaneous (SC), intramedullary, intrathecal, intraventricular, intravenous (IV), intraperitoneal (IP), or intranasal administration. Further details on techniques for formulation and administration may be found in the latest edition of "REMINGTON'S PHARMACEUTICAL SCIENCES" (Maack Publishing Co, Easton Pa.). See also, e.g., PCT publication WO 93/23572.

V. Screening for Modulators of SM-MHC Promoter/Enhancer

The invention also provides constructs, cell lines and methods for screening for small molecule modulators of SM-MHC promoter/enhancer activity in vitro and in vivo. Many assays are available that screen for small molecule modulators of SM-MHC transcription, including high throughput assays.

As described in detail in the Examples, results from constructs containing an SM-MHC promoter/enhancer sequence and a marker gene (in this example, the lacZ gene) indicated that various motifs of SM-MHC promoter/enhancer sequence play a role in the SM specificity and subtype specificity of the SM-MHC promoters. These constructs can be employed for high throughput screening of modulators of the SM-MHC modulators. Additional cis-acting regulatory elements within an SMC promoter/enhancer can also be identified as described in the present invention.

The present invention also encompasses assays for identifying compounds that modulate expression under the SM-MHC promoter sequences. Such modulatory compounds are useful in enhancing or inhibiting the expression of genes transcribed by the SM-MHC promoters, thus providing additional control and specificity over their expression. Compounds and other substances that modulate expression of the SM-MHC promoter/enhancer can be screened using in vitro cellular systems. After applying a compound or other substance to the test system, RNA can be extracted from the cells. The level of transcription of a specific target gene can be detected using, for example, standard RT-PCR amplification techniques and/or Northern analysis. Alternatively, the level of target protein production can be assayed by using antibodies that detect the target gene protein. Preferably, the SM-MHC can be fused to a reporter gene and the expression of the reporter gene can be assessed. Such reporter genes, for which assays are well known to those of skill in the art, include, but are not limited to lacZ, β glucoronidase, enhanced green fluorescence protein, etc. See, e.g., Khodjakov et al., 1997, *Cell. Motil. Cytoskeleton,* 38:311–317. The level of expression is compared to a control cell sample which was not exposed to the test compound. The activity of the compounds also can be assayed in vivo using transgenic animals according to the methods described, for example, in Examples 2–5, below.

Compounds that can be screened for modulation of expression of the target gene include, but are not limited to, small inorganic or organic molecules, peptides, such as peptide hormones analogs, steroid hormones, analogs of such hormones, and other proteins. Compounds that down-regulate expression include, but are not limited to, oligonucleotides that are complementary to the 5'-end of the mRNA of the SM-MHC and inhibit transcription by forming triple helix structures, and ribozymes or antisense molecules which inhibit translation of the target gene mRNA. Techniques and strategies for designing such down-regulating test compounds are well known to those of skill in the art.

A. Identifying Cis-Acting Elements of SM-MHC Promoter/Enhancer

Multiple cis-elements identified within the first 4.2-kb of 5'-flanking sequence of the SM-MHC promoter are critical for expression in cultured SMC. (White S. L. et al., 1996, *J. Biol. Chem.,* 271:15008–15017; Katoh Y. et al., 1994, *J. Biol. Chem.,* 269:30538–30545; Wantanabe M. et al., 1996, *Biol. Chem.,* 269:30538–30545; Wantanabe M. et al., 1996, *Circ. Res.,* 78:978–989; Kallmeier R. C. et al., 1995, *J. Biol. Chem.,* 270:30949–30957; Madsen C. S. et al., 1997, *J. Biol. Chem.,* 272:6332–6340; Madsen C. S. et al., 1997, *J. Biol. Chem.,* 272:29842–29851). The fact that the p4.2-lacZ construct was found to be active in cultured SMC, but completely inactive in vivo, indicates that additional regulatory elements are necessary for expression within the in vivo context. Furthermore, the fact that the p4.2-Intron-lacZ construct containing approximately 16 kb of the rat SM-MHC genomic region from −4.2 kb to +11.7 kb was expressed in SMC-tissues within transgenic mice whereas the p4.2-lacZ construct was inactive, strongly suggests that the first 11.6 kb region of intron I contains enhancer elements required for expression in vivo but not in cultured SMC.

Additional cis-acting elements of SM-MHC promoter/enhancer can be identified using methods of molecular genetic analysis well known in the art. For example, the location of cis-regulatory elements within a promoter/enhancer may be identified using methods such as DNase or chemical footprinting (e.g. Meier et al., 1991, *Plant Cell* 3:309–315) or gel retardation (e.g., Weissenbom & Larson, 1992, *J. Biol. Chem.* 267-6122–6131; Beato, 1989, *Cell* 56:335–344; Johnson et al., 1989, *Ann. Rev. Biochem.* 58:799–839). Additionally, resectioning experiments also may be employed to define the location of the cis-regulatory elements. For example; a promoter/enhancer containing fragment may be resected from either the 5' or 3' end using restriction enzyme or exonuclease digests.

Another method for identifying transcriptional regulatory motifs involves modifying putative cis-acting regulatory subsequences and assessing the change, if any, of the resultant SM-MHC promoter/enhancer to modulate transcription. The modification can be, e.g., one or more residue deletions, residue substitution(s), chemical alteration(s) of nucleotides, and the like. The (modified) promoter can be operably linked to a transcribable sequence (e.g., reporter genes). The relative increase or decrease the modification has on transcriptional rates can be determined, e.g., by measuring the ability of the unaltered SM-MHC promoter/enhancer to transcriptionally activate the reporter coding sequence under the same conditions as used to test the modified promoter. An increase or decrease in the ability of the modified SM-MHC promoter/enhancer to induce transcription as compared to the unmodified promoter construct identifies a cis-acting transcriptional regulatory sequence that is involved in the modulation of SM-MHC promoter/enhancer activity.

The reporter gene can encode any detectable protein known in the art, e.g., detectable by fluorescence or phosphorescence or by virtue of its possessing an enzymatic activity. In alternative embodiments, the detectable protein is firefly luciferase, alpha-glucuronidase, alpha-galactosidase, chloramphenicol acetyl transferase, green fluorescent protein, enhanced green fluorescent protein, and the human secreted alkaline phosphatase.

B. Identifying SM-MHC Promoter/Enhancer Trans-Acting Transcriptional Regulatory Factors The invention provides means to identify and isolate trans-acting transcriptional regulatory factors that are involved in modulating the activity of the SM-MHC promoter/enhancer. Identification of cis-acting motifs by, e.g., sequence identity comparison, can be a useful initial means to identify promoter sequences bound by trans-acting factors. For example, as discussed above, the hSM-MHC and rSM-MHC promoter/enhancers contain a variety of cis-acting motifs (e.g., the CArG motifs and the G/C repressor).

After positive or tentative identification of a cis-acting binding site in an SM-MHC promoter/enhancer, these sequences are used to isolate the trans-acting transcriptional regulatory factor(s) by any means known in the art. In some embodiments, the trans-acting factors are isolated using sequence-specific oligonucleotide affinity chromatography, the oligonucleotides comprising SM-MHC promoter sequences of the invention.

Another method tests the ability of the cis-acting elements to bind soluble polypeptide trans-acting factors isolated from different cellular compartments, particularly trans-acting factors expressed in nuclei. For identification and isolation of factors that stimulate transcription, cell (e.g. nuclear) extracts from cells that express SM-MHC are used. Means to conduct these studies are well known in the art (see also Example 5).

Furthermore, as discussed further below, once a cis-acting motif, or element, is identified, it can be used to identify and isolate trans-acting factors in a variety of cells and under different conditions (e.g., cell proliferation versus cell senescence). Accordingly, the invention provides a method for screening for trans-acting factors that modulate SM-MHC promoter/enhancer activity under a variety of conditions, developmental states, and cell types (including, e.g., normal versus immortal versus malignant phenotypes).

C. High Throughput Screening of Small Molecule Modulators of SM-MHC Promoter

The invention provides constructs and methods for screening modulators, in a preferred embodiment, small molecule modulators, of SM-MHC promoter/enhancer activity in vitro and in vivo. The invention incorporates all assays available to screen for small molecule modulators of SM-MHC transcription. In a preferred embodiment, high throughput assays are adapted and used with the SM-MHC promoter/enhancer sequences and constructs provided by the invention. See, e.g., Schultz (1998) Bioorg Med Chem Lett 8:2409–2414; Weller (1997) Mol Divers. 3:61–70; Fernandes (1998) Curr Opin Chem Biol 2:597–603; Sittampalam (1997) Curr Opin Chem Biol 1:384–91.

One embodiment of the invention provides a method of screening and isolating an SM-MHC promoter/enhancer binding compound by contacting an SM-MHC promoter/enhancer sequence of the invention particularly, an identified cis-acting regulatory sequence) with a test compound and measuring the ability of the test compound to bind the selected polynucleotide. The test compound, as discussed above, can be any agent capable of specifically binding to an SM-MHC promoter/enhancer activity, including compounds available in chemical (e.g., combinatorial) libraries, a cell extract, a nuclear extract, a protein or peptide.

A variety of well-known techniques can be used to identify polypeptides which specifically bind to SM-MHC promoter/enhancer sequences, e.g., mobility shift DNA-binding assays, methylation and uracil interference assays, DNase and hydroxy radical footprinting analysis, fluorescence polarization, and UV crosslinking or chemical crosslinkers. For a general overview, see, e.g., Ausubel, supra, (chapter 12, DNA-Protein Interactions); McLaughlin (1996) Am. J. Hum. Genet. 59:561–569; Tang (1996) Biochemistry 35:8216–8225; Lingner (1996) Proc. Natl. Acad. Sci. USA 93:10712; and Chodosh (1986) Mol. Cell. Biol 6:4723–4733. Where an antibody may already be available or one can be easily generated, co-immunoprecipitation analysis can be used to identify and isolate SM-MHC promoter/enhancer-binding, trans-acting factors. The trans-acting factor can be characterized by peptide sequence analysis. Once identified, the function of the protein can be confirmed by methods known in the art, for example, by competition experiments, factor depletion experiments using an antibody specific for the factor, or by competition with a mutant factor.

Alternatively, SM-MHC promoter/enhancer-affinity columns can be generated to screen for potential SM-MHC binding proteins. In a variation of this assay, SM-MHC promoter/enhancer sequence or a subsequences is biotinylated, reacted with a solution suspected of containing a binding protein, and then reacted with a strepavidin affinity column to isolate the polynucleotide or binding protein complex (see, e.g., Grabowski (1986) Science 233:1294–1299; Chodosh (1986) supra). The promoter-binding protein can then be conventionally eluted and isolated. Mobility shift DNA-protein binding assay using non-denaturing polyacrylamide gel electrophoresis (PAGE) is an extremely rapid and sensitive method for detecting specific polypeptide binding to DNA (see, e.g., Chodosh (1986) supra, Carthew (1985) Cell 43:439–448; Trejo (1997) J. Biol. Chem. 272:27411–27421; Bayliss (1997) Nucleic Acids Res. 25:3984–3990).

Interference assays and DNase and hydroxy radical footprinting can be used to identify specific residues in the polynucleotide protein-binding site, see, e.g., Bi (1997) J. Biol. Chem. 272:26562–26572; Karaoglu (1991) Nucleic Acids Res. 19:5293–5300. Fluorescence polarization is a powerful technique for characterizing macromolecular associations and can provide equilibrium determinations of protein-DNA and protein-protein interactions (see, e.g., Lundblad, 1996, Mol. Endocrinol. 10:607–612).

Proteins identified by these techniques can be further separated on the basis of their size, net surface charge, hydrophobicity and affinity for ligands. In addition, antibodies raised against such proteins can be conjugated to column matrices and the proteins immunopurified. All of these general methods are well known in the art. See, e.g., Scopes, R. K., Protein Purification: Principles and Practice, 2nd ed., Springer Verlag, (1987).

The following examples are provided for illustrative purposes and are not intended to limit the scope of the invention.

EXAMPLES

Example 1

General Methods For Analyzing SM-MHC Transgenes

1. Isolation and Cloning of the SM-MHC Promoter/Enhancer

The SM-MHC gene contains a very short untranslated first exon (88 base pairs in rat) that is followed by a greater than 20 kb first intron. Babij P. et al., 1991, *Proc. Natl. Acad. Sci.*, 88: 10676. The cloning and sequence of the 5'-flanking region of the rat SM-MHC gene (−4229 to +88) has been previously reported. White S. L. et al., 1996, *J. Biol. Chem.*, 271:15008–15017; Madsen C. S. et al., 1997, *J. Biol. Chem.*, 272:6332–6340. To obtain 5'-flanking sequences with additional intronic DNA, a rat genomic phage library (Stratagene Corp. La Jolla, Calif.) was screened utilizing standard Southern blotting techniques, and α $^{32}$P-radiolabeled 45-mer oligonucleotide corresponding to the conserved untranslated first exon as a probe (nucleotides +14 to +58). One of the positive recombinant lambda phage clones identified contained an approximately 16 kb insert (determined by restriction enzyme and sequence analyses) that spanned the SM-MHC gene from −4,216 to +11,795. Identical restriction enzyme patterns between rat genomic DNA and multiple positive clones revealed that none of the clones identified had undergone rearrangement.

The nucleotide sequence of the rat clone which was used as the SM-MHC promoter/enhancer of the present invention is shown in SEQ ID N:21. The clone spans the rat MHC gene from position −4,216 in relation to the transcription start site to position +11,795 downstream of the transcription start site, thus, containing about 16,011 base pairs in total. Furthermore, since the first exon of the rat MHC gene is 88 base pairs in length, the clone extends to +11,707 base pairs within the first intron.

Although the instant example describes the cloning and isolation of the rat SM-MHC promoter/enhancer, key regulatory regions within this polynucleotide sequence are known to be conserved across all species that express the gene. Thus, the instant invention encompasses not only the rat SM-MHC, but also the SM-MHC of other mammals, including, but not limited to, humans, rabbits and mice. The full length human SM-MHC gene sequence has previously been deposited with the Institute for Genomic Research in Rockville, Md., and is assigned Ace. No. U91 323 and NID No. G233 5056. It can be accessed at http://www.ncbi.nlm.nih.gov/htbin-post/Entrezlquery?db=n_d. This sequence is hereby incorporated by reference in its entirety. Based upon a comparison of the human and rat SM-MHC gene sequences, FIG. 11 shows the high degree of homology that exists between the rat and human genes. In fact, as shown in FIG. 11, critical regulatory sequences are 100% conserved within the genes. Furthermore, it has previously been shown that similar regulatory sequences are conserved in the rabbit and mouse genes for SM-MHC. See, Madsen et al., 1997, *J. Biol. Chem.* 272:6332.

2. Construction of the SM-MHC-LacZ Reporters

To facilitate removal of pBS plasmid DNA from the pBS-lacZ vector, the pBS-lacZ vector was modified by inserting Not I restriction enzyme recognition sites at the HindIII and EcoRI sites located at the borders of the pBS vector sequence. Two SM-MHC-lacZ reporter genes were constructed for the generation of transgenic mice. One construct (p4.2 lacZ) was created by ligating about a 4.3 kb BglII fragment that extended from −4220 to +88 into a unique BamHI site of the pBS-lac-Z vector, and the other construct tested (p4.2-Intron-lacZ) was generated by subcloning an approximately 16 kb SaII fragment that extended from −4229 to about +11,700 into the SaII site of the pBS-lacZ vector. To facilitate splicing of the p4.2-Intron-lacZ construct, a synthetic splice acceptor site was ligated into the KpnI site of the pBS-lacZ vector prior to insertion of the SM-MHC DNA fragment. The location of the KpnI site, between the SaII site and the lacZ-gene, allowed for the correct positioning of the splice acceptor site at the +11,700 end of the SM-MHC intron. The proper construction of each SM-MHC-lacZ chimeric plasmid was verified by sequencing and restriction enzyme analyses. As an additional precaution against cloning artifacts, both transgenic constructs were tested for lacZ expression in transient transfection assays in cultured rat aortic SMC using a method that was previously described. Madsen C. S. et al., 1997, *J. Biol. Chem.*, 272:6332–634

3. Generation and Analysis of Transgenic Mice

Plasmid constructs p4.2-lacZ and p4.2-Intron-lacZ were tested for SM-MHC promoter activity in transgenic mice following removal of the pBS vector DNA through NotI digestion and subsequent agarose gel purification. Transgenic mice were generated using standard methods (Li L. et al, 1996, *J. Cell. Biol.*, 132:849–859; Gordon J. W. et al., 1981, *Science*, 2 14:1244–1246) either commercially (DNX, Princeton, N.J.) or within the Transgenic Core Facility at The University of Virginia. Transgenic mice were either sacrificed and analyzed during embryological development (transient transgenics), or were utilized to establish breeding-founder lines (stable transgenics). Transgene presence was assayed by the polymerase chain reaction using genomic DNA purified from either placental tissue (embryonic mice) or from tail clips (adult mice) according to the method of Vernet M. et al., 1993, *Methods Enzymol.* 225:434–451. Transgene expression and histological analyses were done as described previously. Li L. et al., 1996, *J. Cell. Biol.*, 132:849–859; Cheng T. C. et al., 1993, *Science*, 261:215–218. In order to determine possible positional effects of transgene insertional sites on transgene expression, multiple independent founder lines were analyzed for each transgene construct.

4. SM-MHC Immunohistochemistry

Various smooth muscle containing tissues were collected from 5–6 week old transgenic mice and fixed overnight in methacam (60% methanol, 30% chloroform, 10% glacial acetic acid). Tissues were subsequently dehydrated through a graded series of methanol dilutions. Fixed, dehydrated tissues were prepared for paraffin embedding by incubation in 100% xylene. Tissue was then infiltrated by incubation through a series of xylene:paraffin (3:1, 1:1, 1:3) solutions, and two final incubations in 100% paraffin prior to embedding in 100% paraffin. Serial sections (6 µm) were placed on uncoated slides, and then dried for approximately 45 minutes on a slide warmer set at 40° C. Sections were cleared in multiple washes of 100% xylene, and re-hydrated through a graded ethanol series to a final incubation in phosphate buffered saline (PBS). Endogenous peroxidase activity was quenched by incubating slides in methanol containing 0.3% hydrogen peroxide for 30 min. Slides were subsequently rehydrated in PBS and blocked in a 1:50 solution of normal goat serum made up in PBS. Sections were then incubated with the primary antibody for 1 hr and washed with 3 changes of PBS. Detection of primary antibody was performed using a Vectastain ABC Kit according to the instructions of the manufacturer with diaminobenzidine (DAB) as the chromogen (Vector Laboratories, Burlingame, Calif.).

Antibodies:

Several different SM-MHC antibodies were employed. These included a monoclonal antibody designated 9A9 which has been previously characterized (Price R. J. et al., 1994, *Circ. Res.*, 75:520–527) that shows reactivity with the SM-1 and SM-2 isoforms of SM-MHC but which shows no reactivity with non-muscle myosin heavy chains or other proteins. However, whereas this antibody showed some reactivity with mouse SM-MHC isoforms in Western analyses, it reacted very poorly with mouse SM-MHC in fixed tissues. In addition, although a polyclonal SM-MHC peptide antibody provided by Nagai R. et al, 1989, *J. Biol. Chem.*, 264:9734–973 7, showed complete specificity for SM-MHC isoforms in Western analyses of smooth muscle tissues from multiple species, it showed little or no reactivity with mouse SM-MHC isoforms. To circumvent these limitations, a rabbit anti-chicken gizzard SM-MHC polyclonal antibody was employed. The rabbit anti-chicken gizzard SM-MHC antibody was made by immunization of rabbits with partially purified gizzard SM-MHC as described by Groschel-Stewart, 1976, *Histochemistry* 46:229–236. However, based on Western analyses, it was determined that this antibody showed reactivity with both SM-1 and SM-2 MHC, as well as with non-muscle myosin B (or SMEMB), as did a number of other "smooth muscle myosin" antibodies tested, including one from Sigma [designated hSM-V] (Frid M. G. et al., 1993, *J. Vasc. Res.*, ;30:279–292) and one from R. S. Adelstein (Schneider M. D. et al., 1985, *J. Cell. Biol.*, 101:66). As such, staining with these antibodies in tissues that express both SMEMB and SM-MHC is equivocal. However, adult mouse aortic SMC, like those in other species (Rovner A. S. et al., 1986, *J. Biol. Chem.*, 261: 14740–14745; Rovner A. S. et al., 1986, *Am. J Physiol.*, 250:c861–c870; Phillips C. L. et al., 1995, *J. Muscle Res. & Cell Motility*, 16:379–389) were not found to express SMEMB based on Western analyses. The rabbit anti-chicken gizzard SM-MHC polyclonal antibody was used at a concentration of approximately 20 μg/ml in PBS. Biotinylated goat anti-rabbit secondary antibodies were purchased from Vector Laboratories (Burlingame, Calif.) and used at a concentration of 10 μg/ml in PBS. Appropriate Western analyses, and immunohistological controls were performed to assess specificity, including exclusion of primary antibody, and use of control non-immune rabbit serum.

5. Chromatin Immunoprecipitation

L6 rat skeletal myoblasts were cultured in α-minimal essential medium (Lifetechnologies) supplemented with 2% FBS for 7 days to induce myotube formation. L6 myotubes, L6 myoblasts, Rat1 fibroblasts, and rat aortic SMCs in 100 mm dished were fixed directly by adding 280 μl of 37% formaldehyde to 10 ml of culture media and incubating at 37° C. for 10 min. The fixed cells were harvested and prepared for immunoprecipitation using the protocol of ChIP assay kit (Upstate Biotechnology) with minor modifications. A quarter of the sample was precleared with salmon sperm DNA/protein A agarose (Upstate) and subsequently incubated with either 2 μl of anti-SRF antibody (Santa Cruz Biotechnology) or no antibody at 4° C. over night. Chromatin samples were immunoprecipitated using salmon sperm DNA/protein A (Upstate). Samples were washed two times with 1 ml of wash buffer A (0.1% SDS, 1% Triton X-100, 2 mM EDTA, 20 mM Tris-HCl, pH 8.1, 150 mM NaCl), once with wash buffer B (0.25 M LiCl, 0.5% NP-40, 0.5% sodium deoxycholate, 1 mM EDTA, 10 mM Tris-HCl, pH 8.1), and two times with TE. Immune complexes were eluted and subsequently reverse-crosslinked and purified by phenol/chloroform extraction. Ethanol precipitated DNA pellets were redissolved in 40 μl of TE buffer. The supernatant of an immunoprecipitation reaction done in the absence of SRF antibody was purified and used as a control to show total input DNA. The supernatant DNA was diluted 1:100 prior to PCR. One μl of each sample was subjected to PCR amplification. PCR analysis was carried out using primers from different regions of the SM-MHC gene and promoter regions of a number of control genes that are silent in SMCs (skeletal α-actin, insulin and β-globin). The sequences of PCR primers are shown in table 1. Following 32 (all primer sets except insulin) or 35 cycles (insulin) of amplification, PCR products were run on 2% agarose gels and analyzed by GelStar (BMA) staining. As additional controls, the promoter regions of the genes either silent or lacking CArG elements were also amplified by PCR. The PCR samples of these promoters showed a low level of background chromatin immunoprecipitation. The sequences of the PCR primers were the following; insulin, 5'-GCCAAAACTCTAGGGACTTTAGGAAG GATG-3' (SEQ ID NO:10), 5'-GCCGGGCAACCTCCAGT GCCAAG GTCTGAAGATC-3' (SEQ ID NO:11); β-globin, 5'-CAGCGTTTTCTTCAGAGGGAGTACCCAGAG-3' (SEQ ID NO:12), 5'-TCAGAAGCAAATGTGAGGAGCG ACTGATCC-3' (SEQ ID NO:13); skeletal α-actin, 5'-CAG GCTGAGAAGCAGCCGAAGGGACTCTAG-3' (SEQ ID NO:14), 5'-ACCTCCACCCTACCTGCTGCTCTGACT CTG-3' (SEQ ID NO:15); SM-MHC -4000, 5'-ATGTCA GATGTCCTCTCACTGCTTTATTCC-3' (SEQ ID NO:21), 5'-AGCAAACAGCTTTAAATACGTATTGGCTTC-3' (SEQ ID NO:22); 5'-CArG, 5'-CTGGAGCTCTTATTAGTA CTGGGGTCCC-3' (SEQ ID NO:18), 5'-ACTCAGGCC ATAAAAGGAAGTCGAGGCAGAGTTGG-3' (SEQ ID NO:19); intronic CArG, 5'-GGC CAAGCCACCCTGGA GAAACCTGGAC-3' (SEQ ID NO:20), 5'-CCCAGAA CTCAAGCCAGTCAGGCTGCATCG-3' (SEQ ID NO:23). Due to the relatively low resolution of ChIP method, we designed the PCR primers for the 5'-flanking CArG region for amplification of the region containing both CArG1 and CArG2.

Example 2

SMC-Specific Expression in Transgenic Mice: Indispensable Elements in SM-MHC First Intron It has previously been reported that an SM-MHC promoter DNA fragment extending from −4220 to +88 was capable of directing high-level expression in cultured rat aortic SMC. Madsen C. S. et al., 1997, *J. Biol. Chem.*, 272:6332–6340. When tested in bovine endothelial cells, L6 myoblasts and L6 myotubes, the activity of this construct was determined to be negligible. To determine if this same promoter/DNA fragment was capable of directing SMC-specific expression in vivo, this fragment was sub-cloned into a pBS-lacZ reporter gene construct (p4.2-lacZ) and tested for activity in transgenic mice. Thirteen independent transient transgenic mice harboring the p4.2-lacZ transgene were generated and analyzed for lacZ expression at multiple embryological stages ranging from embryonic day ("E") 13.5 to 19.5. No transgene expression was detected in any of the transgenic mice. These data show that, in contrast to activity levels observed for cultured SMC, the SM-MHC promoter fragment present within the p4.2-lacZ construct did not contain sufficient DNA for directing SMC-specific expression in transgenic mice.

It is well documented that cis-elements important for gene expression can be found outside the 5'-flanking region. Furthermore, they can be found within intronic regions.

Because 4.2 kb of 5'-flanking DNA was found to be insufficient for expression in vivo, a larger construct with added intronic sequences was tested. A rat genomic phage library was screened and one recombinant clone was identified whose insert contained 4216 bp of 5' flanking region, 88 bp of the first exon, which is untranslated sequence, and an additional 11,795 base pairs of first intronic sequence (total span: −4,216 to +11,795). This fragment, which was essentially identical to the p4.2-lacZ construct with respect to the 5'-flanking sequence and with respect to the presence of the 88 bp of 5' untranslated sequence, was isolated from the lambda phage by SaII digestion and sub-cloned into the pBS-lacZ vector to create the SM-MHC-reporter gene plasmid p4.2-Intron-lacZ.

Figure 2:
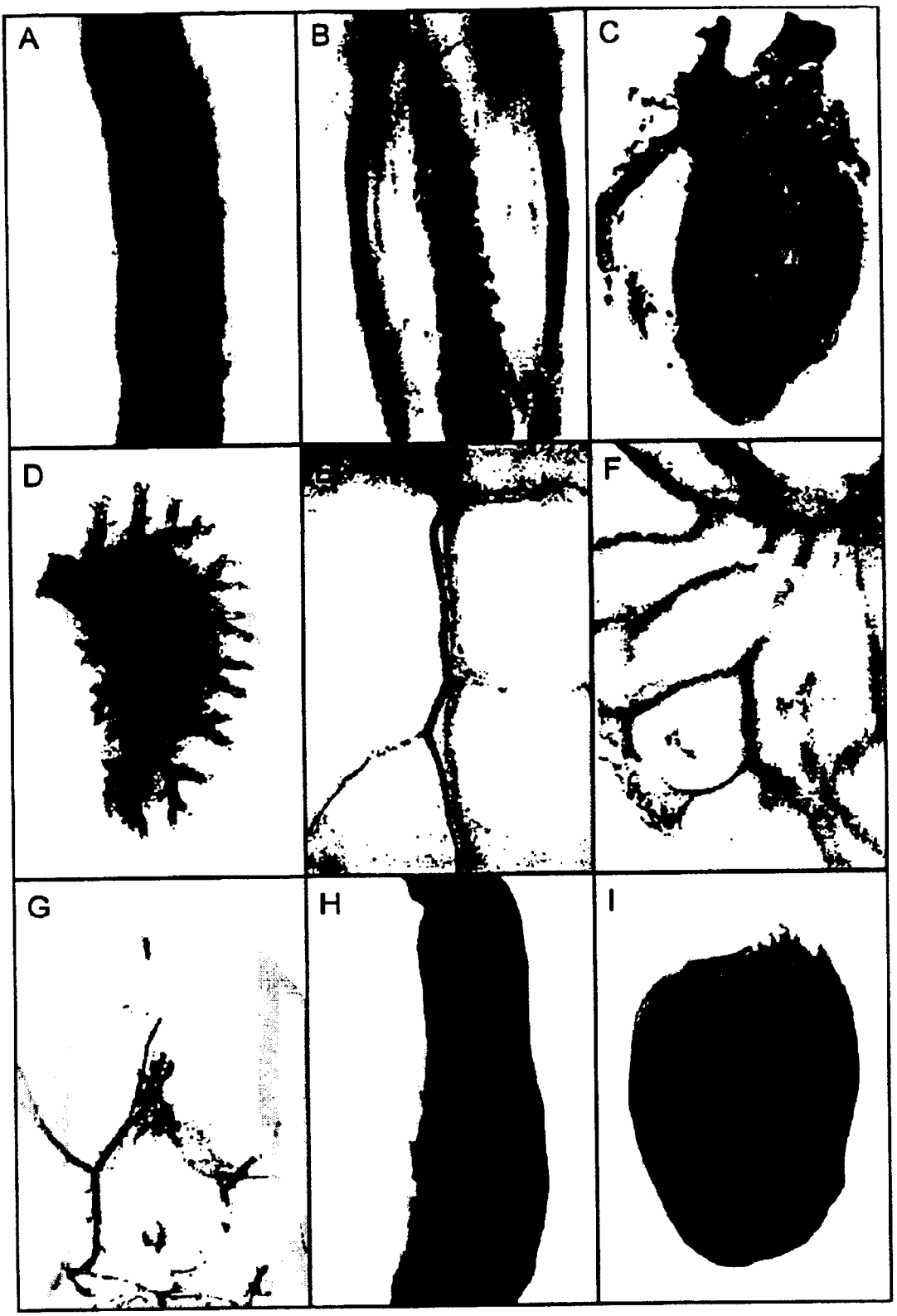
FIG. 2 shows analysis of the SMC specificity of the rat SM-MHC promoter in various SMC tissues of transgenic mice in vivo using a cre recombinase indicator system. Transgenic mice carrying a SM MHC-cre recombinase gene were crossed to an indicator line containing a lox p (the cre recognition site) flanked stop codon inserted upstream of a lacZ reporter gene that was inserted into the ubiquitiously expressed ROSA gene locus by homologous recombination (the mouse is designated R26R). Results showed expression of the lacZ indicator gene in virtually all SMC tissues. These results thus provide extremely compelling evidence for the SMC specificity of the −4.2 to +11.6 SM MHC promoter, since this assay system is far more sensitive in detecting reporter expression than conventional direct reporter systems in that even transient activation of the promoter is detected. That is, once cre recombination occurs there is permanent activation of the lacZ reporter. These results also establish the feasibility of using the SM MHC promoter in conjunction with cre recombinase and conditional (e.g. tetracylcine etc.) gene regulatory systems for purposes of achieving SMC specific gene targeting that is regulatable. A1-Thoracic aorta from a SMMHC-cre X R26R mouse; B-Trachea and carotid arteries; C-Heart; D-Lung; E-Skeletal muscle arteriole; F-Mesenteric vessels; G-Ventral surface of cerebrum; H1-Jejunum from a SMMHC-cre X R26R mouse; I-Bladder. The results provide rigorous assessment of the complete SMC specificity of the SM MHC promoter.
Figure 12:
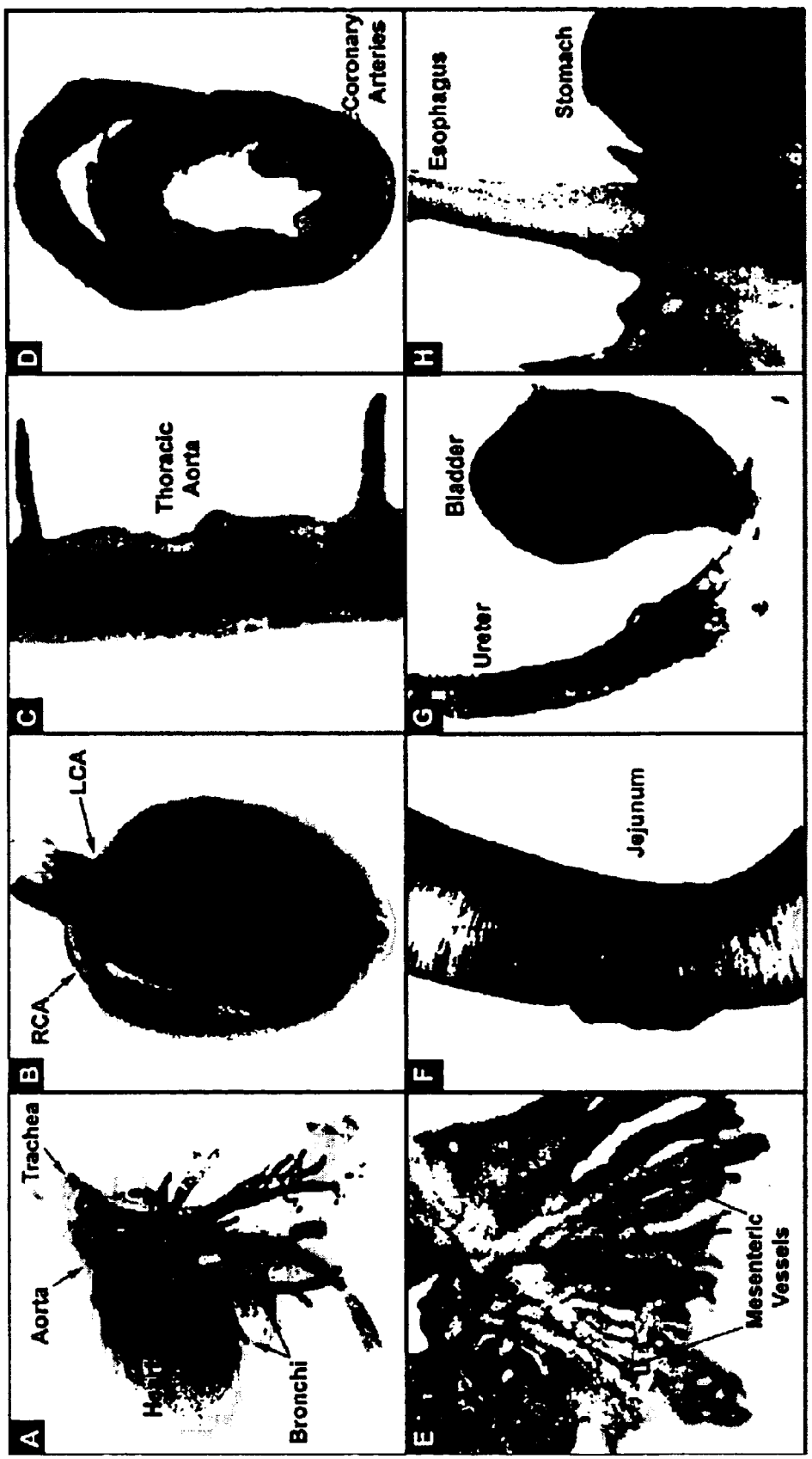
FIG. 12 shows gross examination of SM-MHC 4.2-Intron-lacZ expression in various smooth muscle containing tissues. Transgenic mice (5–6 week-old) were perfusion fixed with a 2% formaldehyde/0.2% paraformaldehyde solution and various smooth muscle containing tissues were harvested and stained overnight at room temperature for β-galactosidase activity using 5-bromo-chloro-3-indolyl-β-D galactopyranoside (X-Gal) as the substrate.
Figure 13:
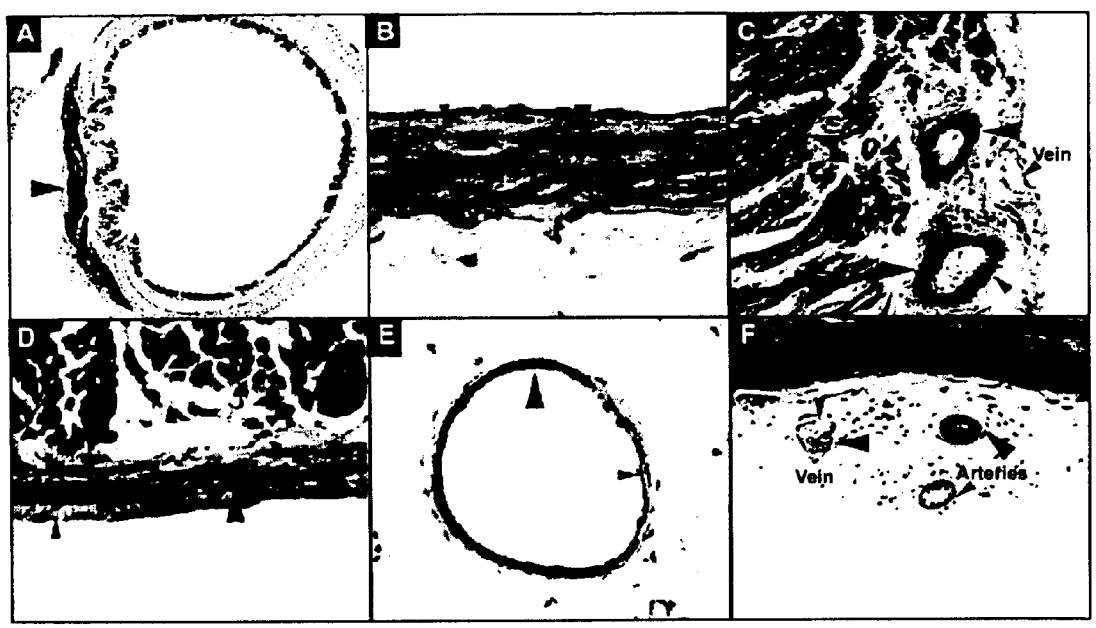
FIG. 13 shows histological analysis of rat SM-MHC 4.2-Intron-lacZ expression in various smooth muscle containing tissues. Transgenic mice (5–6 week-old) were perfusion fixed with a 2% formaldehyde/0.2% paraformaldehyde solution and various smooth muscle containing tissues were harvested and stained overnight at room temperature for β-galactosidase activity using 5-bromo-chloro-3-indolyl-β-D-galactopyranoside (X-Gal) as the substrate. After staining with X-Gal overnight, tissues were processed for paraffin embedding, sectioned at 6μm, and sections counterstained with hematoxylin/eosin.

The reporter gene p4.2-Intron-lacZ was used to generate four independent transgenic mice; one mouse was sacrificed at E13.5 for transgene expression analysis, and the other three were established as stable transgenic founder lines (designated as 2282, 2642 and 2820) that were utilized for analysis of transgene expression throughout embryological development and early adulthood. Analysis of adult mice generated from the three stable founder lines showed that lacZ transgene expression was essentially identical between the three founders and completely restricted to smooth muscle (FIGS. 1, 2 and 12). Gross examination of the heart and lung region excised from a 5 week-old p4.2-Intron-lacZ mouse revealed that transgene expression was present in the descending thoracic aorta, coronary arteries, trachea and bronchi (FIG. 12, Panel A). Transgene expression was not detected in any non-smooth muscle tissues in this region, such as heart muscle and lung tissue. Of note, transgene expression also was not detected in several smooth muscle containing tissues in this region including the esophagus and branches of the pulmonary artery, although expression was seen in the pulmonary artery outflow tract. Transgene expression was readily detectable in the major branches of the coronary arterial tree including the left and right coronary arteries (FIG. 12, Panel B), as well as the small coronary arteries and arterioles (FIG. 12, Panel D) of 5–6 week old transgenic mice. However, no lacZ expression could be detected in any of the coronary veins (FIG. 12, Panels B and D; and FIG. 13, Panel C). Transgene expression also was readily detected in the descending thoracic aorta, and intercostal arteries (FIG. 12, Panel C), as well as throughout blood vessels in the extremities and main body trunk, including small arteries, arterioles and veins such as the mesentery vessels (FIG. 12, Panel E). Expression of the lacZ transgene was readily detectable also in the visceral smooth muscle of the intestine (FIG. 12, Panel F), the ureter and bladder (FIG. 12, Panel G), the stomach (FIG. 12, Panel H) and the uterus and gallbladder. Thus, these initial analyses demonstrated that the p4.2-Intron-lacZ construct contained sufficient DNA for expression in all SMC tissue types, although certain SMC tissues were negative, at least in 5-6 week old animals. Moreover, certain smooth muscle tissues such as the aorta (FIG. 12, Panel C), intercostal arteries (FIG. 12, Panel C), jejunum (FIG. 12, Panel F) and stomach (FIG. 12, Panel H) clearly showed a mosaic pattern of transgene expression that was visible even at the gross tissue level.

Figure 3:
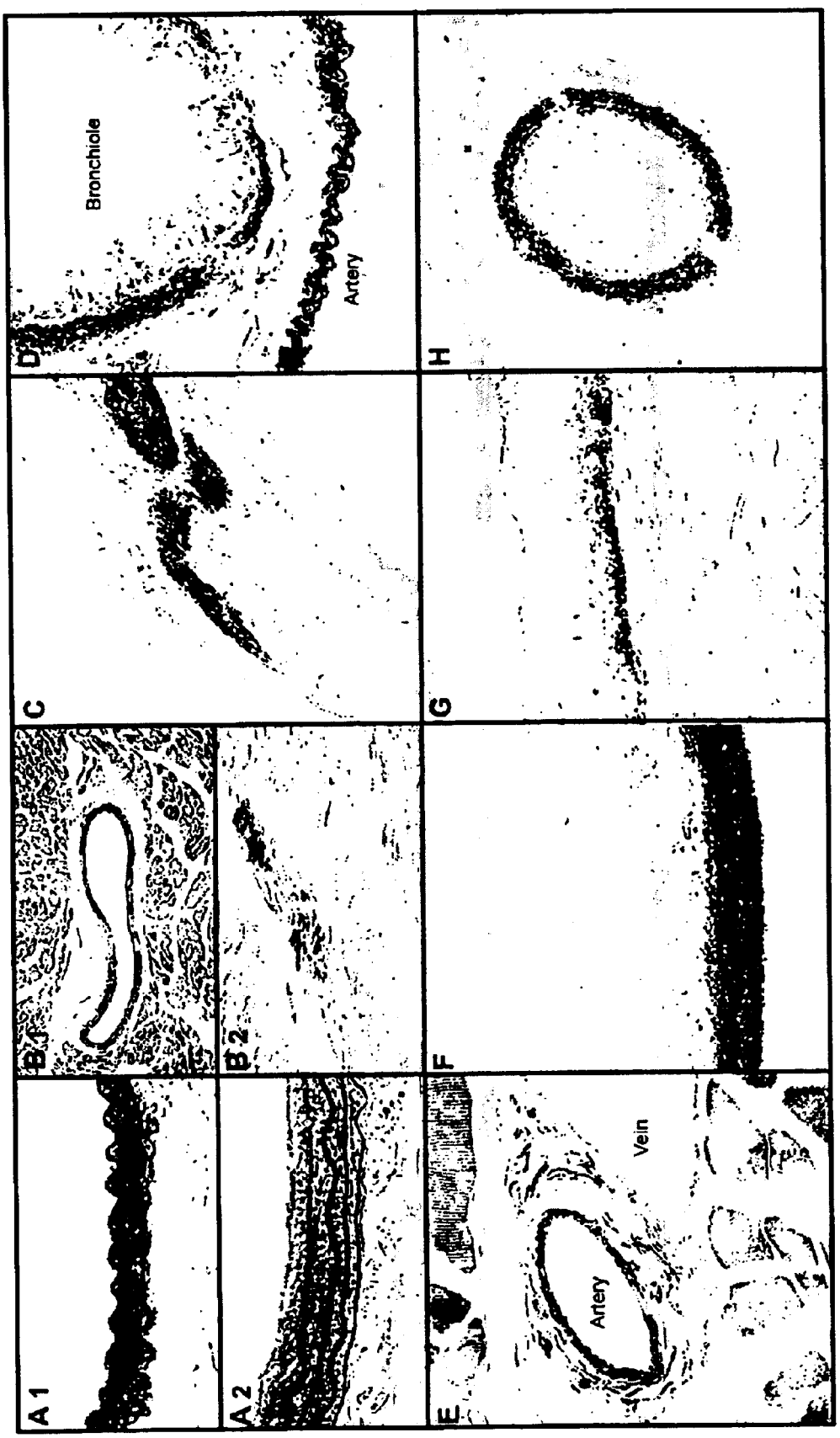
FIG. 3 shows histological assessment of LacZ expression in the SMC tissues shown in FIG. 2 showing the remarkable SMC specificity of expression of the −4.2 to +11.6 SM-MHC promoter. The results showed complete specificity of expression of LacZ within SMC with the exception of a very small population of atrial myocytes that show transient activation of the promoter during early heart formation (see reference {6812} f). A1-cross section of carotid artery; A2-cross section of aorta; B1-cross section of intramyocardial artery; B2-staining of a small population of cardiac myocytes; C-cross section of trachea; D-cross section of lung showing both bronchiole and pulmonary artery staining; E-skeletal muscle arteriole and venule; F-cross section of jejunum; G-cross section of esophagus; H-cross section of ureter.
Figure 5:
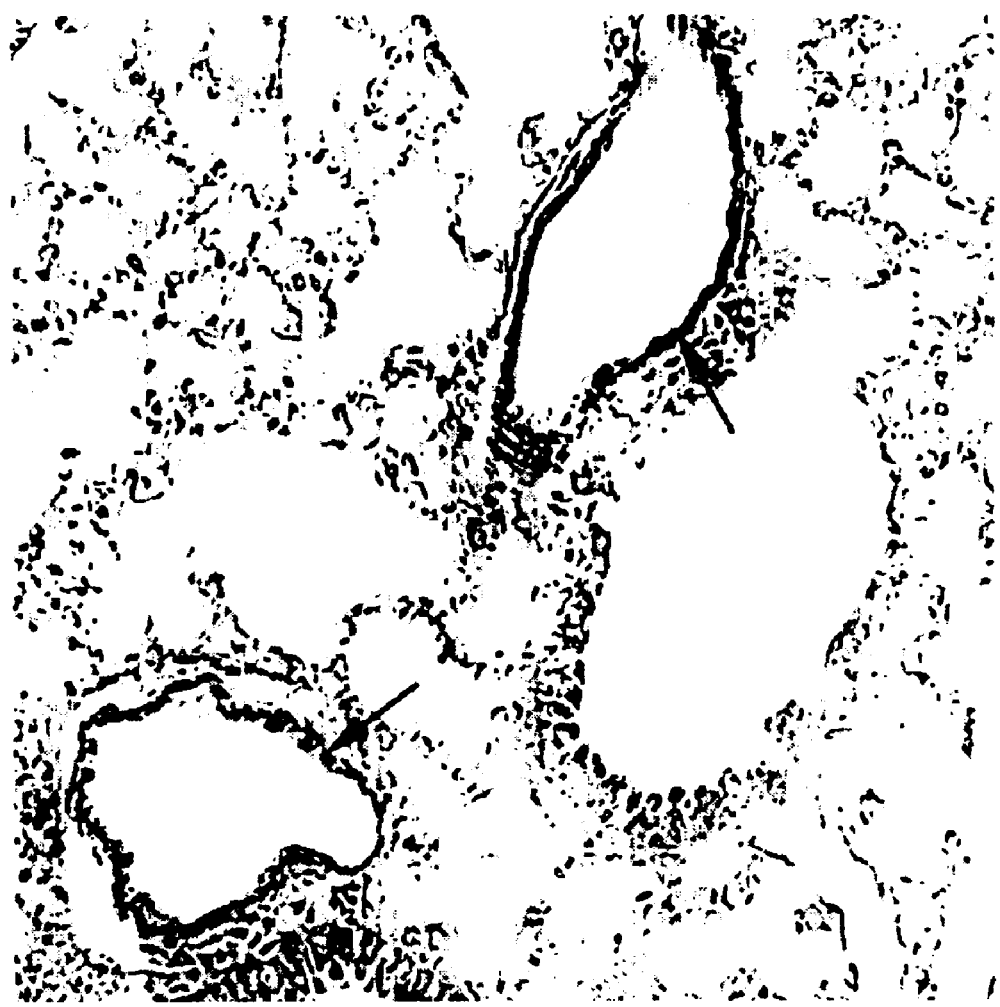
FIG. 5 shows histological section of the −4.2 to +5.3/+7.5 to +9 SM-MHC promoter showing high specificity of expression in pulmonary arteries and arterioles (see arrow).
Figure 6:
FIG. 6 shows expression of the −4.2 to +2.5 and +5.3 to +11.6 SM-MHC LacZ gene in tissues of adult transgenic mice. As seen, this SM MHC promoter reporter construct retained high level expression in the pulmonary airways, and aorta but diminished expression in the coronary arteries as compared to the wildtype −4.2 to +11.6 SM MHC LacZ transgene construct (see FIGS. 1–3). There was also high level expression in pulmonary vascular SMC based on histological analyses (data not shown). The results indicate high activity in pulmonary artery SMC, airway SMC, and the aorta, but virtually no activity in coronary artery SMC.

To assess transgene expression at the cellular level, histological analyses of lacZ reporter expressions were performed (see, e.g., FIGS. 3 and 13). Results of these studies further demonstrated that transgene expression was highly restrictive to smooth muscle. For example, analysis of the bladder and airway smooth muscle (FIG. 13, Panel A) showed that transgene expression was highly specific and appeared to be present in virtually all SMC located within these tissues. Likewise, SMC within many smooth muscle tissues including the aorta (FIG. 13, Panel B), coronary vessels (FIG. 13, Panel C), the intestine (FIG. 13, Panel D), stomach and many smaller blood vessels including small arteries, arterioles, veins, and venules (FIG. 13, Panels E and F) showed clear evidence of expression of the transgene within SMC, although some heterogeneity of expression was evident between adjacent cells.

Taken together, these results indicate that although the p42-Intron-lacZ transgene exhibited SMC-specific activity and was expressed in all major SMC types, it exhibited differences in activity in subsets of SMC both within and between different adult SMC tissues. Nevertheless, expression of the p4.2-Intron-lacZ transgene was present only in SMC, and not in any non-SMC.

Example 3

Transgene Expression in the Developing Embryo

Figure 14:
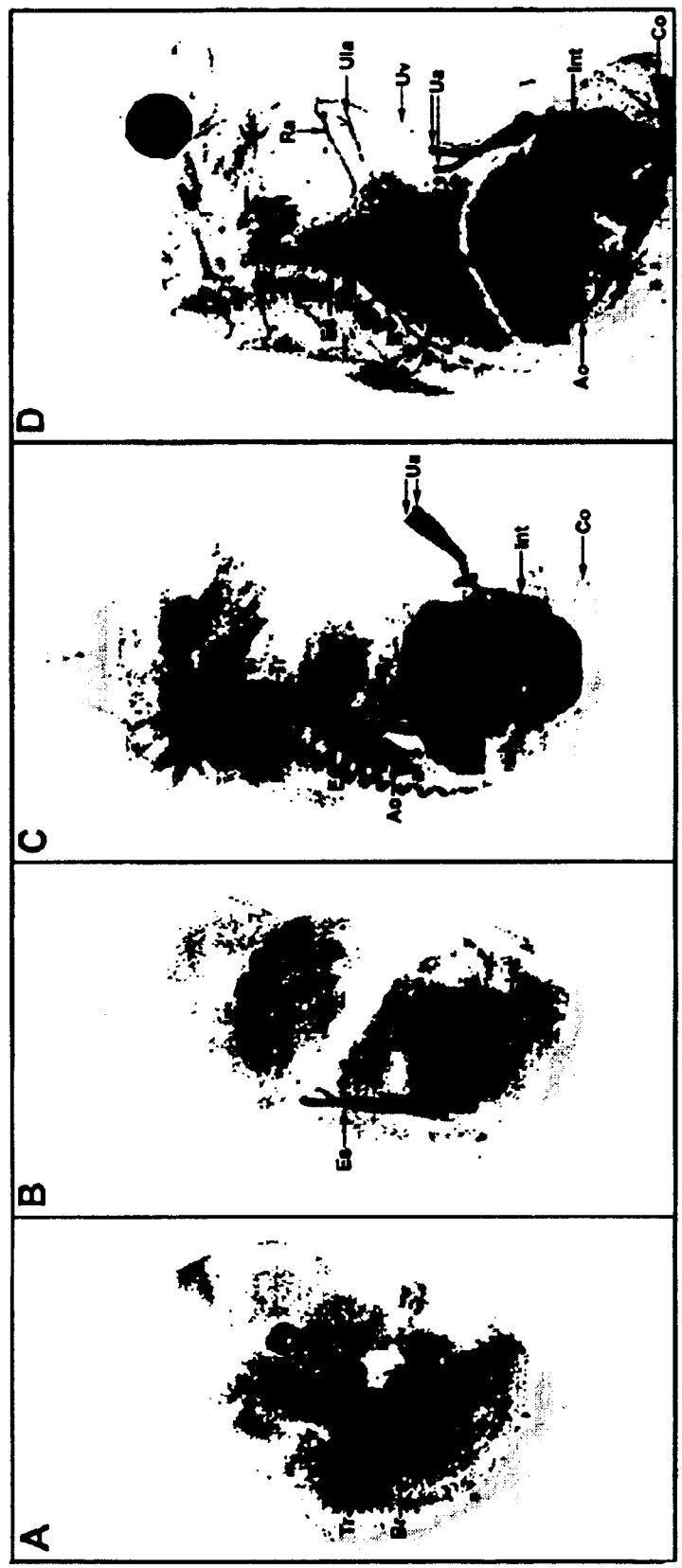
FIG. 14 shows expression of SM-MHC 4.2-Intron-lacZ throughout development. Embryos were harvested at various time points (10.5–16.5 days p.c.), fixed with a 2% formaldehyde/0.2% paraformaldehyde solution and stained overnight at room temperature for β-galactosidase activity using 5-bromo-chloro-3-indolyl-β-D galactopyranoside (X-Gal) as the substrate. Embryos were then cleared in benzyl benzoate:benzyl alcohol (2:1). Panel A: 10.5 days p.c. Panel B: 12.5 days p.c. Panel C: 14.5 days p.c. Panel D: 16.5 days p.c.

To determine if expression of the p4.2-Intron-lacZ transgene resembled the developmental expression pattern of the endogenous SM-MHC gene, embryos from the three stable founder lines were obtained at various stages throughout development [embryonic day E10.5 through E19.5] and analyzed for lacZ expression. Additionally, one transient founder was generated and analyzed for transgene expression at E13.5. With the exception of transient expression in the heart (B 12.5 to E17.5) of one of the stable lines which was localized to the myocardium, transgene expression patterns were essentially identical in all four independent transgenic lines (i.e. one transient transgenic mouse and three stable founder lines), and restricted to SMC. Transgene expression patterns of embryos derived from stable founder lines 2282, 2642 and 2820 are presented in FIGS. 14 and 15. The earliest developmental stage at which transgene expression could be detected was E12.5, where lacZ expression was readily identified in the trachea and bronchi (FIG. 14, Panels A and B). By E14.5, transgene expression was detectable in the bronchi, intestine, stomach, trachea and the aorta as well as a few other vessels throughout the embryo (FIG. 14, Panel C). Of particular interest, although transgene expression was virtually absent in the esophagus in the adult (FIG. 12, Panel H), its expression was clearly evident in embryos. At E16.5 transgene expression was more pronounced in the aorta than at earlier developmental time points, although it had a variegated and less intense appearance relative to other smooth muscle tissues (FIG. 14, Panel D). Additionally, the frequency of vessels that were positive for transgene expression was higher in peripheral vessels, and particularly those located in the extremities of the animal.

Figure 15:
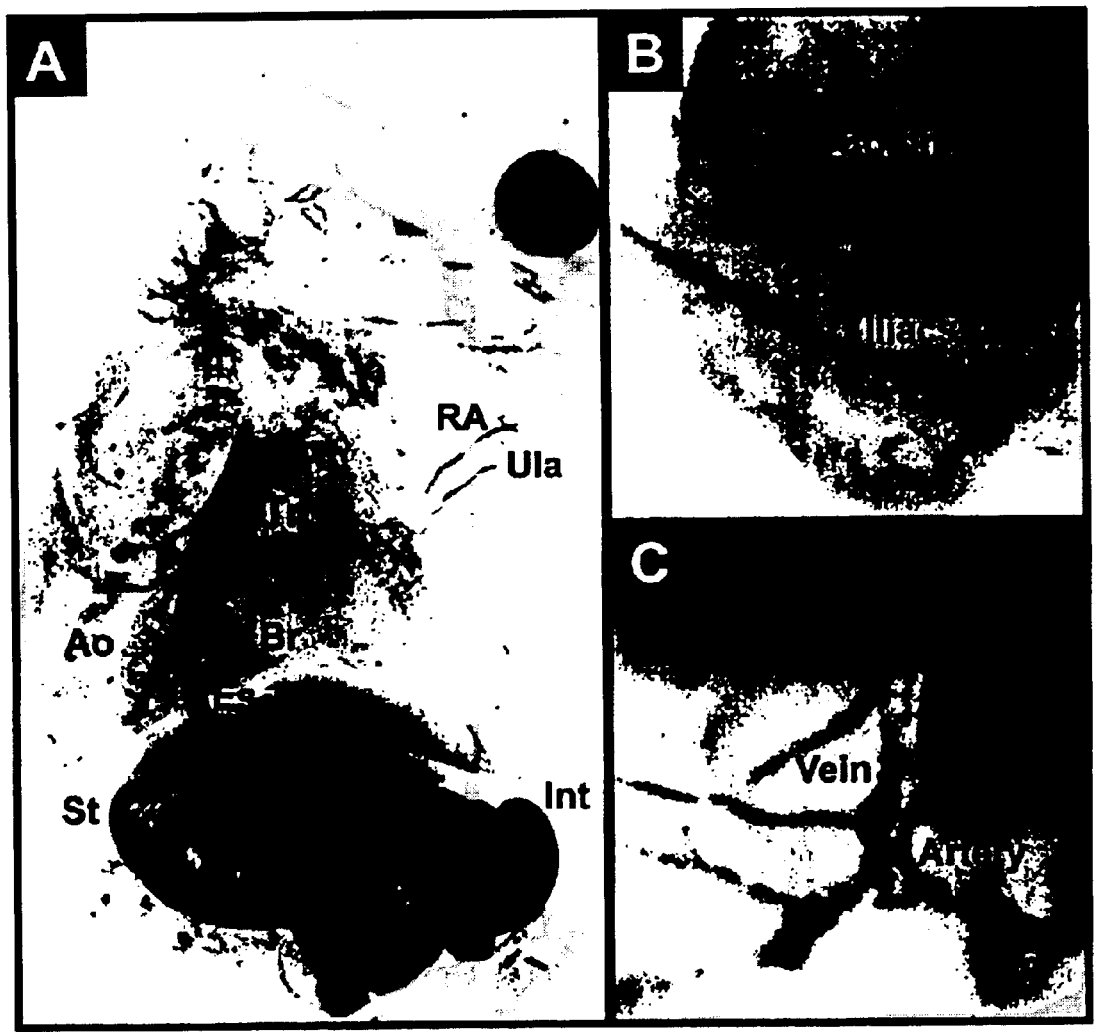
FIG. 15 shows expression of SM-MHC 4.2-Intron-lacZ at 19.5 days p.c. Embryos were harvested at 19.5 days p.c., fixed with a 2% formaldehyde/0.2% paraformaldehyde solution and stained overnight at room temperature for β-galactosidase activity using 5-bromo-chloro-3-indolyl -β-D-galactopyranoside (X-Gal) as the substrate. Embryos were then cleared in benzyl benzoate:benzyl alcohol (2:1). Panel A: Saggital section of 19.5 day embryo. Panel B: Closeup of thoracic cavity. Panel C: Iliac artery and vein.
Figure 16:
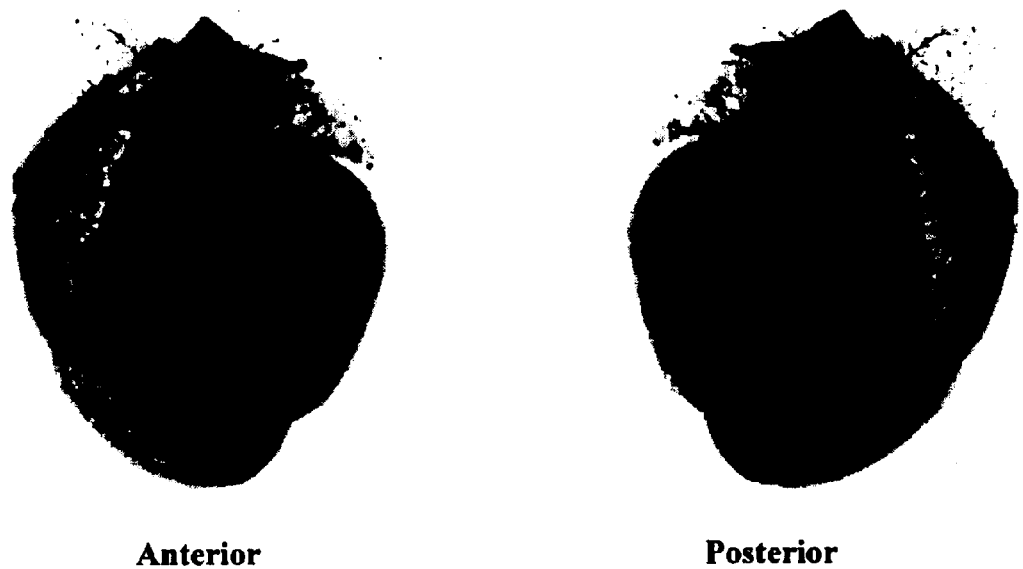
FIG. 16 shows expression of the SM-MHC 4.2-Intron-lacZ transgene in the coronary circulation of the heart of an adult mouse. High levels of SMC-specific expression are present in all major coronary arteries and arterioles.

One of the most notable differences between the E16.5 and E19.5 embryos was a marked increase in the frequency of vessels that stained positive for lacZ expression (FIG. 15). However, lacZ expression remained undetectable in a number of vessels. Especially conspicuous was the general absence of expression in the large blood vessels in the head and neck region including the internal and external carotid arteries, the jugular vein and the cerebral arteries and veins. However, many smaller sized blood vessels were positive for transgene expression in the head and neck region. Transgene expression was readily detectable also in many other arteries and veins throughout the body including the iliacs (FIG. 15, Panel D), the caudal artery and vein, the femoral artery, the umbilical artery and vein, the ulnar and radial arteries and superficial arterioles and venules within the musculature of the thoracic cage (FIG. 15).

Although expression levels in these types of studies are not quantitative, it is worth noting that levels of lacZ staining within the aorta did not appear to be as intense as compared to many other blood vessels and visceral smooth muscle tissues. In summary, results of these embryological studies support the data gathered from analysis of transgene expression in juvenile and adult mice, and show that p4.2-Intron-lacZ contains sufficient DNA for directing SMC-specific expression in all SMC-tissue types. However, results leave open the possibility that additional genomic regions may be required for SM-MFIC expression in some subsets of SMC. Nevertheless, these results demonstrate that the p4.2 Intron-lacZ transgene is capable of conferring SMC-specific gene expression in vivo.

Example 4

Multiple CArG Elements Define SM-Subtype Specificity of SM-MHC In Vivo

1. Plasmids Construction and Transfection

Mutant transgenic constructs of SM-MHC CArG elements were made in the context of −4200 to +11600 promoter/intron LacZ transgene (SM-MHC 4.2+intron-LacZ plasmid; Madsen et al., Circ. Res. 82:908–17, 1998). For simplicity, this construct is referred to as SM-MHC −4200/+11600 LacZ in this paper. Site-directed mutagenesis was performed on small fragments subcloned in pBluescript II using GeneEditor (Stratagene). The integrity of mutated fragments was confirmed by sequencing, and the fragments were subcloned back into the parental plasmid. The resultant mutant transgenic plasmids were tested for integrity by sequencing and restriction enzyme mapping. To minimize the possibility of errors in DNA amplification, at least two independently constructed clones were tested for activity in cultured SMCs. Mutant sequences are the following: CArG1, ttCCTTTTATGG (SEQ ID NO:1) to ggATCCTATGG (SEQ ID NO:2); CArG2, CCTTTTTGGG (SEQ ID NO:3) to ATCCTTTGGG (SEQ ID NO:4); intromc CArG, CCTTGTATGG (SEQ ID NO:5) to AGGCCTATGG (SEQ ID NO:6).

The minimal thymidine kinase promoter taken from pBL-CAT5 (Boshart et al., Gene 110:129–30, 1992) was subcloned into pAUG LacZ. Subsequently a BstXI/BglI (+1447 to +1673) fragment of the SM-MHC first intron was subcloned into the TK LacZ vector so that the fragment was repeated three times upstream of the TK promoter (3xICR-TK LacZ).

Transfection of the plasmids was performed using DOTAP (Roche) as described previously (Madsen et al., J. Biol. Chem. 272:6332–40, 1997). At least two independent clones were used for transfection and: the transfection of each plasmid was done at least in duplicate. Reporter activity was assayed by using ONPG as a substrate (Manabe et al., Biochem, Biophys. Res. Commun. 239:598–605, 1997). The activity was normalized to the protein concentration of each cell lysate as measured by DC protein assay kit (BioRad). The endogenous β-galactosidase activity was determined by transfecting a nonfunctional DNA (pBluescript II) and was subtracted from the measured activity of each construct. Subsequently the activity was normalized to that of promoterless construct, pAUG LacZ. One-way analysis of variance followed by Bonferroni method was used for data analysis. Values of p<0.05 were considered statistically significant.

Transgenic mice were used to establish breeding founder lines. Transgenic mice were generated and analyzed as described above in Example 1. To determine possible positional effects of transgene insertional sites on transgene expression, multiple independent founder lines were analyzed for each transgene construct.

2. Preparation of Nuclear Extracts and Electrophoretic Mobility Shift Assays (EMSAs)

Transgenic mice were used to establish breeding founder lines. Transgenic mice were generated and analyzed as described above in Example 1. To determine possible positional effects of transgene insertional sites on transgene expression, multiple independent founder lines were analyzed for each transgene construct.

Preparation of nuclear extracts from cultured SMCs was performed as described in Madsen (1997). Nuclear extracts from rat tissues were prepared as described previously (Dignam et al., Nucleic Acids Res. 11:1475–89, 1983) with the following modifications. In brief, tissues were taken from male Sprague-Dawley rats. Non-SMC layers were removed from the aorta, stomach, and bladder and tissues were immediately frozen in liquid nitrogen. The frozen tissues were powdered and washed once with modified buffer A (10 mM HEPES, pH 7.9, 13 mM KCl, 0.1 mM EDTA, 0.5 mM DTT, 0.05% NP-40) with Complete EDTA-free protease inhibitor (Roche). The samples were resuspended in 10 ml of buffer A and incubated on ice for 5 min. The samples were centrifuged and resuspended in a 10 packed cell volume of buffer A. NP-40 was added to the final concentration of 0.3%. The samples were then homogenized using a Dounce homogenizer. Disruption of cell membranes was confirmed by microscopic observation. The centrifuged samples were resuspended in modified buffer C (20 mM HEPES, pH 7.9, 420 mM NaCl, 0.2 MM EDTA, 25% glycerol, 0.5 mM DTT, 0.01% NP-40, Complete EDTA-free) and incubated on ice with gentle agitation for 30 min. Cell debris was removed by centrifugation. The samples were changed for buffer and enriched using Ultrafree-4 concentrator (Millipore).

The sequences of sense strands of EMSA probes were the following; CArG1, 5'-gacttccttttatggcctga-3'(SEQ ID NO:7); CArG2, 5'-cctggccttttttgggttgtt-3'(SEQ ID NO:8); intronic CArG, 5'-catgcccttgtatggtagtg-3' (SEQ ID NO:9); EMSAs were performed as described in Manabe et al., supra. In brief, 20 kcpm of $^{32}$P-labeled probe was incubated with nuclear extracts in 20 μl of binding buffer (10 mM Tris-HCl (pH7.5), 50 mM NaCl, 0.5 mM DTT, 10% glycerol, and 0.05% NP-40) with 0.25 μg of poly (dI-dC) (dI-dC). Reactions were incubated on ice for 20 min. For supershift assays, 1 μl of anti-SRF antibody was added after the 20-min incubation period and the reactions were incubated for an additional 10 min. The reactions were run on 5% polyacrylamide gels.

3. The SM-MHC Contains Conserved CArG Elements Required for Maximal Promoter Activity in Cultured SMCs We first examined transcriptional activity of the first intron in cultured rat aortic SMCs by using a series of 3'-deletion constructs as a means to identify putative cis-regulatory elements that would subsequently be tested in vivo in transgenic mice. Deletion of the region from +2491 to +417 decreased activity significantly (56-fold vs. 17-fold activity over pAUG LacZ). To identify possible cis-elements in the region +2491 to +417, we further analyzed this region using finer deletion mutants. A series of finer deletion mutants was constructed in the context of 1346 bp of the 5'-flanking region and transfected into cultured SMCs (FIG. 18A). Significant reductions in reporter activity were observed when the sequence from +1617 to +1586 was deleted (FIG. 18A). Within this region there is a CArG-like element at +1599 that is also present at an equivalent region in the human SM-MHC intron (FIG. 18B).

Figure 19:
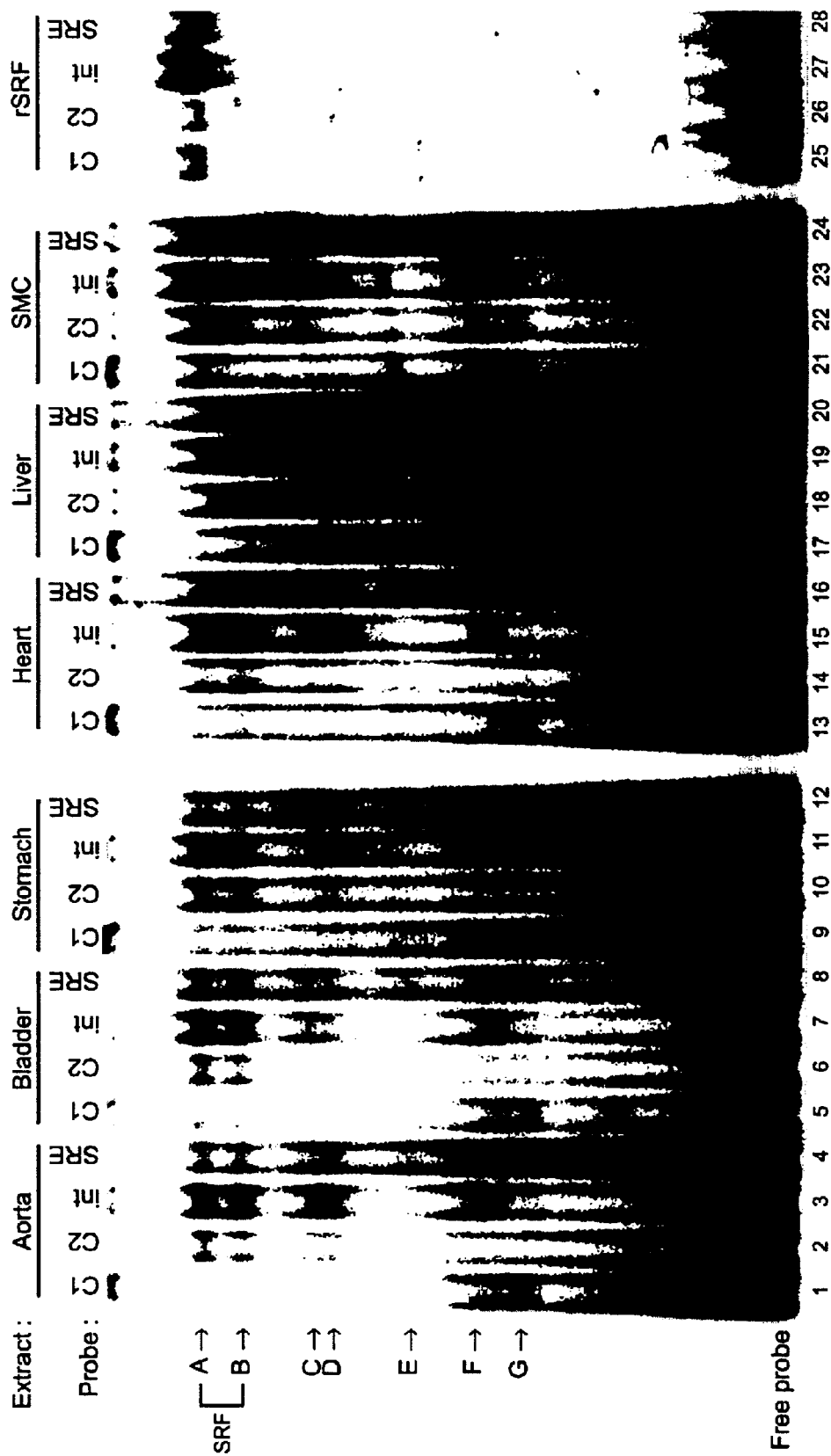
FIG. 19 show EMSA analysis of the CArG elements using tissue nuclear extracts. Radiolabeled 20-bp of double stranded oligonucleotides encompassing CArG1, CArG2, intronic CArG, and c-fos SRE were incubated with either nuclear extracts prepared from tissues or SMCs or recombinant serum response factor (SRF). The amount of nuclear extracts was determined to produce SRF shift bands of similar intensity: 4 μg of aortic; 3 μg of bladder; 3 μg of stomach; 7 μg of heart; 3 μg of liver; and 5 μg of rat SMCs nuclear extracts. One μl of programmed lysate of in vitro transcription/translation system (Promega) was used for recombinant SRF.

We have previously identified two CArG elements in the 5'-flanking sequence of the SM-MHC gene that are functional in the context of −1346 to +88 region in cultured SMCs (Madsen et al., J. Biol. Chem. 272:29842-51, 1997; and Madsen et al., J. Biol. Chem. 272:6332–40, 1997). However, since the 5'-flanking sequence alone is completely inactive in SMC in vivo in transgenic mice, it is critical to re-test the functionality of these cis-elements within the context of the −4200/+11600 LacZ construct previously shown to be active in SMCs in vivo (Madsen et al., 1998, supra). To ensure the efficacy of mutations in abrogating transcription factor binding, we first performed a series of EMSA experiments with each CArG element. Consistent with our previous results, both CArG1 and CArG2 probes bound SRF in nuclear extracts prepared from cultured SMCs (FIG. 19, lanes 21 and 22). In addition, as expected based on sequence analysis, the SM-MHC intronic CArG also exhibited SRF binding (FIG. 19, lanes 23, complexes A and B). Mutations of each CArG element completely abolished SRF binding activity in EMSAs. We then tested the effects of these same CArG mutations on transcriptional activity of the −4200/+11600 LacZ SM-MHC construct in cultured SMCs. The mutations of CArG1, CArG2, and intronic CArG reduced reporter activity by 46%, 49%, and 74%, respectively.

4. The Intronic CArG Confers SM-Type-Selective Transcription In Vivo

The data of transgenic mouse experiments clearly demonstrated that the intronic CArG element was necessary for transcription of the SM-MHC gene in the large arteries in vivo. As shown in FIG. 18B, we found that the region containing the intronic CArG is highly conserved between the rat and human genes. To test if the intronic region could work as a distinct transcriptional regulatory module in vivo, three copies of the 227-bp sequence containing the highly homologous region (+1447 to +1673) were cloned in tandem 5' to a minimal thymidine kinase (TK) promoter LacZ construct (3xICR-TK LacZ). The construct showed very high activity (13.7-fold activity over the minimal TK LacZ construct) in cultured SMCs. This construct was used to produce transgenic mice. In one founder line (line 7240) among four founder lines, very strong reporter expression was observed in vascular SMCs (see, FIG. 25). Another line (line 7249) also showed expression in SMCs although not as strong. The other two lines were negative for staining. Although two founder lines did not express the 3xICR-TK LacZ transgene; it seems unlikely that the cell restricted activity observed in lines 7240 and 7249 was due solely to locus dependent activation associate with the site of transgene insertion. Rather results support that the 227-bp intronic sequence can direct transcription at least in some SMCs in vivo when coupled with a minimal TK promoter.

Figure 25:
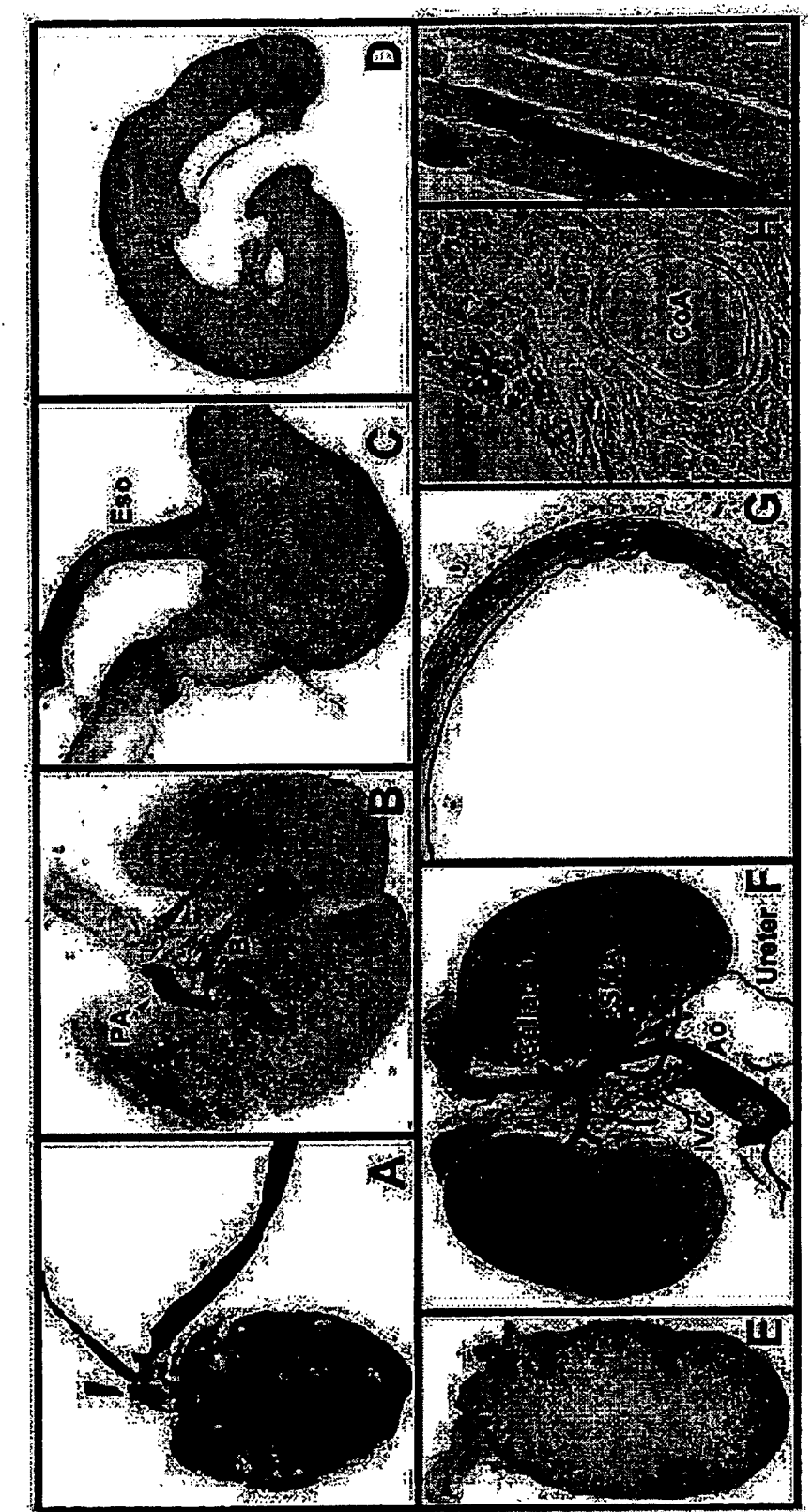
FIG. 25 shows transgene expression of the intronic CArG region-minimal TK-LacZ. Various tissues of 4-week-old transgenic mice and embryos of the 3xICR-TK LacZ line (7240) were stained for β-galactosidase activity. A, B, anterior view of the heart and lung; C, the esophagus, stomach, and duodenum; D, a part of small intestine; E, a cross section of the bladder; F, anterior view of the kidneys, ureter, abdominal organs and great blood vessels; G, histological examination of the thoracic aorta; H, pulmonary artery and bronchus; I, cardiac muscle, coronary artery and intercostal muscle of the 3xICR-TK LacZ transgenic mice. Ao indicates aorta; PA, pulmonary artery; SMA, superior mesenteric artery; IVC, inferior vena cava; H, heart; Br, bronchus; Eso, esophagus; Int, intestine; S, stomach; Bl, bladder.

In line 7240, reporter expression was particularly prominent in the large arteries including the aorta, carotid, and pulmonary arteries (FIG. 25, Panels A, B, F, G). Reporter expression was also strong in intermediate size arteries (FIG. 25, F). Transgene expression in smaller arteries was relatively weaker than that in large arteries and not all the smaller arteries were stained positive. Reporter expression was also observed in large veins including the vena cava (FIG. 25, F). While the expression in vascular SMCs was very strong, transgene expression was very weak in visceral SMCs. Only few cells were stained positive in the stomach, intestine, and bladder (FIG. 25, C–E). Interestingly, strong reporter expression was also observed in the heart and skeletal muscle. In the heart, while cardiac muscle cells were stained positive for β-galactosidase expression, no transgene expression was observed in SMCs in coronary vessels (FIG. 25, H). Various skeletal muscle cells also expressed the transgene (FIG. 25, I) The data provide evidence that the conserved region containing the intronic CArG is capable of driving transcription in subsets of SMCs in vivo but lacks the complete SMC-specificity seen with the endogenous SM-MHC gene and the −4200/+11600 LacZ transgene.

5. Differential Requirements of the CArG Elements in SMC-Subtypes In Vivo

Figure 20:
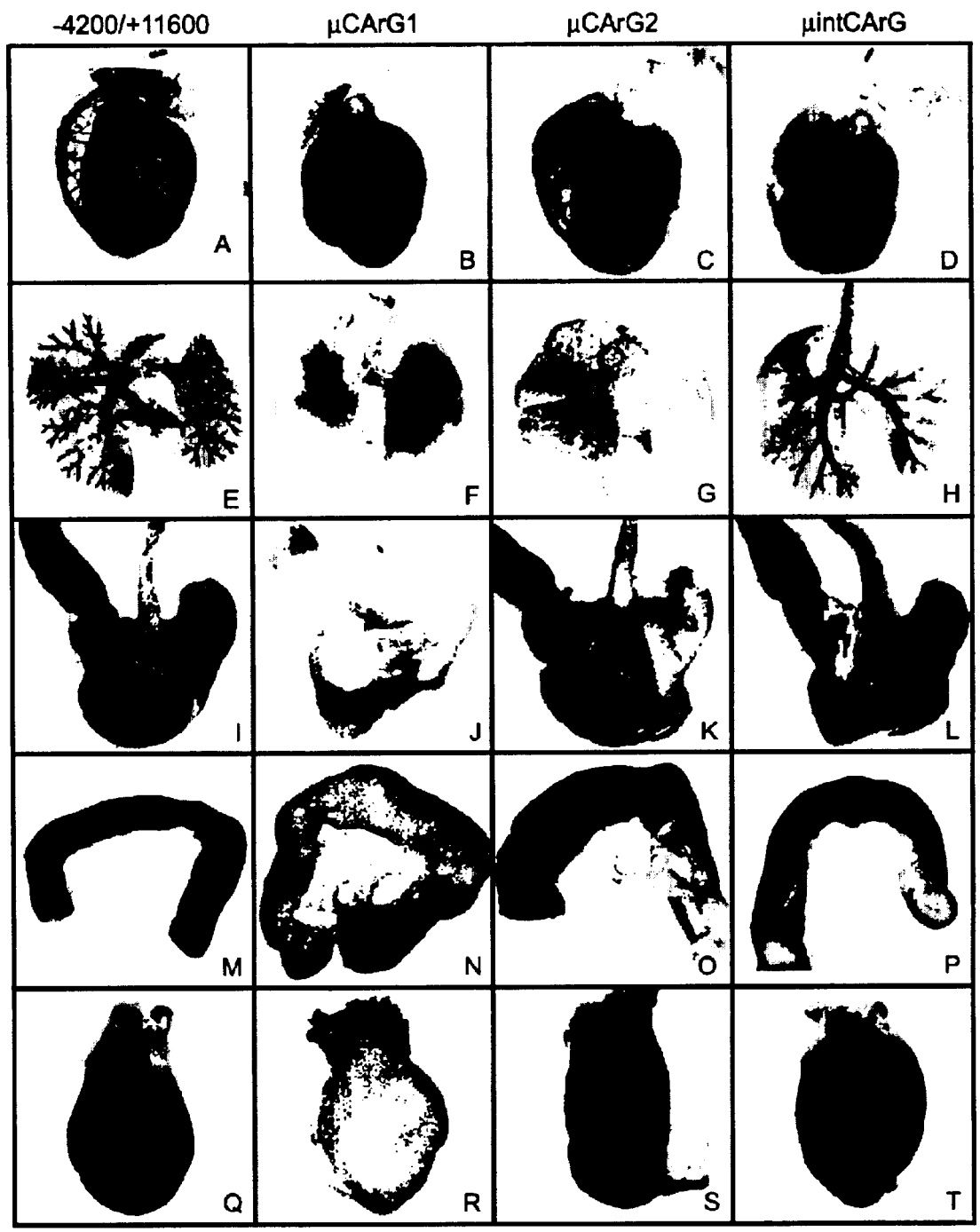
FIG. 20 shows macroscopic examination of reporter gene expression in wild-type and mutant SM-MHC LacZ transgenic mice. Four-to 6-week-old transgenic mice were perfusion-fixed with a 2% formaldehyde/0.2% glutaraldehyde solution. Pictures show LacZ reporter expression in various tissues from wild-type −4200/+11600 LacZ (A, E, I, M, Q), CArG1 mutant (B, F, J, N, R), CArG2 mutant (C, G, K, O, S), and intronic CArG mutant mice (D, H, L, P, T). A–D, anterior view of the heart and aorta. E–H, the lung. I–L, the esophagus, stomach, and duodenum. M–P, a portion of small intestine. Q–T, the bladder. Tissues were cleared by benzyl benzoate/benzyl alcohol in A–H.

In order to examine the functional roles of the CArG elements in vivo, the −4200/+11600 LacZ SM-MHC CArG mutant constructs were used to generate transgenic mice. The expression patterns observed are summarized in Table 1. Mutation of CArG1 resulted in abrogation of LacZ expression in all SM tissues in all three independent transgenic founder lines analyzed. In contrast, all three transgenic founder lines of the wild-type SM-MHC −4200/+11600 LacZ construct showed reporter expression in virtually all SM tissues (FIG. 20). These data clearly demonstrate that CArG1 was required for expression of the SM-MHC gene in vivo in all SM tissues.

Mutation of CArG2 resulted in differential reductions in reporter activity in SM tissues. LacZ expression in the gastrointestinal (GI) tract was decreased but was easily detectable in adult mice (FIG. 20, I, M vs. K, O). Expression in the bladder was similar to that observed in wild-type mice (FIG. 20, Q vs. S). No expression was observed in large blood vessels including the aorta, pulmonary, coronary, carotid, celiac, and femoral arteries, and the vena cava (FIG. 20, A, E vs. C, G). However, very weak reporter expression was observed in smaller arteries including small mesenteric arteries (data not shown). Mutation of CArG2 also virtually abolished expression in the trachea and bronchi (FIG. 20, E vs. G).

TABLE 1

Summary of report gene expression in SM-MHC LacZ transgenic mice

| construct | LacZ positive lines/founder lines | aorta | coronary artery | mesenteric artery | vena cava | airways | stomach | intestine | bladder |
|---|---|---|---|---|---|---|---|---|---|
| −4200/+11600 LacZ | 3/3 | ++ | ++ | ++ | ++ | ++ | ++ | ++ | ++ |
| CArG1 mutant | 0/3 | − | − | − | − | − | − | − | − |
| CArG2 mutant | 3/5 | − | − | ± | − | ± | + | + | + |
| intronic CArG mutant | 4/4 | − | + | ++ | ++ | ++ | ++ | ++ | ++ |
| 3xICR-TK LacZ | 2/4 | +++ | − | ++ | ++ | ± | ± | ± | ± |

Figure 21:
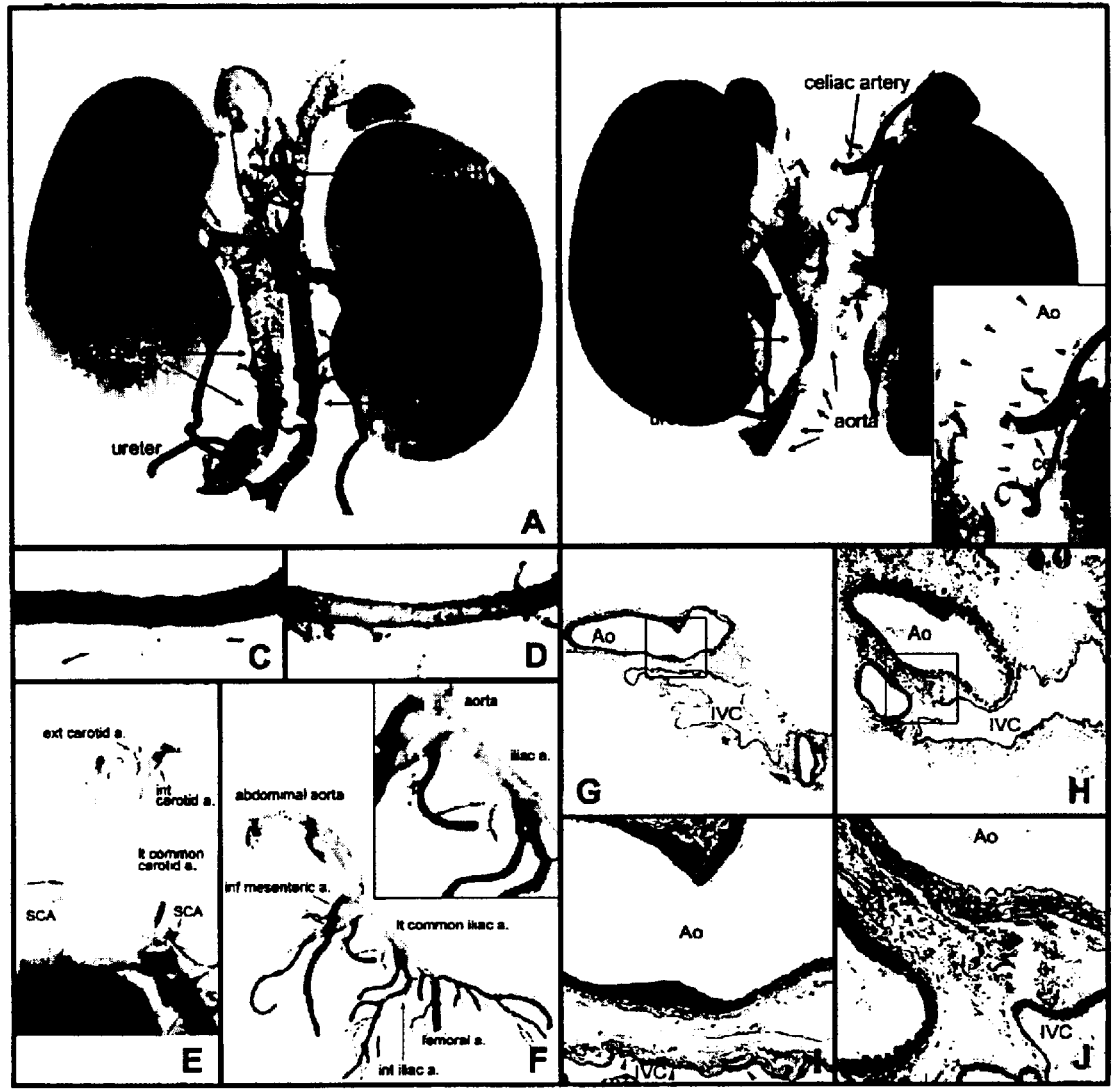
FIG. 21 shows large artery-specific silencing of the reporter gene in intronic CArG mutant mice. Abdominal organs removed en block showing reporter expression in the blood vessels and urinary tract in the wild-type (A) and intronic CArG mutant (B) transgenic mice. To better illustrate transgene expression in large arteries, several smaller arteries and connective tissues were removed and the tissues cleared. The supramesenteric artery, which was stained positive, was removed from the intronic CArG mutant mouse tissues. A portion of the tissues is expanded in the insert in panel B. Arrowheads indicate the position of aorta that is not visible because of the lack of staining. Note that the blood vessels within the kidneys were not stained in either wild-type nor intronic CArG mutants. C, D, the thoracic aorta and branching arteries of the wild-type (C) and the intronic CArG (D) mutant transgenic mice. E, view of the large arteries in the cervicothoracic region of the intronic CArG mutant transgenic mouse. F, the large arteries and their branches in the abdomen of the intronic CArG mutant. A portion of the arteries is expanded in the insert in F. G, H, I, J, histological examination of the abdominal aorta and inferior vena cava of the wild-type (G, I) and the intronic CArG mutant (H, J) mice showing abrogation of reporter expression in SMCs of the aorta in the intronic CArG mutants. Note that expression in the vena cava was not changed by the mutation. The boxed areas (G, H) are shown by a higher magnification (I, J). Ao indicates aorta; DA, ductus arteriosus; IVC, inferior vena cava; SCA, subclavian artery.

Mutation of the intronic CArG resulted in a vascular SMC-specific phenotype. Reporter expression in the GI tract, urinary tract and airways was equivalent to that of wild-type transgenic mice in adults and embryos of four independent intronic CArG mutant lines (FIG. 20, Panels B, I, M, Q vs. H, L, P, T). Expression in veins was also equivalent to that of the wild-type. However, expression in large arteries including the aorta, common carotid arteries and the main trunks of subclavian arteries was completely silenced in all lines (FIG. 20, A, E vs. D, H). Interestingly, the small branching arteries from the thoracic aorta including the intercostal arteries showed transgene expression equivalent to that of the wild-type (FIG. 21, C, D). In the carotid arteries no expression was observed in the proximal portion (FIG. 21, E), whereas in the distal common carotid arteries a few cells were stained positive, and the internal and external carotid arteries were strongly stained. Strong expression of the intronic CArG mutant was also observed in arteries in the head including the basilar artery, arteries of Willis ring, and cerebral arteries (data not shown). Reporter expression was not detected in the abdominal aorta, whereas the branching arteries from the abdominal aorta including the celiac, renal, and adrenal arteries were stained strongly positive (FIG. 21, A vs. B). Indeed, the abrupt transition in expression from non-detectable to a high level between the conduit arteries and branch arteries was quite remarkable (FIG. 21, B, F). Histological sectioning of blood vessels in the abdomen clearly showed selective abrogation of reporter expression in the aorta in intronic CArG mutant transgenic mice (FIG. 21, G–J). In the common iliac arteries expression was barely detectable, whereas expression was strong in their branches including the femoral arteries (FIG. 21, F).

Transgene expression in the coronary arteries was somewhat varied among the intronic CArG mutant lines presumably due to positional effects of transgene insertion sites. In two lines some expression was detectable in the coronary arteries, while little or no expression was observed in the other lines. However, even in the former two lines, overall transgene expression was clearly much weaker than that of the wild-type transgenic lines. Positive staining was restricted within the main trunks and a few major branches in the intronic CArG mutants, while in the wild-type expression was detectable in smaller branches. However, due to the qualitative nature of β-galactosidase staining and variability in expression level among the lines we could not conclude the extent of necessity of the intronic CArG in the coronary arteries.

Similarly, expression in the pulmonary arteries and veins was varied in mice containing the mutant intronic CArG transgene. Two lines, which showed transgene expression in the coronary arteries, had detectable transgene expression in the pulmonary blood vessels, whereas the other lines showed no expression. Even in two expressing lines, transgene expression was very weak, which made the staining of the lung look sparse as compared with that of the lung of wild-type mice as depicted in FIG. 20. However, microscopically some SMCs in the pulmonary blood vessels were stained positive (data not shown). Expression of the wild-type transgene in the pulmonary vessels was also somewhat varied among transgenic lines and the expression level, especially that in the pulmonary veins, was generally weak as compared with other vascular beds. Given the variability and weakness of transgene expression in the pulmonary circulation, no definite conclusions can be made regarding the role of the intronic CArG in pulmonary blood vessels, although results showing no expression in two founder lines suggests that it may have some function. Reporter expression in intronic CArG mutant transgenic mice showed that the intronic CArG was indispensable for transgene expression in large arteries, while it was dispensable in smaller arteries, veins and visceral SMCs. The large arteries that absolutely required the intronic CArG largely fit the classification of elastic artery.

Figure 22:
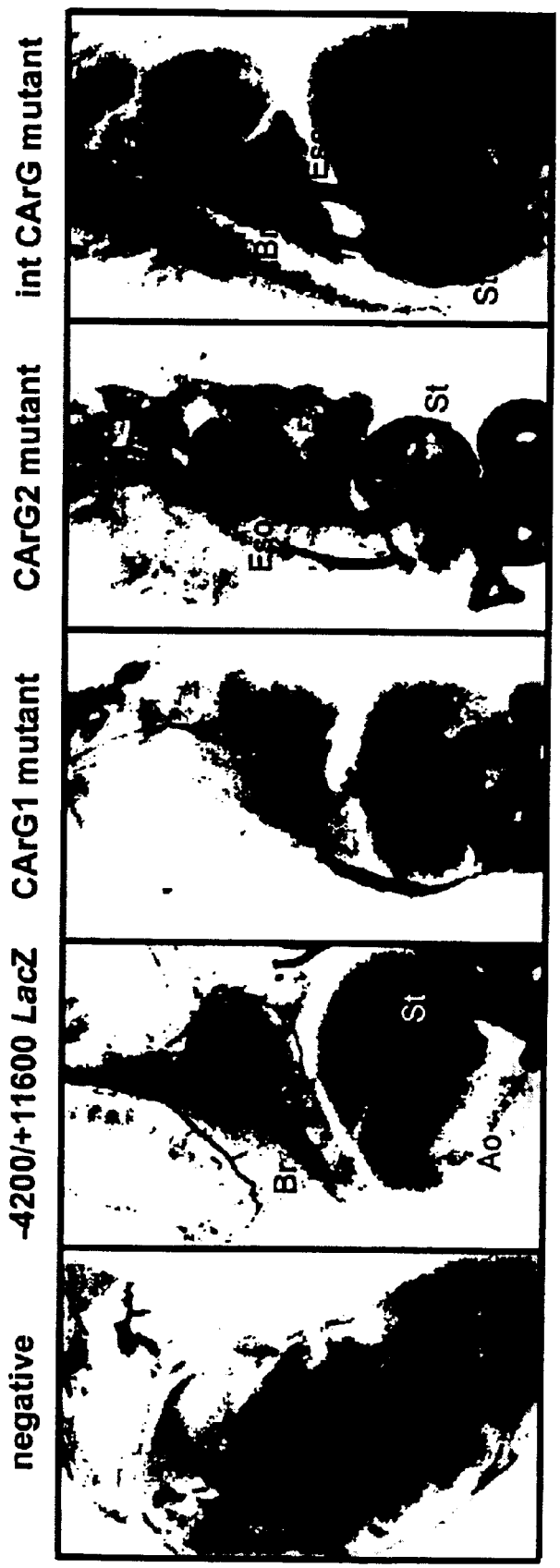
FIG. 22 shows transgene expression in embryos. Embryos were harvested at 19.5 dpc, skinned, and sectioned sagittally along the midline to permit dye penetration. The embryos were stained and cleared. The staining seen on the intestines in the negative and CArG2 mutant transgenic mice is due to endogenous β-galactosidase activity and limited within the epithelial layer. Ao indicates aorta; Eso, esophagus; H, heart; St, stomach; Tr, trachea.

The SM-MHC gene is a marker of later stage SM differentiation, and expression of the wild-type −4200/+ 11600 LacZ transgene was relatively weak in many SMC tissues until embryonic day (ED) 17.5–19.5. Thus, to facilitate analysis of effects of CArG mutations during development, we restricted analyses to ED 19.5. Results showed the transgene expression pattern in each CArG mutant transgenic mouse was largely consistent with that in adult mice (FIG. 22). No expression was observed in embryos of CArG1 mutant transgenic mice. In the CArG2 mutant transgenic mice, reporter expression was observed only in the GI tract. In intronic CArG mutant transgenic mice, the expression in the GI tract and airways was equivalent to that in the wild-type transgenic lines. While reporter expression in smaller arteries was easily detectable, no expression was detected in the large arteries in the intronic CArG mutant transgenic mouse embryos.

In summary, the transgenic mouse data demonstrate that each CArG element is differentially required in SMC-subtypes in vivo in transgenic mice. CArG1 is crucial for transcription in all SMCs; CArG2 is indispensable in large blood vessels but had a relatively minor role in the GI and urinary tracts; the intronic CArG is absolutely required only in large elastic arteries. Taken together, the results demonstrate the multiplicity of regulatory programs that control expression of SMC differentiation marker genes in vivo and indicate that each of the multiple CArG elements mediates distinct information for transcriptional regulation in different cell-types in vivo. In addition, the data indicate that the spatial and temporal regulation of SMC genes is not governed by a single regulatory region or an enhancer.

6. Discussions

The results of the transgenic mice of the CArG mutant constructs indicate that at least two regions (i.e., the 5'-flanking CArG and intronic CArG regions) are required for in vivo transcription of the SM-MHC gene. We are further mapping transcriptional regulatory modules in the SM-MHC gene locus. Preliminary data indicate that the 5'-flanking and first intron contain multiple positive and negative transcriptional regulatory regions, and that different SMC-subtypes require different subsets of modules (Manabe and Owens, unpublished observations). Why might SM-MHC transcription require such a complex transcriptional regulatory scheme in vivo?

It is evident that vascular SMCs within different vascular beds reside in vastly divergent local environments in vivo. Differences in the physiological role of vascular beds with respect to blood pressure, flow, and tone require very diverse vessel wall structures. SMCs are thus undoubtedly exposed to quite different vasoactive/neuronal stimuli and environmental cues from one vascular bed to another. If one considers the differences between vascular and visceral SMCs, the diversity is even more prominent, and it is well established that SMCs are derived from different embryological origins. Finally, one must also consider that the functions of SMCs can vary greatly during development and in adult animals due to their key role in matrix deposition, and vessel morphogenesis, as well as in vascular repair. Due to these many differences, SMCs in vivo need to respond to very diverse inputs (environmental cues) that activate various intracellular signaling pathways, and coordinately express necessary genes. It is thus conceivable that even to control the same gene, such as SM-MHC, SMC-subpopulations in different environments may need to utilize distinct sets of regulatory pathways. In other words, the SM-MHC gene regulatory program evolved so that it utilizes various regulatory pathways to control transcription in heterogenous extra-and intracellular environments. In fact, the differential requirement of the intronic CArG and CArG2 of the SM-MHC gene supports a hypothesis that distinct transcriptional regulatory programs are activated in SMC-subtypes.

One striking feature of the intronic CArG mutant was that the transgene was completely silent in the elastic arteries such as the aorta, whereas expression was easily detectable in the intermediate and small size arteries directly branched from the aorta. There are at least two possible explanations for the differential requirement of the intronic CArG that are not necessarily mutually exclusive. First, we need to consider the heterogeneity in the embryonic origin of SMCs between the large and smaller arteries. It has been postulated that SMCs have at least three embryonic origins: local mesenchymal cells, neural crest cells, and proepicardial cells. In the aorta, the aortic bulb and ascending aorta mainly consist of neural crest derived SMCs and the descending aorta mainly consists of mesenchymal derived SMCs. However, in intronic CArG mutant transgenic mice, SMCs in the aorta were stained negative irrespective of the position of the cells, and no known difference in lineage fits the distribution of the intronic CArG-dependency. Therefore, it is unlikely that differences in embryonic origin solely determined the requirement of intronic CArG for transcriptional control.

In addition, as discussed above, the heterogeneity in phenotype and function of SMCs in vivo is likely to require multiple transcriptional programs to control the same gene. The differences in the physiological functions of SMCs in elastic versus muscular arteries would also require SMCs to express distinct sets of genes to fulfill their functional roles. It is thus conceivable that the intronic CArG is integrated in a regulatory program that processes environmental cues unique to elastic arteries and controls gene expression important for the function of such vessels. A number of genes including ion channels, contractile proteins, growth factors/receptors, and transcription factors have been shown to be differentially expressed in vascular beds. For example, a transcription factor, CHF1 (Hrt2/Hey2/HERP1/gridlock) has been shown to be mainly expressed in the aorta. It would be of interest to compare the transcriptional regulatory mechanisms of these genes, and also to determine the function of differentially expressed transcription factors in control of SMC-subtype-selective gene regulatory programs.

Example 5

Figure 23:
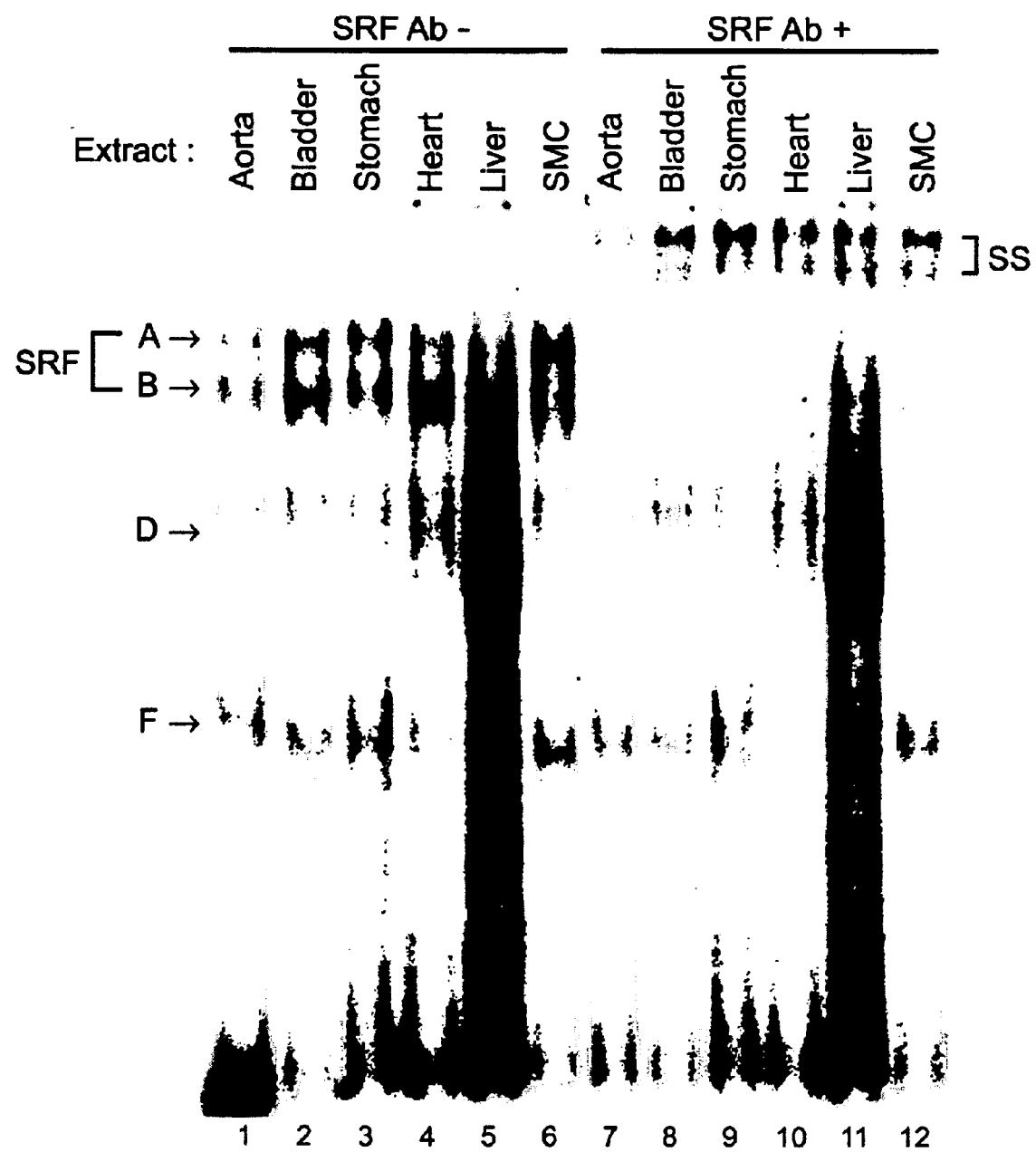
FIG. 23 shows supershift analysis of the intronic CArG-binding proteins. One μl of anti-SRF antibody was added to the binding reaction of an intronic CArG probe and nuclear extracts after 20 min of incubation on ice and the reactions were further incubated for 10 min on ice. Addition of the antibody resulted in supershift of SRF-containing complexes (A, B). Complexes A and B formed with other CArG probes used in EMSAs in FIG. 23 were also supershifted (data not shown). Arrows indicate supershifted complexes.

SRF Interaction with SM-MHC CArG Elements
1. SMCs in Intact Tissues Expressed SRF and other Proteins that Bind to CArG Elements As an initial step to determine mechanisms that control SMC-subtype-specific transcriptional regulation through multiple CArG elements, we examined protein binding properties of each CArG element using EMSAs. Since there were no SMC culture cell lines that had been shown to faithfully emulate differentiated phenotypes of SMC-subtypes in terms of SM-MHC transcriptional control, we prepared nuclear extracts from intact rat tissues. As shown in FIG. 19, each CArG probe formed several DNA-protein complexes with tissue nuclear extracts. The mobility of major shift bands (complexes A and B) formed with tissue nuclear extracts was the same as that with cultured SMC nuclear extracts. The mobility of complex A seen in tissues and culture cells was identical to that formed with recombinant serum response factor (SRF). Supershift assays using anti-SRF antibody showed that both complexes A and B contained SRF (FIG. 23). Several non-SRF shift bands that were specifically competed by cold self-competitors but not by unrelated sequences (data not shown) were also formed in the EMSA experiment (complexes C–G). Each probe formed largely similar shift band patterns with the SM tissue nuclear extracts. However, the shift bands formed with liver or cultured SMC extracts were somewhat different from those formed with the SM tissues extracts. For example, CArG1, CArG2, and intronic CArG probes formed complex E with liver and cultured SMC extracts, while this complex was not formed with the SM tissue extracts. Conversely, complex F formed the intronic CArG probe and SM tissue samples was not present in the liver samples. Although a further analysis is necessary to determine the significance of these non-SRF DNA-binding proteins in transcriptional regulation in cells, the data show that non-SRF DNA-binding proteins capable of binding to the CArG probes may be differentially expressed in SM and non-SM tissues.

Figure 24:
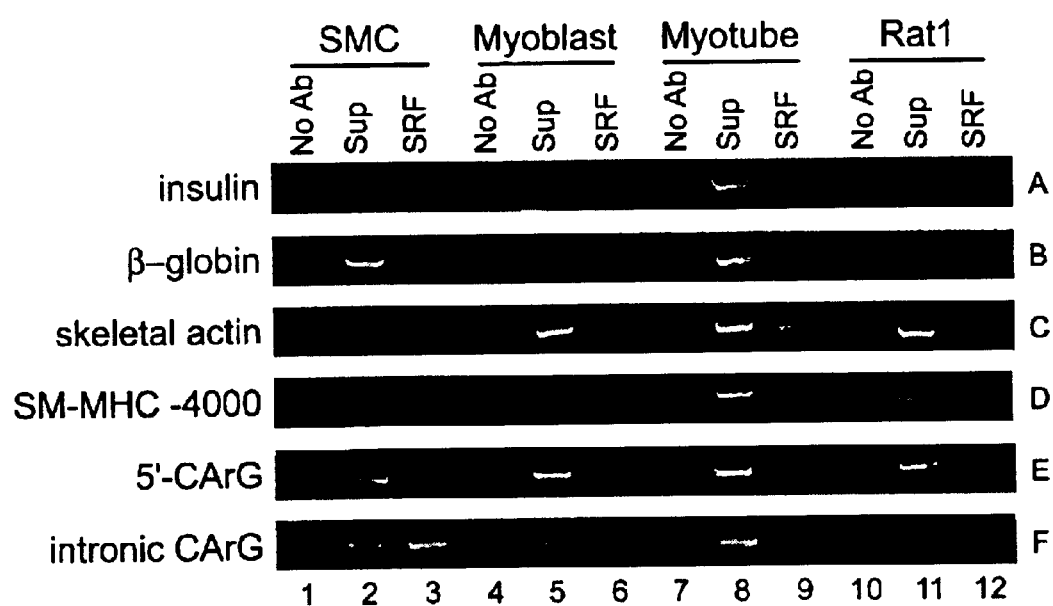
FIG. 24 shows chromatin immunoprecipitation analysis of SRF binding to the endogenous CArG regions. PCR was carried out to detect the endogenous CArG regions in immunoprecipitated chromatin fragments. Lanes 1, 4, 7, 10 show PCR amplification of control precipitation samples with no antibody. Lanes 2, 5, 8, and 11 shows amplification of 1:100 dilution samples of total input DNA for immunoprecipitation. Lanes 3, 6, 9, and 12 show amplification of target sequences in immunoprecipitated chromatin fragments with anti-SRF antibody.

2. SRF Binding of CArG Elements of the SM-MHC Gene within Intact Chromatin Under Physiological Conditions To directly address whether SRF bound the endogenous SM-MHC CArG elements, we employed chromatin immunoprecipitation (ChIP) assays. Intact cultured rat aortic SMCs, L6 rat myoblasts, L6 myotubes, and Rat1 fibroblasts were directly fixed with formaldehyde. Crosslinked chromatin was immunoprecipitated with anti-SRF antibody. The precipitated chromatin DNA was then purified and subjected to PCR analysis for enrichment of the target sequences. The promoters of insulin, β-globin, and skeletal α-actin genes (FIG. 24, Rows A–C), which are silent in SMCs, and a region (−4133 to −3832) of the SM-MHC 5'-flanking sequence (FIG. 24, Row D), which lacks CArG elements, were used in control reactions. Amplification of these sequences showed a background level of chromatin immunoprecipitation and PCR amplification (FIG. 24, Rows A–D). However, anti-SRF antibody specifically enriched the 5'-flanking CArG region (CArG1 and CArG2) and the intronic CArG regions of the SM-MHC gene (FIG. 24, Rows E and F, lanes 3) in SMC chromatin as compared with the background amplifications of the promoters of negative control genes (FIG. 24, Rows A–D, lanes 3). Importantly, the same SM-MHC regions were not enriched in immunoprecipitation samples of L6 or Rat1 cells that do not express the SM-MHC gene (FIG. 24, Rows E and F, lanes 6, 9, 12). Since the promoter region of the skeletal α-actin has been shown to contain CArG elements active in skeletal myocytes, this promoter was used as a positive control for L6 cells. As expected, the skeletal actin promoter was enriched in SRF immunoprecipitation samples from L6 myoblasts and myotubes (FIG. 24, Row C, lanes 6 and 9) but not in SMC or Rat1 cells, further demonstrating the specificity of the SRF antibody in these experiments. It is important to note that the PCR detection methods used in these ChIP experiments are not quantitative. As such, it is impossible to determine the stoichiometry of SRF binding to the SM-MHC CArG elements. Nevertheless, the ChIP experiments indicated that at least some SM-MHC CArG regions were bound by SRF in chromatin in intact cultured SMCs. In addition, observations that SRF bound the CArG regions of endogenous SM-MHC gene in chromatin in intact SMCs but not in L6 skeletal myocytes or Rat1 fibroblasts provide evidence that mechanisms exist in vivo to control SRF binding to the SM-MHC CArGs in a cells-specific manner.

3. Discussion

SRF-dependent control of SM-MHC transcription in vivo: The present studies provide evidence showing binding of SRF to the CArG elements of the endogenous SM-MHC gene in the context of intact chromatin as opposed to oligonucleotide fragments employed in typical DNA binding studies. It has been shown that in an in vitro avian proepicardial cell differentiation system two types of dominant negative SRF inhibited SMC differentiation and reduced expression of SMC marker genes including SM α-actin and SM22α. These data demonstrate the significant role of SRF in the control of endogenous SMC differentiation marker genes. A critical question is thus: How can SRF, which is not clearly SMC-specific, regulate SMC-specific gene expression? Various hypotheses have been postulated that are not mutually exclusive. First, although SRF is clearly not cell specific, there are very large differences in the level of SRF expression between different cell types that may contribute, at least in part, to cell specific SRF-CArG dependent gene expression. Second, the binding affinity of SRF may be regulated in a cell type dependent manner by interactions with other proteins, such as MHox, or by phosphorylation. Third, SRF may form SMC-specific multi-protein complexes. Although we did not observe SMC-specific higher order complexes in EMSA experiments, it is possible that a longer probe might form such a multi-protein complex in EMSAs. Lastly, chromatin remodeling may play a significant role in the regulation of activity of transcriptional regulatory modules. It is now well established that transcription factor binding to cis-elements are greatly affected by chromatin structure. It has also been shown that various transcription factors bind histone acetylases and deacetylases and thereby modify chromatin structure.

The results of ChIP assays (FIG. 24) demonstrated that the SM-MHC CArG regions were bound by SRF only in SMCs, although nuclear extracts of L6 myocytes were perfectly capable of binding the CArG elements in EMSAs (Manabe and Owens, unpublished observations). Conversely, SRF bound the skeletal α-actin promoter only in L6 myocytes but not in SMCs or fibroblasts. These data are potentially extremely important in that they suggest that the transcriptional regulatory regions of the endogenous SM-MHC gene are only active in SMC chromatin. That is, the transcriptional regulatory regions of the SM-MHC gene may be in "closed state" in the non-SM cell lines.

SMC-subtype-selective transcription control in vascular diseases: In contrast to the main function of mature SMCs (i.e., contraction), one of the major functions of SMCs in developing blood vessels is to contribute to formation of the vascular wall through cell proliferation and production of extracellular matrix components. Such functions are also extremely important during repair of vascular injury, and may contribute to post-angioplasty restenosis. As such, it is likely that a part of the transcriptional regulatory programs that are normally activated in vascular development is re-activated by vascular injury and alters gene expression. It would be thus important to study the functions of the CArG elements during vascular development and in neointimal formation induced by vascular injury.

It is well known that some vascular beds including the coronary arteries and aorta are more prone to atherogenesis. Our data provide evidence for SMC-subtype-selective transcriptional regulatory mechanisms. It is tempting to speculate that this multiplicity in the transcriptional control mechanisms might in some way be related to differential susceptibility of different vessels to atherosclerosis. The modularity of the SM-MHC transcription program might also allow us to design gene therapy vectors to target specific subsets of SMCs. SMC-selective activity obtained by the intronic CArG region coupled with a minimal TK promoter in transgenic mice suggests that the region could be used as a building block for such vectors. The results of the present studies have revealed the complex nature of transcriptional control of the SM-MHC gene in vivo in SMC-subtypes, and the role that multiple cis-regulatory modules play in processing divergent environmental cues in vivo. Further studies on the SM-MHC gene regulation should provide additional insights into the complex and dynamic regulatory mechanisms that normally control SMC differentiation and how these processes are altered during phenotypic modulation of SMCs during injury repair and development of vascular diseases.

Although the invention has been described with reference to the presently preferred embodiment, it should be understood that various modifications can be made without departing from the spirit of the invention.

What is claimed is:

1. An isolated polynucleotide comprising a smooth muscle cell myosin heavy chain (SM-MHC) promoter/enhancer, wherein the enhancer comprises nucleotides 5638–5860 of SEQ ID NO:16 or nucleotides 6862–7100 of SEQ ID NO:17, and the promoter comprises a heterologous TATA box or transcription initiation site, and wherein the promoter/enhancer initiates expression in a smooth muscle cell in vivo when introduced into an animal.

2. The polynucleotide of claim 1, wherein the promoter comprises a CArG1 and/or a CArG2 motif.

3. The polynucleotide of claim 1, wherein the enhancer is coupled to a minimal thymidine kinase (TK) promoter.

4. The polynucleotide of claim 1, wherein the promoter is operably linked to a heterologous polynucleotide.

5. The polynucleotide of claim 4, wherein the heterologous polynucleotide encodes a polypeptide.

6. An isolated polynucleotide comprising a smooth muscle cell myosin heavy chain (SM-MHC) promoter/enhancer, wherein the promoter/enhancer sequence comprises SEQ ID NO:16 or SEQ ID NO:17, wherein:

a CArG2 motif is mutated and the promoter is expressed in mesenteric artery, airway, stomach, intestine and bladder but not aorta, coronary artery or vena cava when introduced into an animal; or the intronic CArG motif at positions 5815–5825 of SEQ ID NO:16 or 7046–7056 of SEQ ID NO:17 is mutated and the promoter is expressed in coronary artery, mesenteric artery, vena cava, airway, stomach, intestine and bladder but not aorta when introduced into an animal.

7. The polynucleotide of claim 6, wherein the promoter/enhancer comprises SEQ ID NO:16 and the CArG2 motif is mutated.

8. The polynucleotide of claim 6, wherein the promoter/enhancer comprises SEQ ID NO:16 and the intronic CArG motif is mutated.

9. The polynucleotide of claim 6, wherein the promoter is operably linked to a heterologous polynucleotide.

10. The polynucleotide of claim 9, wherein the heterologous polynucleotide encodes a polypeptide.

11. An isolated genetically engineered cell comprising the polynucleotide of claim 1 or 6.

12. A composition comprising the polynucleotide of claim 1 or 6 in a pharmaceutically acceptable carrier.

13. An isolated polynucleotide comprising a smooth muscle cell myosin heavy chain (SM-MHC) promoter/enhancer, wherein the promoter/enhancer sequence comprises:

nucleotides 1 to 9500 and 11,700 to 13,700 of SEQ ID NO:16 and does not comprise the intervening nucleotides 9501–11699 of SEQ ID NO: 16; or nucleotides 1 to 6700 and 9,500 to 15,800 of SEQ ID NO:16 and does not comprise the intervening nucleotides 6701–9499 of SEQ ID NO:16; and wherein the promoter/enhancer comprises a mutated or unmutated CArG2 or intronic CArG motif and the promoter/enhancer initiates expression in pulmonary vascular and airway smooth muscle cells in vivo when introduced into an animal.

14. The isolated polynucleotide of claim 13, wherein the promoter/enhancer comprises nucleotides 1 to 9500 and 11,700 to 13,700 of SEQ ID NO:16 and does not comprise the intervening nucleotides 9501–11699 of SEQ ID NO:16.

15. The isolated polynucleotide of claim 13, wherein the promoter/enhancer comprises nucleotides 1 to 6700 and 9,500 to 15,800 of SEQ ID NO:16 and does not comprise the intervening nucleotides 6701–9499 of SEQ ID NO:16.

16. The isolated polynucleotide of claim 13, wherein the promoter/enhancer initiates expression in gastrointestinal, airway, arteriolar, and bladder smooth muscle cells but does not initiate expression in vascular smooth muscle cells within large arteries.

17. The isolated polynucleotide of claim 13, wherein the promoter/enhancer comprises a mutated CArG2 motif.

18. The isolated polynucleotide of claim 13, wherein the promoter/enhancer comprises an unmutated CArG2 motif.

19. The isolated polynucleotide of claim 13, wherein the promoter/enhancer comprises a mutated intronic CArG motif.

20. The isolated polynucleotide of claim 13, wherein the promoter/enhancer comprises an unmutated intronic CArG motif.

21. The isolated polynucleotide of claim 19, wherein the promoter/enhancer initiates selective expression in vascular smooth muscle in arterioles and airway smooth muscle.

22. The isolated polynucleotide of claim 17, wherein the promoter/enhancer initiates selective expression in gastrointestinal smooth muscle.

23. An isolated genetically engineered cell comprising the polynucleotide of claim 13.

24. A composition comprising the polynucleotide of claim 13 in a pharmaceutically acceptable carrier.

25. The polynucleotide of claim 1, wherein the enhancer comprises nucleotides 5638–5860 of SEQ ID NO:16.

26. The polynucleotide of claim 1, wherein the enhancer comprises nucleotides 6862–7100 of SEQ ID NO:17.

27. The polynucleotide of claim 6, wherein the promoter/enhancer comprises SEQ ID NO:17 and the CArG2 motif is mutated.

28. The polynucleotide of claim 6, wherein the promoter/enhancer comprises SEQ ID NO:17 and the intronic CArG motif is mutated.

* * * * *

SEQUENCE LISTING

<160> NUMBER OF SEQ ID NOS: 23

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: CArG1
      sequence to be mutated

<400> SEQUENCE: 1
ttccttttat gg                                                          12

<210> SEQ ID NO 2
<211> LENGTH: 11
<212> TYPE: DNA
<213> ORGANISM: Artificial Sequence

```
<220> FEATURE:
<223> OTHER INFORMATION: Description of Artificial Sequence: CArG1
      mutated sequence

<400> SEQUENCE: 2
ggatcctatg g                                                          11

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: CArG2
      sequence to be mutated

<400> SEQUENCE: 3
ccttttggg                                                             10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: CArG2
      mutated sequence

<400> SEQUENCE: 4
atcctttggg                                                            10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Intronic
      CArG sequence to be mutated

<400> SEQUENCE: 5
ccttgtatgg                                                            10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Intronic
      CarG mutated sequence

<400> SEQUENCE: 6
aggcctatgg                                                            10

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: CArG1 sense
      strand EMSA probe

<400> SEQUENCE: 7
gacttccttt tatggcctga                                                 20

<210> SEQ ID NO 8
<211> LENGTH: 20
<212> TYPE: DNA
<213> ORGANISM: Artificial Sequence
<220> FEATURE:
```

<223> OTHER INFORMATION: Description of Artificial Sequence: CArG2 sense
      strand EMSA probe

<400> SEQUENCE: 8
cctggccttt ttgggttgtt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Intronic
      CArG sense strand EMSA probe

<400> SEQUENCE: 9
catgcccttg tatggtagtg                                              20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Insulin PCR
      primer 1

<400> SEQUENCE: 10
gccaaaactc tagggactttt aggaaggatg                                  30

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Insulin PCR
      primer 2

<400> SEQUENCE: 11
gccgggcaac ctccagtgcc aaggtctgaa gatc                              34

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Beta-globin
      PCR primer 1

<400> SEQUENCE: 12
cagcgttttc ttcagaggga gtacccagag                                   30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Beta-globin
      PCR primer 2

<400> SEQUENCE: 13
tcagaagcaa atgtgaggag cgactgatcc                                   30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Skeletal -continued alpha-actin PCR primer 1

<400> SEQUENCE: 14
caggctgaga agcagccgaa gggactctag    30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Skeletal
      alpha-actin PCR primer 2

<400> SEQUENCE: 15
acctccaccc tacctgctgc tctgactctg    30

<210> SEQ ID NO 16
<211> LENGTH: 16011
<212> TYPE: DNA
<213> ORGANISM: Rattus sp.

<400> SEQUENCE: 16
agatcttaaa acacatcaac ctgggctgag gggatgtgtg tctctgtgtc tgtgtatgca    60
catgcatttg aggccagatg aaaatgtcag atgtcctctc actgctttat tcccttgaga   120
cagggtccct cactgaactt gttggagcta tgctggtagc cagcaagccc cagtggcctt   180
cctgtctcta tctcacacag cacaatatgt gtggccatgc tccactttt tacatggaaa    240 ttggggtctt ccaactgggg ttctcatttg tgcagtgaca ctcttcccca ctgagccatc   300
tcctcaggcc agctgatata tttttaaata attaaatatt tagcacatgc ctttagaagc   360
caatagctat ttaaagctgt ttgcttaaaa aaaaaaaaa aaaaaagact tcattatccc    420
aacacttatg agggagagac aataattcca aaccagaac cagccagggt acacagtgag    480
actttattta aaaaaaaaaa aaaagaaag aagaaaaaa aaaagaaaaa gaaaaaaaaa     540
ggctccaaag agaaatttcc ccttcatcat ctaatcacaa gaaacaatt tatttatttt    600 gacatcactc agtccaaagg agctttttgt aaagtgactt ctcttcttaa aataagtgac   660
ccttcccaac caccaaaaac aaaacagaaa cctctgccct gttctagagt ccttttgaag   720
acttcagata cctgaagagt ggacagatat ttaccgagtg acttaaatga acatactgtc   780
cctgggtact gctcaagcat gccaggagag catggatggt ttatgcaagg ctggcactgt   840
cattaacaac tcagtaaggc ggagaagaca gagagcctct cctaagacaa tggcacataa   900
ggacatgggt aaccccagag gttcccggct agtacttagc agagctgaga tcagacttgg   960
gcctctgtgc tcgcttgcct agtgggcaac actcaagact ggggtaaaca ataagttgat  1020
ctgggatatg gctcagtaat cacactgaga attcaacact gggaaggcag aggaggatcc  1080 ctggattgc tgcctggctc tctagcagcc tagcagaatc aacaaactcc aggttcagtg    1140
agagatgctc acaaaataaa atggaggagc aactgaacac actcagtgtt gacccacaca  1200
cacactaaag aacacgtgta ccacacagac acagacacag gataacctac ccatgttgtg  1260
tatggactca gccagcccag gttggaaact cagttcctct gttaactctt ttcaaacctg  1320
ggtcctcagc gatgtgctgg ggaacctact tcacggcatt attctgggca ttagatgtaa  1380
aggaagcagt aaagttccc tttcttgac tgaggtgatg cgagaatgag ggcctgaatt     1440
ccatctctag gactcacata agacaccca gactgcactg gccagtaagc ctcacctatg    1500
cctccaagcc tggctgtgag agactgtctc aaaaacaaag taaaaacaac aaaatcaatg  1560

```
tcagatgtgc acacatcgaa tcccagcatg tgtacggcat gcttgcagtc agccttgttt    1620
acagagagtt ctaggccaac cagctataca cagtgagacc ctgtggtaga cggctcctaa    1680
gaactgacat ttgtgactga cagatgtgca catctaccac atgcacatca cagtttccat    1740
tttacaaaaa ggttaacact tactaattga ttagggagtg gggcacccca ctgctacatg    1800
tgaaagccag agaatgatgt gttccagtcg gtcagttgtg tccttccacc atgtaggtcc    1860
taaaaatgga actcaaggca gtcttggcag caagtgcttt atccatagtg ccatcttatt    1920
ggcccagtct ccttataatg aaattatttg tgtttccaag ttgatgtaat tctttaaaaa    1980
tcagctgtgc tccttggagt ttgacttcac tgaagcctgc tacaggagtg cccttccttc    2040
ctagcactag gatggccagc tctgggctgg tttcagacta gggtaggtgc aggtgggccc    2100
tgggcttccc tccttcattc ctcctgggct caatgccaag ccggtttcca ttccttttac    2160
gtgcactgcg aagaggcttt ggggaagcgg cctcatccat catgcagaga gctcctcccc    2220
cacctctaca gagagccagc caagctgctg tccttggctc tgctctgtcc accctgtgag    2280
gaggctggga tgaggttggg gatggggagg atcaggattc agatgttttc aagtctgaga    2340
agcaggtgag cttggtccta gaagaatatg gaagggtct actggggttg agatatagat    2400
cactgtatca aagtcaacag gggggctgtg tggcttttc atatcccaaa gtcagcttgg    2460
tgctggtttc ctaggcttcc tgagtccgac aaaggtgcag tgtgttaatc tcacaccact    2520
tcaaggactg ttacaaaaaa aaaataggaa ggagctcgat tcgcccctttt ttacaggcag    2580 ggtaactaag agccagtact tgcccatggt cctgctgtta taagaggct cagtagactc    2640 ccattcaaac aactgtgctc agaggccttc tgtcgtcctg tggccaattc ccctattgct    2700
ctctggagta atattggga tattaaacag tactgacctt gctgaggacc ctcagggtac    2760
tcagctcttc tggcctgcaa atgggggctg ggacaggttg gccaggatca tcctctggtt    2820
gggagaacca gctgcacgtg ggtctggagc tcttattagt actggggtcc ccataacgct    2880
ccatgggctc agcggggagc tgcacgggac catatttagt caggggagc cagagccccg    2940 ctggtatgcc aagctgggaa ttcttgtttc gagaattgcg cctggccttt ttgggttgtt    3000
tcccgcccag gcccaggagg gaggaccagc tcaggacctc gagggtccgt gcgcggggag    3060
cgaggcgtcc ccggcctggc atgaggccaa ctctgcctcg acttcctttt atggcctgag    3120
tgtgagtgca tggagagtgg gagggaggga gggagagagg gaggaaagaa agcggggtgg    3180
gggggtgggg gggtggggggg gtggggggggt gcggagagca gagacagaga cagagagaca    3240
gagagacaca cagagagaga cagagagaca gagagacaca cagagagaga cagagacaga    3300
cacacacaga gagagacaga cagacaaaga gagagacaga gacagagaga cacacacaga    3360
gagacagaca gacaaaaaga gaagagagac agagacttta gggacgtaat catcacaggg    3420
aaatcaaagc taagagtgtg atgaaaagag tgtcaggtca gacaaaagag acaggggcca    3480
agatccgtac agggctaagg gacacagaga ttgagaacac cgagtggtaa ggggggcagc    3540
tgacagcagg tcccccacat tctcttagag tcttagcatg catcctccaa gtgccataac    3600
gcagtagcaa cccgctttttc aacgatgctc agagaaacca tgttattggt cccaggcacc    3660
ccggttgtag ggtgaaagga gctgcagaga acaagttgga aaaacaagtt tcccagcagt    3720
cacagaggat atgcagtgac tgtgccgact tgttttttttt tttttaagtc cccttccccc    3780 ccccgcccc gccccggct tgctaagcac aaccggcttc gaatcttagg aagtggcagg    3840
cgaatgaaga ggggatgagg gagagagggt ggcatcaagt ctccagtatg tatgaacaga    3900
aagaggttaa aatccagctg gaatggacct aggggaagaa attctcaagt ctccctacag    3960
```

```
actctgaaca ccgaatccct tttctctaag gacgcaggat ctgggtggct gcagggagcg    4020
aggcctgagg ctgtgggtca acttgccagc agccccctg cgcctgcgct aggtggttcc     4080
cagaggctct gttcctcacc tgcagggggc gctgggaagg gcagaggacc ctcccacccc    4140
gcccggcagt cacctcccct tccccaccct cgggtagcgc tgactctata agccagatg     4200
tccgaagcat acagagagat ttggaccatc ccagcctggg atcagtgtca gatccgagct    4260
ctccatccgg tgttctcctg ctagtccacc ccagtagcag atctgtaagt agaagttgat    4320
cccttagggg caagcctggg cggtgagctt gagcagcttc taaaacatcc tccagggagt    4380
ggggacccca aggggttctg attgtcatct cttataagga cagtgggaag aagcccggta    4440
caggaccacc ctagacctcc cgtgattact cccattctcc gcaccaaacc agcatcctca    4500
ggttgcctat gaacagaacc acctgggaaa gtggggtagg taattaaagg ttctggccac    4560
tgggcccaat tccaggtatt ttaagactac agtctaaaaa gcaaacaaaa tggcctactt    4620
aaaaactaac tagtgacaca gtggacaagt gaactgtggt ggaaactgtg ggtctgaatt    4680
caaataccag tattgaaaat aataagaagt ctgggataaa tatccactga acatccccag    4740
aatactcaaa acatgggtta aagtttaatg actctgaaca caggccgtgt gttcttattc    4800
cactcctaat ggaatgtgct gttgaaaatt tactggtaaa caaaaatgct taatgttaaa    4860
taaggtcgtt tcttcctctg ttacttccaa aacacaaatc tccattaaaa aggaaccttc    4920
tccagtttgg ttgggccccc agatgccag gtgggtgctg aggctccatt tgcatcccc     4980
acactgagtg agcagacgat ggattttggg gctcctcagt gggaaggtta ctctcaggtc    5040
agggagagga gctagcagag aaatttatgc tattccagtt cagaattgga gaagtcttgc    5100
catgtccaga aagcacccct caaagttatg tctgtcagag aacagaaaaa ttttttttga    5160
aagccaggac aaggctgctt tggttctact actaagaact gaaaactgc tgacttgctg     5220
ggaaagaagg aaatccggtt gtgtttggta aactactctg cttcgttggt ttcctggggg    5280
aggtttttt ttagttcagt aattcaatat gctattttag actcaaagaa agacaggtct     5340
gaaagtctct cataacaaga aacactttct cttttatgat gttgttgatg gcacacttaa    5400
caagccaggt gctttaacag cgtttagatg gaactgggtt cttttaatca tcatatacac    5460
cttaccttgt cttgacatct ctgttttttcc caaaaccaaa atttgttgga ctcctgtttc    5520
tgatggattc agtgtttcca gcttccatca cttttttgaag aagattgaaa ctgatctttt    5580
accaatttaa aatgacagag actgtctttt aaattttgtt gatgttgttg tttccctgtg    5640
gatgtggtag ggttccagga ggctggcgtg atctcaaaca tgcctgggcc aagccaccct    5700
ggagaaacct ggacttttat tatcagatct gaaatagagc ctcttccgta caaggtagtc    5760
actatggatt tatcattact tttctgtggg aggctgggct ggaggcagac atgcccttgt    5820
atggtagtgt tttctatgag gccattccca gtccccttg gccaatcacc cagcctttcg     5880
atgcagcctg actggcttga gttctgggta cttctctgtc tttccctgta gagatggaca    5940
atgaagttct ttttttcctc tcttttcttg tttggaagtt ctatttgtat ttttttggtg    6000
gaaattatat tccacatatc taataagaac gggtggtgtt tacatctaat aaaccattga    6060
ataattttga aacaggataa agacgatcct tttagaaaac tatatcccgt ttcaaatact    6120
cagaatcagg tcttaaccac attattttgc caggtatggt ggcttgtgtc taaaatacta    6180
gcacttggga ggctaaagca agagagtttg aggctaacct ggactgcata gcaagttcag    6240
gccatcctgg actacagtgg gaaacactat cttggaaaaa ataaaaaata aaaatcaaaa    6300
```

```
cccagcctaa tggtacataa cttcaattcc agcatctgag gtaaaccagg aagcacagct   6360
gattaatgaa cccaaagtca gcctgggcta cctaaggaat cctatctttt acaatttgtt   6420
gatgctgttg tcattttcct gatcactttc ccatctgcag aatgggactg ttgagaacag   6480
ccagcgtgtt aatgtttctg tagcacttgc ttagtcttct gagaagtaga agatcactta   6540
gctagggttt gatccccatg actgcagcaa aagaggaaga ctcattaatt ggagtcttca   6600
cagtagccct tggaaccaat actaatagtc ttcactccat tcataaatg tgggctttga    6660
aaactttgtt ctgtctataa aagatggggg ctcttacaaa ctaagcttct tgtaactcca   6720
gagcctaatg cccttttggg agctttcaat agataaccca tgtgaagggt ctgacacaag   6780
gctggcacca gcaaagttca gcagatggta atttatagta atatgactag ggacgcttaa   6840
gagcatattc tgtatgacac agctgatatc aagaaaccca acggtggcc tttcccctaa    6900
agcagaaact cacccctaat tttccttag tgtaaatctc atagtggatt ctttgctccc    6960
tggttctctt tctgtcacta gtgaccttt agttacattg atctataggc ttcaaggacc    7020
aggaggcaca gagtcaagag aaaggcaagc aagaatttga agggagaagg aaaccgctca   7080
gcactgtagc aaggggaggt caggctacca tgatgctcct gcgcttcagg gaattatcct   7140
ctcagaatgg ccaacagggt agggacctgg cctgttccac tcaggcccat tgaactttc    7200
tttctgttct atgggtccct acagatgaat tcagcccact gtagactgga agttcatctt   7260
taacagcatc caaacggaac acatacagac cttctttctt gtcactgtcc ctgagtcaag   7320
cagcataaga actatgtctg ccaacctgcg aggggaagtt gctcaagatg ctatgcaaac   7380
actccagctt tccatggaag ggacttcagc atctatggat ggtggtagca aagcactcct   7440
caagctgatc aaagaatagc tgtcccttcc tgcccctccc ctaatgaagc gtgcagtcag   7500
tgacagagac ctcagaaatg tcttaggtca ccaaaggtca ttcttgccat cccaggctcc   7560
agattagcat tttctccctt tttatttccc tccattttgc ctgtctgcat atgcactact   7620
aacaaacatt ctttctttct tttttttttt tttcttggag ctggggactg aacccagggc   7680
cttgcgcttg ctaggcaagc gctctaccac tgagctaaat ccccagcccc gctaacaaac   7740
attcttaaat agaattctaa atttttaaa gtcaaatttc cctttactc aaaccctggc    7800
attttacaaa cattttca ccttatcaca aatcttcact atcttttcta tatctttata    7860
tcattgtatg ttacttttta tctgctacgt agtattctgt tacgtattta ataaaatata   7920
cttggtgcat gatgccatgt ataaatggcg cttggggaag tacccgtgta ctagttgact   7980
gttgcccatc agaaatgccc aggaccagaa atgttccaga gttttctttt cttttaaatt   8040
cttttgatt ttgggatatt tgcacataaa taattatata tttgtatata aataatgata   8100
tatcctggaa acgagcacta attcttttgt tgcctgtctt ctgggttttt ttttttcttt   8160
tccttctttc ttttgttct tggccatcct ggagctctct gtagaccagg ttgtgcttga   8220
actatagaga tcctcctgcc tctgcctccc acatgctaag actaaaggca agagccatca   8280
cacccatctg tgagcacaaa tcttgatatt tcacctttgc tttatacaga tggttgtata   8340
gtcagtcgtt gtattcgatg ttttttaattc tacattttca ctgtgacctg ctacatgaaa   8400
ttcaaataca aacttgtcca ctcacacaat attggccctc aaaaagctgt gagcctttga   8460
actttttgggg ttaagaatgt ttagcttgta tccgtattct tcgcttgtaa actctcttcc   8520
tgtaatcaca tgagttccta gcaaagaggt gaatagatag cacattggga atcagcatct   8580
gtctctaaat ggtctttgaa agaaactgta gatacctgcc tggaccagcc agacctgtgt   8640
cttagcacct atttttaaaca ttgttctacc tgagttgtaa gatgcaaaac atagtggggc   8700
```

```
tctgagggcc caaaggccct gaacagggt gacctcagtt gtgtggaata gggagaaaga    8760
cagcagaagg aagggaggaa agacgggcaa ggaggggaag gtgttcatgt gtatggctgc    8820
atctaaatag aagccatgaa gactagctat tgtttctcag gtccttccaa cttgcttttg    8880
gagacaggaa ccctcaccag cctggaactt gccaagtagc taattggctg gctcttgacc    8940
cctagatctc tttcccctcc actctaacgt tacaacatac agctctctct ctctctctct    9000
ctctctctct ctctctctct ctctctctct ctcattttat tttttaaaaa aaatttattt    9060
atttatttat ttatttattt atttatttat ttatttattt catggatgta atacctgtcc    9120
tgtctcaacc ccaaaatggg catcggatcc cattccagat ggttgtgagc caccatgtgg    9180
ttgctgggaa ttgaactcag gacctctggg agagcagtca gtactcttaa tgctgagcca    9240
tctctctagc ccttttccccc tcttctaaaa catagttttt gaagatctaa cgcagatctt    9300
caagtgtcag tatggcaagc actttgctga ctcaccagcc catgaccttc tcccttaatc    9360
tccaaatcct tttagtggga gagacacaat cgttttactt tagccattgg aaagagcttc    9420
cttctaaagc agcttgaaaa gccattgggg tttccagcgt gtgtgtggca gtgttaccag    9480
gttattgtga tgggacaagt tcttattctc tttcttctga ggaggtaccc tggagacctt    9540
ggggaagtgg gggtggtagg gaggtttatg gcattgggc agggagtgaa gaagagattt    9600
actgctgaga gcaaaaggat tgttagatcc aacaatctaa caaaaaaggt caaacttttt    9660
tttcttttat gaccttagtt gtgataacag aaaaatagta atgtaagtga tgtccacttc    9720
acagaatcct cataagatat tcaagaccat aaatgtgggc cactcttact ttgatgccca    9780
gtaggggggcc cctgagcaga tgcagcttag ttaataggat gcttgcccac catgttttgt    9840
acatgttcca ccctcagtac acagccaggc atcgtaggaa acacttgtag cccctagcac    9900
ttggcgggag gaccaagagt tcaagtccgt ttttgattat gtagtgagtt cagggttagc    9960
atgggctata ggagactgta gagggctatg tgattaagaa cagatttgag ccccacaggg   10020
ctcctggtgc agcatgagtt tgaggaacta gtgtgtatag catgcttttc cttcttcttg   10080
gtatgtcaag tgactttcta gacgcagatg tggcatcgaa ctagaactaa cattattggg   10140
gcctctttgg attgcttact gagctgcagc tttggctcca agaacttatt atggagatgg   10200
gcatggtggt aacaactaca ctacagaaga ctactacttt gagaccagcc tgtaccagag   10260
cctggtggat acagctcaat gggagaacac atattgagca tgtacaagtc ctgagttcga   10320
tcttcagtac ctcgaatatt ggccaactaa aaggaatgaa tttaggggtg ggaataaagt   10380
tcagatagta gagtgtctgg ctagcattca caaagcccca agtttgacct ccagcactcc   10440
agaacctgga tgtggtagag tacatctatg atcccagcac tcaggagaac ttcaaagtta   10500
ttccaagcta cataataata caagaccagc ctgggctaca caagatctta tctcaaaaag   10560
ctttggtttc aaactgggga cagttttccc tctgggagtg atatctagca gtgtctggac   10620
ctccttttga tgtcatgact aggaaatggt ggatactggc atagagtggg ctgaactcac   10680
actgaacagc accagagaac cagccagtgc caaggccaat agtacagggg ctgagaaaat   10740
ccactgtaaa tcaggagtca gaacaggacc aggagttaga aaaccaaatg ttacttcagc   10800
ctgtcttgtg ggtctttaat ggcattgtga ttttggttct agtcatcatt tcttttcggt   10860
attgagattt gaactagggt cttgtgcatg ctaagtaaga actctgccac tgtgccatat   10920
cccaacctat gtggttgttt tgtatcaggg tctctccttg taaccaata ctcaaaccca   10980
tcatctcctt catcatggga ctacatatgt gagcagtttt actgtttttc cttcttcctt   11040
```

```
gtgttttacg caatacctgt cctgatatttt cttgctgtat tgtcactgtc ccatcttttg   11100
aaaatttcag gctctgaaca gaaatgaagc aaatcttctg acagtaaatg gagttccctg   11160
aacttccaaa ctgccagaca gaagcagaat gtgtcctctg tatgcctgta attttttctg   11220
tccttgagtt ctctgcctgc ctcctctaaa ttctaaaaaa agaaagagca aaacaaaca   11280 gacaataaaa aaacttgcaa ctttttttcag aagccacaag actgtaaaag gaccaacaaa   11340
ctgctttgcc tctgtgtgcc ttggtttctc attggtaaag gaatggtaac atctttcctg   11400
ggttgttttg caatgctggg gatagaatcc agggcttaga gtatattagg ttccctgcct   11460
ctaaactata ttctctagtc ttaaaagtat tgtttgcatt gttactgtgt tttatggtgg   11520
ggggatggga acccagggac tgtagcttac taagtgttct gcctgtgggc tatacccctag   11580 ccacctccta ggactttgct gtttatttat ttatttagtt tagggctttg ttattgattt   11640
attagttagt taatttaggg gattaaatga gagagtaatt attacctcat atggtttagc   11700
aactattaca agcatgctag tatcattaat ttgtgggact ctgaattctt tccaaggcaa   11760
gtgtgtgtcc agtattgttc tgggaacccc tccttccctg caggttcata ggagcagagt   11820
ggttttctgg ttgtaaaatc tgccaagaac tggaatgtcc tgtctaggct ctgcatctta   11880
gtgatgggca aaaagatgt agtgtgtgtg acattcatgt ggtggtgcat gcatgtgtgt   11940
acatgagtgt acatgcttga gccctgaaac aggatttctc actcaattgc catcaagctt   12000
tgatgtccct aatccttctc caatactagg ttgtaatagt atacatggca aggctagctt   12060
tttatgtcag ctactgggat tcaaactcag gtctggacag ctgttattgt cagctgagcc   12120
ttatctgctg tctttgtcat tatcagctgg gtttaaaaag tatccttgat cctattctca   12180
ccgttcccca aacccaaaca ttcctgggca ccagggttcc aaagcattca gtgtggaacc   12240
aaagtttcag cttccttggc tttgaccaaa gcagtcttgt gcttcacaac tgtcataact   12300
gttgtcaagg gcaacaaagc ctcagggagc agccagatga cctcactccg ttttttggcca   12360 gagacacaaa ctttgcactt gatcttgttt gtgcttttaa gccccgtttt agatgaggtt   12420
cctggaaaag ctaatctcca cgtcttttca ttttctgtt gaacctttcg tgatgctttc   12480
taacttaatt gcaatttaaa agaggcagc ttgctgtcca ggaggaatga cacaaacact   12540
aggcctctga gtgactaaag accatttgaa atgggtcgtc atctattaca gaaaatgtaa   12600
aatatacttt acacttctta actatgtgcc taaagtatgt tttatttttgt tttcctctaa   12660 aaaaagaatt atttatttta cgtatttgag tacactgtag ctgacttcag atccaccaga   12720
agagggcctt agattccatt acagatggtt gtgagctacc gtgtgatggg aattgaactc   12780
aggacctctg gaaagcagt cagtgctctt aaccactgag ccatctttcc ggcctttatt   12840 ttccttttt taaaaaaaa ataaatgaaa aattaacttt tatttcatgg gtgtatatat   12900
gtatgggctc aaacatgata tatgtgcatg ggctcacaca tgcagtggtg catgtataaa   12960
agtcagagac aacttgcaga agatggtttg ctcttttcat catatgggcc ctgaggatta   13020
aactcaagtc atcagttttt gtgccaaccc cctttactcc ccgagccttc tctcaacagc   13080
tcctcacttt acctttttat ttaaaaaaca aacaaacaaa caaacaccaa cccagcctcc   13140
cacacaacaa cgaaaagatc tcatgtagcc ccagggtggc tttgaactcc ccatatagct   13200
taggatgact ttgaattcct aatgttcttg cctctacctc ctagttacta tgcctggctt   13260
cttaccatag aatttaagaa attatctaag gtaaagtggt gttatgtgct tataagccag   13320
gcactcagga agaagctaag gcatgatgat tgtgagtttg aagccaaccc aggttacaga   13380
ggatctcatc aagaaatcaa cattcaattt tcaattattt cttaaattttt ttgaggttgg   13440
```

```
gctggagggg ttggttaaga gcactggttg gtcttccaga ggacatgagt ttgattccct    13500
gtaccccaca tggtggctca caaccatctg taattttaat tctagggatc taacgccctc    13560
ttcaagcctt ctcaggcagg tgcataagta cacagtcata catgcacaga aaacacataa    13620
acataaaata aataaattaa aattttgaaa gttttttttg ggtggaaggt acttttaagt    13680
aacattctat gttatggaac aagtgcattc aattttacta agttttaat tttagcttt     13740 tgtttgtttg ttttctgttt ggaacaaggt cttgtgtatc ccaagcatcc tcaaagttgt    13800
tgtgtagcga aggatgacct tgaatttttt tatactactg ccttcttgag ggcaagcatt    13860
ttaatatagg caaataaac tttaaactt gtttgctgtg caggtatata tggtgtgcaa    13920
gtgtatctgt gtgtgtgtgt gtgtgtgtgt gtgtgtgtgt gtgtgtgaga gagagagaga    13980
gagagagaga gagagagaga gagagagaga gattagagaa taacttgtgg aagttctctc    14040
cttctaccct gtgggtccca gggtaaactc gggttataag gctttgcacc cttttcccca    14100
ctgagaactt cttgctggcc tcactcccta ttttatttta ttggtggcag tactattgct    14160
tttgaatccc atctgaagct tgttttgtt gtttggtttt taaggcagtc ttaactgtga    14220
cctaagctgg tttaaaactc acaggaatta tccacctcca cctcccaagt gttggggtta    14280
cagatgtgag ccccaagcct gagtgcttct gaaagctgct ttttttatt tcaaaactat    14340 cttttctctg tgtgtaggtc tgattagttg tggggttagg tggtgtcagc atgatccatc    14400
actctccagc tattattctt aaaatgaagg gtctgggggc tgggattta gctcagtggt    14460 agagcgctta cctaggaagc gcaaggccct gggttcggtc cccagctccg aaaaaaagaa    14520
ccaaaaaaaa aaaaaatgaa gggtctggtg gctgaggaaa aagctcagtt gcaaaaaaac    14580
atgaaaacct gattcaatct gtaaagccca cataaaagcc aggcatggcg gcatgcacct    14640 ataacccag cactggggaa acagaacagg agaataccaa gaacttgctg gtcagtcagt    14700
ctagtttaat tggtgagctc caagctcagt gagaccctgt ctcaaaaata aatgagatg    14760 atctgtcatc aagacctggc ctccatacat atatgcacac atgttactcc ctcacatgaa    14820
acatatttat aaacaaacat atgcacacac ttgtgcatac atgaacagat atctatattg    14880
gcatacacat taaaacacac acacacatat atatatacaa aagtgtgtac aaacataggc    14940
atagtataca accatgcata aatgcacagt cacacatatg aatgcattca tattcacaca    15000
tggacacatg aacacataca tatatgctat atcttatatt acactccatt actatccccc    15060
agtccaggtt tcaaatattt acaaacagaa aagcgggcta ctacctgtac ttttcccaa    15120 ttgcctttga acagcgatct ctcgacacct gatccccgca gtgctccctg cggcagagct    15180
tcatccggaa acaaccccca tgcactctat tgattttaat actggggatt acctggagcc    15240
ttgtaaagct aaacacattg tctactgcta aatacttcat tctttgcccc tttcccatgg    15300
ggcgttttca atccagttat ttttagtgtg ttcttagatt taagcatcca ctagtacaga    15360
ttcaaggata ttttttattat ccccaaata acagtatttg ttaggtgtaa ccttgtagtt    15420 tttcccagc ggctaatta aattgctttc atgaatagcc tattctggaa aagtaatttt    15480
tttttttttt tttttttttg ggttcttttt ttcggagctg gggaccgaac ccagggcctt    15540
gcgcttccta ggtaagcgct ctaccactga gctaaatccc cagccccaat tctgacatt    15600 tcttataaat gtcactatgc tgtatgtgtt ctttcagcat tgcaacactt tggttccttt    15660
ttatggctca atactggtct acttatggat ctaccacact atctatccat tcatctcaac    15720
atagtcatgg gtggtatttc tactttgggg ctattataag cttgctagga gtattatga    15780
```

```
ccacatctttt agatgcactg atgcattcat ttatcctaag aacagatcct ggatcatatg    15840
gtggttctgt gttcaaacat cagaggcacc accatttatt ttataatagg catttaagat    15900
ttgggtatct tctaactggg tggtggtggt acatgcctgt agtcccagct cctgggaggc    15960
agaggcaagt agatccgaat tctcgcccta tagtgagtcg tattagtcga c             16011

<210> SEQ ID NO 17
<211> LENGTH: 18605
<212> TYPE: DNA
<213> ORGANISM: Homo sapiens

<400> SEQUENCE: 17
tttaaaatta ttaaatcttc ttttttttttt ttttgagatg gagcctctct ctctagccta      60
ggctagagtg caatggtgtg atcttggctc actgcaacct ccacctccca ggttcaaggg     120
attctcctgt ctcagcctcc caagtagctg ggactacagg cgtgcacaac cacacccgac     180
tagttttgtt attttagta gtgatagggt tttaccatgt tggccaggct ggtctcgaac     240
tcctgacctc aagtgttccc tccaccttgg cctcccaaag tgctgggatt acaggtgtga     300
gccactgtgc ccggccaaaa aatattaaat cttgaggcac atgcaggagt aagccatgct     360
cagacccaat cttcgatgtt actaaaaatt ggaggggatc acacttcatg gttttgtttt     420
gttttgtttt tttgagacag ggtcttgctc tgttgcccag gctggagtgc actggtacga     480
tcacagttca ctgcagcctc aaactctggg gctcaaacaa tcctcctact tcactctcta     540
gttgggacta caggcacaca ctgctgtgct cgactaatta ttattattat tattattat     600 attattatta ttattattat tattttgtag agacagggat cttgctatgt tacctaggct     660
gttcttgaac tcctgggctc aagcgatcct tccgctgcag cctctcaaag tgctaggatt     720
acaggcatgc ccagccactt tggggctttt ttaagccaac agcaaaaaaa gactataaga     780
gagaaatttc cccttggctg tcttgtttca tggattcgtg gaaactccca ttaaacagcc     840
ggtcacagaa aaagatatgc caaggaaaat tacttgacag cactcagtca aagtgacatt     900
ttaaaaagag actattgcct cctccatctt aaaagaactg accttttgag ccatgagaaa     960
tgaaacagag gcatctgatc gaatgataac aatgcacttc tgaagattca aacatcggaa    1020
cttcatgcat tggacacata tctattgaat gactcttaag tgaacatact gtccctgcct    1080
gcttccagag ggtactagag aggtcggaga tggttcataa aggccttcac atgtgctgtc    1140
atatttaaca atcagaaagg tacttgaggc aaagaatctg atcatctttg tttttccttg    1200
agaaaatgcg ctcagagagg tttactgaca atcccaaagg tgcttggttg gtgcttaaga    1260
gatctgggtt taaaacctca gactgctgtc tactatggcc tgtgtcagaa agactggggt    1320
tggaattcct gttccaccac tgctgtgtta tttaacccct ccaaacctag attctcaaca    1380
ataaaatggg ggtagggagg gaattaaagt atgtaccttta tttttagag acaacatctt    1440 gctctgtcgc ccaggctaga gtgcagtggt gcaatcatag ttcactgtag tctcaacctt    1500
ccaagctcaa gagatcctcc tacctcagcc tccctagtag ctggaacttc aggctacact    1560
acgcccagct gctatttatt atttatttat ttattgagat tgcatctcac catgttgccc    1620
aggctggcta cttaaaaaaa attttttttt tcaagacagg gtctcactct gccacccagg    1680
ctggagtaca gtgacagagt ctcagctcac tgcaacctct gcctcccagg ctcaagtgat    1740
cttcccacct cagcctccca aggagctggg attacaggta cccaccacca cacatggcta    1800 acttttatt ttttgtagag acagggtctt gctatgttgc ccaggctggt ctcaaactcc    1860
tgagctcaag caatcctcct gctttggcct cccaaagtgc taggattaca gttgtgagcc    1920
```

-continued

```
accatgcctg gccttggcca ctttagttttt gcttttttttt ttttttttttg agttggagtc    1980 ttgctctgtc atccaggctc ccaggctgga gtgcagtgac acaatctcag ctcactgcaa    2040
cctctgcctc ctgggttcaa gcaattatcc tgcctcagcc tcccaagtag ctgggaccac    2100
aggtgtgcac caccatgccc agctaatttt tatattttta gtagaaatgg gggtttcacc    2160
atgttggcta ggctggtctt gaacttctga cttcaagtga tccgcctact ttggcctccc    2220
aaagtgctgg gattacaggc aagagccacc gtgcccggct gcctacttta atttttaata    2280
aagggttgtt atataagggg taggtgagag aatgaagtaa aattgagtgt tacagtctcc    2340
agttgttaat cacattataa ttattctctt ttaaaagtta ccaacaagtt atttaaagaa    2400
tcgaatggaa ccctttggaa atacagtgtt catgcctcta gtattaatgc cagtttttac    2460
ttcgaggcca gcaagctaga ttccgatggc cttccctttc caggatggga agcggatgat    2520
tgacttcaat tttccccctt ccgttacttc tctgctccac atcatttctg tgctgatgca    2580
gggacgattt ccactccttt tacagcgtag atgttaaaag cctgtgcgga gcagctcatt    2640
catcattttc cgcagagctt taccoctcac ttccccagcc agctaaatgc aggctgttct    2700
tgactctctg atctaggccc attgcagggt gagggccagg ctcaggagtt tccagggtga    2760
aaaccaggta agcttgatgt tggaaggatg aagaaggacc caaaagggtc tgagatgcag    2820
agctctccag atgggcctgg gagcctgcag gggaagaggc ctctctttat atcccggagg    2880
cctggtgcaa ctctagttgg tttcatgttt gttgcgagta acagcagctc acatgaagcg    2940
gtgcaccatg ttcattttac atggattcat ctcaaggact gcttacaaaa aggccaggaa    3000
gtagctgatg ttcttcccat cttacaggta gggaaattga ggcatggaga ggcaaagtta    3060
cttgcccatg gtcatatagg tagaaagcag cactggcaga ttcaaagcca gacatctact    3120
ctcagataca cgccctgggc ctcaaggcca gtttgcctgg gcatttccct ttaatgtctc    3180
ctctctggaa gtgaatggtg tcatcagaaa ggttccagtg ccagcaccaa tcaatgactg    3240
tcccagtgag agcttggtca aatccctttta ccctgcagg gactcaattt tctcacctgc    3300
aaaatggggg tattaataaa gccaccccccc gcaccccccgg ccccccagccc ctccacctgg    3360 ttgcaagagg agtggttgta gactaagggc ctgcgtcaag tacagaaccc aggagggtc    3420 tgcccaactt taaccctctc tccaaatcct ctagcctgaa gcagcagaaa cccacgtggg    3480
actgggggct gcccccttcc gggccttccc caagcagagg ggtccccatc tagccccgcg    3540
gggcaacggc ggccggtggc tgcgtgaagg gcccccctccc ccgacgccgg ggagcaggaa    3600
ggccactcgg caccatattt agtcaggggg agccggcagc ccagagctgg tatgcggcgc    3660
tgggaattcc tgcaggaagg agtccgcgcc tgcccttttt gggttgtctc ccgcccgccg    3720
ctcccgccgc tcccggggag ggggaccggc ccggcccggc ccggcccggg aacctcggag    3780
gagctggtgc cgcgcgggga gcggagcgcc cgggctgccc gcgggtcccc ggcctggcgc    3840
ggggccagcc caccgcctcg acttccttttt atggcctgtg tgtgcgtgcg tggacaggag    3900
cggggaggga gggacgggga gaagacggag agcctgggga agagagagag agaaagcgca    3960
gagataggag tgagacacgc gggagagatg gagagcaaga gacacagaga ccagagacaa    4020
agtgagacag gagggagaga cagatacatc gacagatcta gagaagcgag agggacagag    4080
acaaaagata gagcgagaga cagcaatgat cagagtgaca gacatgcaga gacagtggca    4140
gagacagagc gagagagcct gtgatggaga gagacagga atgcaatttt aggcgaggaa    4200
tccttgggga agggaagttg ttgaagggaa ctcgcagact ctgggggcac acccactttc    4260
```

```
tccttggatc ttgacacttg catcttgtaa ataacgtaat tatcaccgcc accgccttcc    4320 cccatttgt agctatggac accaagtctc agagaagtga agtgacttgc ccaaggtcac     4380
gcagctggcg agtggcgcac aggggagggg gacagctgaa ataatcacag tgggcttatt    4440
tttaattttt atttgtattt tggtcgtggt gatgtgggtg gaggtggaga tggcaagttg    4500
ggaaaagtaa aaacttcccc ttcctgcacg gttcccagca agggtggggg cctcctgtct    4560
tgcactttgc aaagttcaag aaatccccctt tccctaccct tcacgctgca cagccggccc   4620
tctttccaga cagtgcgatg ccaataaaat gggaagtggg gtgggagatg tcaagtcaga    4680
tccaccacag ccccgacacg gggaggaaga ggttaaagcc tttgcggccg gaaccgactc    4740
agggaagacg ttctcaagca tcccgcacag acactgcctg ctcgaccccc tttctctagg    4800
gatccggagc gtctgcgacc gcctggggcc ggggctgaga ctcccgtccc tgtgcgcacc    4860
tgttccgtgc gcccttgtgc ggtgcgcacc tgttccgtgc acccttgtcc cgagcgcccc    4920
agctccttgc gctcccgccg ggggtgcgcc ctgcaggggg cgcggcgagg gggccgcgag    4980
ggaccctccc caactccacc ccttcggcct cctcccttt cccagccgcg ggcagctccg     5040
ggtctataaa gagaggcgtc cgaggacgcg caggagatt tggacgctcc ggcctgggag     5100
gtgcgtcaga tccgagctcg ccatccagtt tcctctccac tagtccccccc agttggagat   5160 ctgtaagtag tagttgtcat tctggggggca gattgcaggg caggggggtg ttaaaagtcc   5220
tatagggtat tctatagggg ctgggggtgca cttagggggtc cctgttgtca acctcgtaag  5280
ggccatggtg ggggcagagt tgtgatttgg atctctctct gccttatcgt cttagattat   5340
cctagacttt ccccaaacag catttcttaa gattgccagt gagaagtacc attttggggg   5400
tgcttattaa cgatatcaat gcctggaccc aactccattt cccaactcta gaatccccag   5460
aaaaactgcc ttaaaaaaaa aaaattagt cccgagtgat tcttgttaag aggctaatcc     5520
aggagatatg ctcccttgga aatctcagag gtccggtgca gacaatcaag gcatctcact    5580
tttattctag gcaccaaaaaa atttacagct gaacttcact gaaaagtcac ttgctatcac   5640
acagaagggc aaagtgaggc tccttgtgga tttgaccgta ttgcacagtt gtgttgataa    5700
tgcattaaat cagttaaaaa cacatgggca taggcttagc agaaaggagt gttgttgttt   5760
ttttttttta atcagtttag gggaggttct tctatgttga gaaccctgg gagataaggc     5820 tggttgtgat ctagtttgtt acagcccact ttttcctctt ctccaaatta aaaaaaaaa    5880 aaacaactca cccaggttga ccccaaaggg ccccccagata cccaggtggg ctccaaagtc   5940
tccatttgct tccacgatct gcaggtgcgt taggtaagat tacactagaa tttccgcag    6000 agccacctgt gtcaatgcca ctctcgtgcc caaccaaatg ggtaaaacga gagaaagtgt    6060
ggctactgcc tgttgtaagt tttcttccag cacagggtct ggtagggatt ttgccacttg   6120
agaaaaggta ccatccaaag ccatgcttgt caagaagtaa aagaaaatat ttagaaaccc    6180
aaggtgggag tgtttagttg cagtatgaag aactgagaga ttaaatggtg aactgtccgt    6240
ccggggtttg gcaaaagaa tgcaggctat taataaactg ctttgcatag tttttttgttt   6300 ctttgattta ctcaacgata ctattttaga attgttcaga gacggaactt gacgctgaac    6360
tgaaagtcat taggtggcag ggtgtgaaat aagatagaga attttgttttg aaggaaattg   6420 atgttttccc tttgagatag ctaccgttga tggaacactt cagtgccaca tgctgttgca   6480
acatttaact taatttatct catttaatct ttgcaacaac ttcataagaa aggctttatg    6540
atgcctgttt agtatacaag gcagctgagg ctcagagagg taaagtgtca cacagccagc    6600
aagtggtaga acccattccc gggtcagttt gagtccaagt tcatacccctt gaccccacta   6660
```

-continued

```
tctttcttct ttaccatgga cacaaacttg ttggggtcag gtttctggtg ggactaaatg      6720
cttccaacaa agtaaatgtt tatcaccgtg tcctttgaag aaaacataaa ctgactttt       6780 gcacatttaa aataaaaggc actgtttgtc ccctgattga gggggtgacc tagctgaaac      6840
cagtgaccct aggtgggctg ccatgccgag agtccagaac gtgaactagc tgggtctttt     6900
ccgagaagcc gccaggcttg ccttgtaaac accatgtttt tttattatca tgtccgaaat      6960
agatgtgtta ttccgtacaa ggtatctgtt atggatttgt tatcattact tttccgtggg     7020
agggcagaga ttgaggcaaa catgcccatt tatggaagcg ttttccatga ggccatcccc     7080 ggcccctcg tcagttaccc agccttgcac cgcagcccgg ttggtcctgg ccctggggat      7140
ttgtctacca tgtccctcac ccattgaaga actagtggag aaaccctaag gagaagagat     7200
ttgggaggaa agtgggattc ttttttccta ccccctctta ttcagaggtt tgattttttt     7260
gggtgggggg tgggagggaa ttgtctcctt tccacaggtc ttgaatccaa acaggtgggt    7320
cttccacgtt aggcacaagc gtgtaattcc aagagcagat atatagtaga ttttcttga      7380 aaaccaagtt caatattcaa tccagtagaa tcatagaagg ccataagcaa atttaaaaat     7440
catctcccgc acctccccaa acctcacttt ctcatccggg aaatgggct aatgagaata      7500 actcatgttt tttgggcact tttgcctggc gagatgctaa acgctttgtg gacattatct     7560
tacgtcttca taacaaccct ttagagtaga tactgttatt ctaactggct ttatttaca     7620 catatggagt ctgaataact tgcttaagat agctcagcta accagtaagg aaaagaagat     7680
tctacaaatc taggtctttc taactccaga gtttcacaga ttaccctcat gggaggattt    7740
gatgagctaa tgtgtatgaa gggtttagca cagtgcctgg cccctggtaa gcttcagtga    7800
tggttattta tagcaaacac aaccagagag ttcaagatgt ttgctcagta tggcatggct     7860
catctttggc agaaccggga agcctaaact atgtggccgt taaaggagaa gcttctctta    7920
attttcttcc ctttgatctc ataaacctcg tttctatttg ggctgaaagt ggtgattaga    7980
atctttaata tattaagcta ccattcctta cctggattgg gaatgttaca aattccaatt    8040
acatttgttt agggttttgt ttgtttgttt ttgagacaga gtcttgctct gtcgcccagg    8100
ctggagtgca gtggtgcgat cttggctcac tgcaacctcc gcctcctagg ttcaggcact    8160
tctccagcct cagcctcctg agtagagagt agctgggttt ataggcgccc accaccatgc    8220
ctggctaatt ttttgtattt ttagtagaga tggggtttca ccatattggc caggctggtc    8280
tcgaaccgct gacctcaagt gattcgcctg gcttggtctc ccaaagtgct cagattacag    8340
gcgtgagcca ccgcgcctgg cttatttagg gtcttgatgg catactttaa gggatggcct    8400
ttttgctctc taggtcttct ccttccactc ctgacctttc aacttttaac cctggccaca    8460
caatggagga aagactgaat ttagagaaag gcaggcaaga atttgaaaga aaccttgtat    8520
gtgatccaag gacagaggaa gaagctgctc acagtggctg aaaggggagg tcggacatct    8580
gtgacttgta tcagggtttc aggggctaag gaggaacaac ctcatcaaag ttgctaggaa    8640
agggccatag aggccaggta tgcaggtca tacctgtaat cccagcaatt tgggaggctg     8700
aggtgggggg atggcttgaa gtcaggagtt tgagaccaga gtgggcaaca tagcgaggca    8760
ccatctctac aaaaaatttt taaaatgag ctgggcatgg tggcatgcat ctgtagtcct      8820
agttattcag gaggttgagt gaggcaggag gattgcttga gccaggagt tcaaggctgc     8880 cgtgggccct gattgcatca ctgttctcta gcctgggcaa cagagtgaga ctctgtctca    8940 aaaaaaggt gagggcata gaactttact gtaccaggct gaaaaataca aggcccagag     9000
```

-continued

```
agggcaagtg acttgcctag catcacccag cgagttttgg gcagagctga gacttgtaac    9060
tcgaagacct aaggatcttc cacaggctaa tgaatagctt gtttgtgctc aagggatgaa    9120
gcagtgagtt gttaggacag gactgtgaat agggctgaca tattcagatg tgtcaaacat    9180
cgctaatgcc atctctgagt aaattaggct tcaaacagat cgggattcta atcctggttc    9240
cccaactttt gcaagggagg gccttgcatt tacctttcaa gaccccgata ggcttagcag    9300
gaaaatggga ataatagata atgccactct ttcatccttg acttttttgt ctaattatat    9360
gaatttatct gtaggataaa ttcccagaaa tgcgcttgct gagttaaagg gcatgcgtat    9420
ctaaaattaa tagatattgc aaatgactgg ctaaagacat tgcagaccag gtgcagtggc    9480
tcacgcctgt aatcccagca ctttgggagg ccgcagcagg tgggtcacct gaggtcagga    9540
gttcaagacc agcctggcca acatggtctc tgctaaaccc tatctctact aaaaatacaa    9600
aaattatctg ggcatggtcg tgggcacctg taatcccagc tactcgggag gctgaggcac    9660
gagaatcgct tgagcctcag aggcagaggt tgcattgagc cgagatcaca ccactgcact    9720
ccagcctggg caaagagtga gactcggtct caaaaaaaa aaaaaaaagg cattgcaaat    9780
tgcaacttgt tgcagtcaca tatgacagca gtccccatcc tcttggcacc agagactggt    9840
ttcgtggaag acaatatttt ccagggtgga gtggggagga tggttttggg atgaaactgt    9900
cccacctcat catcaggcat tggttagatt ctcataagga acgtacaacc tagatccctt    9960
gcaggtggag ttggcaatag ggtttgtgct tctgtgaaaa tctaatgctg cttatctgac    10020
aggaggcgga gcttaggcag tgatggtcac tcacccaccg tcccctcctg ctatgtggcc    10080
tggttcctaa caggccattg actgatactg cagcacaagg gttggggacc cctgacatag    10140
gagactatac atttatttta agctgtggta tgccagaatt gtaaaatata aaacacagtg    10200
gggcttttag ggccagaaat aatcagttct tgctcgcttc cagaagcatc cttcacaggg    10260
gctaccgtaa ctcttgccaa ccaagttctc ttggttggga ggaaaaaata gtgttatgca    10320
ttaagagaac ttctttctgg agttacttga aaccattggt attcagatga ttaggcagat    10380
gtcacaaggc aataagaatg tgacaggttc accattcact ttttttcctg taaaagtgaa    10440
gtagggcttt cttgggaaca gcccttgggg aggtggggg atgtgaatgg tgaggggagg    10500
gtagaaatgg tggagtaggg tcaggggcaa gaaagggact ttctgctaag aattaatcgg    10560
gtgtccattt actcttagca gaaaactagg attagattct ggattgtact cctgactcca    10620
aattttacaa gtgggggtct tgcatttacc ttccaggacc tcggtcatct tagcaggaaa    10680
atagcaatag caggtgatgc caccttacag agcgcttagg agacagtgag atggtctata    10740
taggaagctg tctggcctga tacctgatga atacaagggg cccaataaat acagtggctg    10800
ttatgaataa tagatctaaa ctgccttttt ggtactactg gggacctgcc aagcaggtgc    10860
atttagagtg cccagtgcct ctccctgcga cacatttgat gcctccctac acctggacca    10920
ggccttgagc gaggatttcc actgcagagg tccttccagc tggcgaattg tgttgcagat    10980
caggttcaga gaacttctgt tttgcctgtg tggcattcat tcattcgttt atttgaaata    11040
gagatgggat ctcactgtgc tgcccaggct agtctagagc tcctaattca agcaatcctc    11100
ttggcttggc ctcccatagt tcttggatta caggtgtgaa ccactgtatc cagcccttta    11160
tgacatttag aatatgagca attttctctt tttcttttt ttcttttgga gatgagtctt    11220
cactctgtca cccaggctag agtgcagtgg catgatcttg gctcactgca acctctacct    11280
cccaggctca gcgatcttc ccacctcagc ctcccgagta gctgggacta ccggcatgtg    11340
ctgccatgcc tggctaattt ttgtattttc tgtagagatg gggtttcacc atgttgcgca    11400
```

```
ggctggtgtc aaactcctaa gctcaagcga actgcctgcc ttggcctccc agtgttggga   11460
ttacagacgt gagccacagt gctgaaccct gcatggtatt tagaatataa gcaatactct   11520
aacatctggt ctgggtcact ctgtattact tacctgatct ccaaaaacat ttgggttttt   11580
gtctctggtc caaaatcttt agccaatggc ttggcagtaa aatcctgagg aagctgttg    11640 accaggtgag gtgatgtgca aatcctatac tctctgggct ctgggatatt taatttacta   11700
tttatttatt tattttcaag acagagtttt gctcttgtcg cccaggctgg agtgcagtga   11760
tgggatctca gctcactgca ccctccacct cctgggttca agcgattctc cttcctcagc   11820
ctcctgagta gctggtatta caggcgccca ccaccacacc tggctatttt ttgtattttt   11880
agtagagacg gggtttcacc atgttggcca ggctggtctt gaactactga cctcaggtta   11940
tccgcctgcc tcggcctccc gaagtactgg gattacaggc atcagccacc atgcccggcc   12000
taatttactt tttattaatg ctgaagcaga gagggcaaga tcttttgccc ctgagttctt   12060
ctgggaaaaa tgaaactgat ggtaaaacaa actaaagcaa cctgacattc tcagttggtc   12120
cagtttcagc cctttgactg ggagtcacag acgggtccca taaatggta gagctgggcc    12180 agcctaccat tgatttattt tccctaaatg aaaaatacaa ggcccagaga gggcaagtga   12240
cttgtccaga gtcacccagc aggtttgggg caaagctgag actcgttact tgacatccta   12300
aggtcttcca gaggctaatg attagcttgt ttgtgctcaa aaaatgaagc agcctgggcg   12360
cggtggctca tgcttgtaat cctagcactt tgggaggctg aggcaggcag atcgcttgag   12420
ctcaggagtt tgagaccagc ctgggccaca agtgagacc cctgtctcta caaaaaaatg     12480
caagaattaa aaaattagct gggtgttctg gtgcgtgcct gtgatcccag ctacttggga   12540
ggctgaggtg ggagaatggc ttgagcctgg gaggcagagt ttgcagaaag cagagatcgc   12600
gccacttcac tctagcctgg gcaacagagc cagaccctgt ctcaaaaaaa aagaatgaag   12660
cagttgttgg tcaggacagg actgtaaaca aggctgacac actcagatgt gtcaaacatc   12720
gctaatgcca aaggtgacag agtcatttgt tttcatccaa acattcgaga aagttggacg   12780
aggtgactca cgcctgtcat cctagagctt tgggaagcca aggcaggag  atcatttgag     12840 atcaggagtt tgagaccagc ctaggcaaaa tagcaagacc cccatctcta caaaaaataa   12900
gccgggcata gtggcccaca cctgaggtgg gaggatccct tgagcccatg agtttgagcc   12960
tgcagtaagc tatgattgca ccactgcact ccaccctggg catatagtga gaccctcccc   13020
ccaaccaaaa acattgagag cagctcttga tgagtgaact gtacttcgtg gtcagcagtt   13080
ctgggtagta atttcagaga tgtcctttca gcccttggag ctgatgcagg accttaaaca   13140
tgagcgatgg tggaggaggg agggttggga aggtgcatca aggtagatga agagtgtccc   13200
tggggttggg ccaactggcg gtccgtctct ggtccagtgt gttcaccttg ccccgtctg    13260 atcttctgca gttggtattc cgagttgagt ttgactaagt gagagctgct ctcagcttta   13320
actgcctttc ccaagacagc ccttgttttt attctaaagc tgtggttctc aactggaagc   13380
agttttgcca ccccaggga catctagcag tgtctggaga cattttttgat tgtcatgagt   13440 ggaggaaggg gtgctactgg catcaggtgg gcagagacca gggatgctgc ggaacatccc   13500
acaatgcacg gaagagctcc cctcacgaca cagaatgacg cagcccaaga gtcacagtgc   13560
agagtttgtg gccagctgcg gtggctcacg cctgtaatcc cagcactttg ggggccaag    13620 gtgggaggat tgcttgaggc ctggagttca gaccagcct ggccaatatg gtgaaacctc     13680
atctctacta aaaatacaaa aattagccag gcatggtagc gcatgcctgt agtcccagct   13740
```

```
acttgggagg ctgaggcacg agaatcactt gaacccagaa acgtggaggt tgcagtgagc    13800
tgagattgcg tcactgcact ccagcctggg taacagagcg agactctgtg tcaaaaaaaa    13860
aaaaaaaaaa aaaagactta gcaactatta ttactagtat tagtattatt aatttgtcag    13920
gctcactgaa ttttctcaaa aatttggcaa attttagga aaacattctc aaaacatttg    13980
gcaaatctgt ggctaaatgt tgttttgggg acccaaggct cgtaggagca aaacagcttt    14040
caggtttccg gatctgccag agactcaagt gtcctgttgt gtgttttgtg tctcaatgag    14100
ggaaagggga atatgtagca ccttccagat ggatttgacc ttgactgcgc cactgtttga    14160
agagcttctc aacctccgca gctccacccc agcccagata tttcagggaa ttagggttcc    14220
aaggggcatg ctatggaaaa caccattcta gcatgagtcg aagcttctca tcccccatct    14280
tgctgtcttt tgaccaaagc agattttgca cgtcgtaact gtcagagaca tcaaagccag    14340
agggaatcca gcctgctcca agctctcctt ttttgtacag agactgaatc tttgcacttg    14400
atcttgtttg tgttttttaag tctgaggtta gacagggtcc caggcaatgg aggcgtgcgt    14460
gtccttttat ttttctgttg tagcttttgc tattttttct gacttttaag gcaactcatc    14520
cacatggcaa ttaggaagag cccacttagg gctgggcaca gcggctcatg cctgtaatcc    14580
cagcactttg ggagaccgag gcaggcagat cacttgaggt caggagttca agacctcagc    14640
ctggacaaca tggtgaaacc ccgtctctac aaagaataca ggaaaatagc tgggcatggt    14700
ggcaggtgcc tgtggtccca actatttggg aggctgggt gggaggatca cttgagcctg    14760
ggaggcggag gttgccgtga gctgaggtca tgccactgca ctccagcctg ggcgacagag    14820
caagaccctg tctcagaaaa aaaaaaaaa aaaaagaag tccactttac ttgtcatagt    14880
gcttagaaca aatgaaacac tctcctagcc ctcttgggat gtaattggct accatctgca    14940
caaactcttc attattgcac aagaatatca atatacttaa tgctactgaa ctgtgtttaa    15000
gtggccgagg tggtgaatgt tagctgtatt ttaccacaat taaagataag agggaaggaa    15060
aatgaagtgt actttacaac caaaaaagta cgcttgatgt gcaaaaaagt gtgcagcttg    15120
atgaattttc aagaggatat attttttata gatgggggtc tcactctgtc acccaggctg    15180
cagtgcagtg gcatgatcat ggctcactgc atccccgacc tcctgagctt aagtgatcct    15240
cccacctcag cctcctgagt agctgggact gcaggtgcac actatcacaa ccggttaatt    15300
tttgtatgtt tgctagagac aaggtttcac catgttgacc aggccggtct cagcctcctg    15360
ggctcaggtt atcctcctac ctcagtcttc cacacaggta attaaaaaac attttttctt    15420
agagatgggt cttgctgtgt tggccaggct ggtctcaaac tcctgggctc aagtggtcct    15480
cccatcttgg cttctcaaag tgctgggatt acaggcgtga gccatgtcac ctggcccaac    15540
agtttgatga atttcagaa agtgaacact cataggctg gcattcagat gaagatctag    15600
aggtcaaccc tcacaagccc ccctcacgtt ctgtccttgc aatcattgca caccggagac    15660
tcattcattc cttatctgag ttctatcacc gtagattaat tctgcctggt tttggacctc    15720
agttcaatag tcacagaacc tgtgcttttt gtgaccacct tcttttgctc aaggatgtgt    15780
tgtgagatgt cctttttgt ggtgtggagc tgtagtttac ttcacctgat tcgagtccta    15840
ttttgggtgt ttgtaatgtg tcaggtactg tgccaggtgc cttacaggat tgattccttt    15900
atgggcatct gacaagccca cccaccttat gtgaaaggca gaaccaaata gactccagaa    15960
tgagacccag gtttgggtcc cagctctgac acttcttttt ttttgagatg gaggctgact    16020
ctgtcgccaa ggctggagtg tagtggtatg atgtcggctt acggcaacct ccacctcccg    16080
ggttcaagtg attctcctga ctcagcctcc caagtagctg gggctacagg cacgtaccac    16140
```

```
caatcctggc taattttttaa ttttttgtatt tttagtagag acagggtttc acaatgttgg    16200
ccaagctggt ctcaaactcc tgacctcaag ttatcctccc acctcagcct cccaaagttc    16260
tgggattata ggcatgagcc atcacactcg gcctacttgt gatcaatctt acttcatctt    16320
cacaccctcc catttctctt acgcatcctc cagtttctct ctctctctct ccttcttttt    16380
ctctctctct ctctcacaca cacacacacg atctgctgcg acaccttaag aaacaagaga    16440
ttatcaggga atgattgaat attttgccgc atttcctatt ttgctgcctg tttaaactaa    16500
ccttggttat actattaaaa gaagacgcgt cgtatcaagc cacttctgtg actatggctg    16560
tccagaaata aacataatta aaacatccaa cagtagtaaa tgctattggt taggaatgag    16620
cgaagtggct tagagtcacc ggaagtgaga aagggtatag aaacagaagg tacttggtgt    16680
agatcagggg tgtcctatct tttggcttcc ctgggccacc ccagaaaaag aagaattgtc    16740
ttgggccaca cgtaaaatac actagcacta atgatagctg atgagctaaa aaaaaaaaaa    16800
aaaatcgcga aaaaatatca tactgtttta agaaagttta tgaatttgta tcgggccaca    16860
ttcaaagccg tcctgggccc catgcagcct gtgggctgca ggttagacaa gcttggtgta    16920
gagagtttca tctaaacttc atggcagctc tgcagggcac ccgttaggtc cccagtatta    16980
atatacagta aatctgagtc tcagatctac gtaagtcacc cagaagcacg cattctgcag    17040
tggcagagtc acgtttgaat tagcatctga ttgcaaagtc tgggtgtctt tacatgacta    17100
caggttatct tacctctcaa gaggaggcaa ccaatcaaat gttgccagca ccaatgaact    17160
tgtactttat ttaggctcag aaagatcttt taggctaatg aaaatgccct atatttatga    17220
aatgttctcg ttctctgtgg ctttctcttt tttgagacag ggtctcaccc tgacacccag    17280
gctggagtgc agtgatgtaa tcatagctca ctgcagcctc aaactcctgg gctcaagcaa    17340
ccctcctgcc tcagcctcct agtagctggg actacaagca cgcatcatca tgcctggctg    17400
atatttttt taagggatgg ggtcttgcta taatgcccag tctggtctcg aactcctggg    17460
ctcaagcaat cctcctgcct tggcctccca aaatatggga ttatacatgt gggctactgc    17520
cagcctcttt tctttcaatt attttttaat ctatgggttc ccctcctttt tgtttgtatt    17580
ttatttgtta aagaaagaga gtactggccg agcgtggtgg ctcacacctg taatgtcagc    17640
actttgagag gccaaggccg gtagatcacc tgaggtcagg agtttgagac cagcctggac    17700
aatatggtga aaccccgtct ctactaaaaa tacaaaaatc agccaggcgt ggtggcatgc    17760
acctgtaatc ctagctcctc gggaggctga ggcaggagaa tcacttgaac ctaggaggtg    17820
gaggttgcag tgagccaaga tcccgccatt gcactctagc tgggcgacag agcatagtct    17880
ctcacctttg ggagtttact gcattgttta gcatgctctc ctgtgccttg cattttccat    17940
agacaggcgt cagatctgga ggcttcatca ccttcatccc ccatctccat ccccttttct    18000
tttgagcaag aatatgtcat tagtggtaac ggcacttcct gtagtgggcc atctgcaggc    18060
atgtaatgtt tataatgtct agtcagctct ctcttttgt gatgttaggg ttaattagta    18120
gatttaggtg atggcaggcg gacccatccc ttaaaaattc cacaagagct cttcatctga    18180
tatagtcagt cttgtggtgg ggaccctaga ccagcatcat catcatcacc cggaagctgg    18240
ttaggaatgc atattcttgg gccccatccc agtcctactg actcagaagc taatgcacca    18300
ggaaatgtga gccccattgg cctaatggtt ttagcaatta ctggtagaac ttgccaactt    18360
gccaagaccc tttctttctt cctttctttc tttttttttt tttgagacgg agtctcactc    18420
tgtcgtccag gctggagtgc agcggcgcat ctccactcac ccactcactg caagctccgc    18480
```

```
ctcccaggtt cacaccattc tcctgcctca gcctccagag tagctgggac tacacgcggc    18540
cgccaccacg cccggctaat ttttttttttt tttttttagta gagacagggt tttgccgtgt    18600
tagcc                                                                 18605
```

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: CArG PCR
      primer 1

<400> SEQUENCE: 18

```
ctggagctct tattagtact ggggtccc                                        28
```

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: CArG PCR
      primer 2

<400> SEQUENCE: 19

```
actcaggcca taaaaggaag tcgaggcaga gttgg                                35
```

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Intronic
      CArG PCR primer 1

<400> SEQUENCE: 20

```
ggccaagcca ccctggagaa acctggac                                        28
```

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: SM-MHC-4000
      PCR primer 1

<400> SEQUENCE: 21

```
atgtcagatg tcctctcact gctttattcc                                      30
```

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: SM-MHC-4000
      PCR primer 2

<400> SEQUENCE: 22

```
agcaaacagc tttaaatacg tattggcttc                                      30
```

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Intronic
      CArG PCR primer 2

<400> SEQUENCE: 23
cccagaactc aagccagtca ggctgcatcg					30